US005614523A

United States Patent [19]

Audia et al.

[11] Patent Number: 5,614,523
[45] Date of Patent: Mar. 25, 1997

[54] COMPOUNDS HAVING EFFECTS ON SEROTONIN-RELATED SYSTEMS

[75] Inventors: James E. Audia; Joseph H. Krushinski, Jr., both of Indianapolis; Kurt Rasmussen, Fishers; Vincent P. Rocco, Indianapolis; John M. Schaus, Zionsville; Dennis C. Thompson; David T. Wong, both of Indianapolis, all of Ind.

[73] Assignee: Eli Lilly and Company, Indianapolis, Ind.

[21] Appl. No.: 470,512

[22] Filed: Jun. 6, 1995

Related U.S. Application Data

[63] Continuation-in-part of Ser. No. 373,823, Jan. 17, 1995, abandoned.

[51] Int. Cl.⁶ .......................... A61K 31/50; C07D 241/04
[52] U.S. Cl. .......................... 514/252; 514/253; 514/254; 514/414; 544/358; 544/359; 544/238; 544/253
[58] Field of Search .................................. 548/469, 465, 548/151, 218; 544/238, 253, 358, 359; 514/252, 253, 254, 414–415

[56] References Cited

U.S. PATENT DOCUMENTS

| | | | |
|---|---|---|---|
| 3,929,793 | 12/1975 | Popelak et al. | 260/268 |
| 4,146,630 | 3/1979 | Kampe et al. | 424/267 |
| 4,244,961 | 1/1981 | Kluge et al. | 424/267 |
| 4,288,442 | 9/1981 | Friebe et al. | 424/267 |
| 4,304,915 | 12/1981 | Berthold | 546/201 |
| 4,361,562 | 11/1982 | Berthold | 424/250 |
| 4,460,586 | 7/1984 | Berthold | 424/250 |
| 4,803,203 | 2/1989 | Caprathe et al. | 514/230.5 |
| 4,849,431 | 7/1989 | Sugimoto et al. | 514/331 |
| 4,935,414 | 6/1990 | Stenzel et al. | 514/250 |
| 5,013,761 | 5/1991 | Beedle et al. | 514/650 |

FOREIGN PATENT DOCUMENTS

| | | |
|---|---|---|
| 0000485 | 2/1979 | European Pat. Off. . |
| 2073738 | 10/1981 | United Kingdom . |
| 2163150 | 7/1985 | United Kingdom . |
| 92/18089 | 10/1992 | WIPO . |

OTHER PUBLICATIONS

Mutschler Drug Actions Basic Principles and Therupeutic Aspects. MedPharm Scientific Pub. (1995) pp. 309–312.
Foye et al. "Principles of Medicinal Chemistry" published 1995 by Williams & Wilkins (Media), pp. 199–200, 208.
Artigas, et al., *Arch Gen. Psychiatry*, 51, 248–251 (1994).
Hoey, et al., *European J. of Pharm.*, 231, 477–480, (1993).
Marxer, et al., *J. Org. Chem.*, 40, 1427–1433 (1975).
Parham, et al., *J. Org. Chem.*, 41, 2628–2635 (1976).
Yamato, et al., *J. Med. Chem.*, 24, 194–198 (1981).
Evans, et al., *J. Med. Chem.*, 35, 3919–3927 (1992).
Efange, et al., *J. Med. Chem.*, 37, 2574–2582 (1994).
Chambers, et al., *J. Med. Chem.*, 35, 2033–2039 (1992).
Armah, et al., *Br. J. Pharmacol.*, 96, 807–816 (1989).
Derwent Abstract, Japanese 2121-924-A 1981.
Derwent Abstract, Japanese 2121-966-A 1981.
West, et al., *Psychopharmacology*, 104, 91–96 (1991).
Hilleman, et al., *Arch. Intern. Med.*, 152, 350–352 (1992).
Artigas, *Tips*, 14, 262 (1993).
Fuller, *Life Sciences*, 55, 163–167 (1994).
Jacobsen, *J. Clin. Psychiatry*, 52, 217–220 (1991).
Hjorth, *J. Neurochem.*, 60, 776–779 (1993).

*Primary Examiner*—Mukund J. Shah
*Assistant Examiner*—Anthony Bottino
*Attorney, Agent, or Firm*—Joseph A. Jones; David E. Boone

[57] ABSTRACT

A series of hetero-oxy alkanamines are effective pharmaceuticals for the treatment of conditions related to or affected by the reuptake of serotonin and by the serotonin $1_A$ receptor. The compounds are particularly useful for alleviating the symptoms of nicotine and tobacco withdrawal, and for the treatment of depression and other conditions for which serotonin reuptake inhibitors are used.

19 Claims, No Drawings

COMPOUNDS HAVING EFFECTS ON SEROTONIN-RELATED SYSTEMS

CROSS REFERENCE

This application is a continuation-in-part of application Ser. No. 08/373,823, now abandoned filed Jan. 17, 1995.

FIELD OF THE INVENTION

The present invention belongs to the fields of pharmacology and medicinal chemistry, and provides new pharmaceuticals which are useful for the treatment of diseases which are caused or affected by disorders of the serotonin-affected neurological systems, particularly those relating to the serotonin $1_A$ receptor and those relating to the reuptake of serotonin.

BACKGROUND OF THE INVENTION

Pharmaceutical researchers have discovered in recent years that the neurons of the brain which contain monoamines are of extreme importance in a great many physiological processes which very strongly affect many psychological and personality-affecting processes as well. In particular, serotonin (5-hydroxytryptamine; 5-HT) has been found to be a key to a very large number of processes which affect both physiological and psychological functions. Drugs which influence the function of serotonin in the brain are accordingly of great importance and are now used for a surprisingly large number of different therapies.

The early generations of serotonin-affecting drugs tended to have a variety of different physiological functions, considered from both the mechanistic and therapeutic points of view. For example, many of the tricyclic antidepressant drugs are now known to be active as inhibitors of serotonin reuptake, and also to have anticholinergic, antihistaminic or anti-α-adrenergic activity. More recently, it has become possible to study the function of drugs at individual receptors in vivo or ex vivo, and it has also been realized that therapeutic agents free of extraneous mechanisms of action are advantageous to the patient. Accordingly, the objective of research now is to discover agents which affect only functions of serotonin, for example, at a single identifiable receptor.

The present invention provides an extensive series of pharmaceuticals, some of which have highly selective activity as antagonists and partial agonists of the serotonin $1_A$ receptor.

Some of the present pharmaceuticals have a second activity as inhibitors of reuptake of serotonin. The best-known pharmaceutical with that efficacy is fluoxetine, and the importance of its use in the treatment of depression and other conditions is extremely well documented and publicized. Recent scientific articles, for example, Artigas, *TIPS*, 14, 262 (1993), have suggested that the efficacy of a reuptake inhibitor may be decreased by the activation of serotonin $1_A$ receptors with the resultant reduction in the firing rate of serotonin neurons. Accordingly, present research in the central nervous system is focusing on the effect of combining reuptake inhibitors with compounds which affect the 5HT-$1_A$ receptor.

It has very surprisingly been found that a defined portion of the present pharmaceuticals are potent serotonin reuptake inhibitors, as well as having effects at the 5HT-$1_A$ receptor. Such compounds are not believed to have been known before.

SUMMARY OF THE INVENTION

The present invention provides a series of new compounds, methods of using them for pharmaceutical purposes, and pharmaceutical compositions whereby the compounds may be conveniently administered. The scope of the compounds useful in the methods is somewhat more broad than the scope of the novel compounds.

The invention provides the following compounds of formula I:

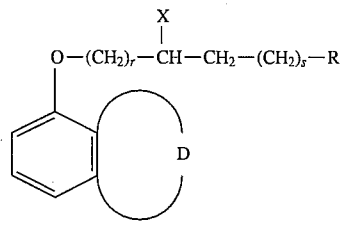

wherein r is 0–4;

s is 0–1;

D is a residue which combines with the carbon atoms to which it is attached to complete a pyrrolyl, imidazolyl, pyridinyl, pyrazinyl, pyridazinyl or pyrimidinyl group;

wherein X is hydrogen, phenyl, hydroxy or methoxy;

provided that X is hydrogen or phenyl when r is 0;

R is

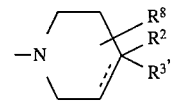

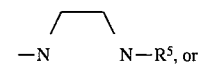

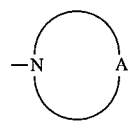

the dotted line is an optional double bond;

$R^1$ is piperidinyl, piperazino, morpholino or pyrrolyl, substituted with 0–1 phenyl or benzyl group or 0–4 $C_1$–$C_3$ alkyl, $C_1$–$C_3$ alkoxy or halo groups;

which phenyl or benzyl group is substituted with 0–2 $C_1$–$C_3$ alkyl, halo, trifluoromethyl or $C_1$–$C_3$ alkoxy groups;

or $R^1$ is

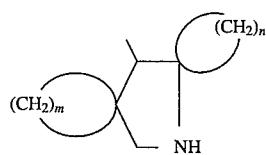

n and m are independently 4–5, and the group of Formula VI may be substituted with 0–1 oxo group and 0–2 $C_1$–$C_3$ alkyl, $C_1$–$C_3$ alkoxy or halo groups;

or $R^1$ is $C_1$–$C_4$ alkyl, substituted with pyrrolyl, furyl, thienyl, pyridinyl, morpholinyl, piperidinyl, tetrahydropyrrolyl, piperazinyl, tetrahydrofuryl, benzazepinyl, dibenzazepinyl or quinolinyl,
   substituted with 0–4 $C_1$–$C_3$ alkyl, $C_1$–$C_3$ alkoxy or halo groups;

$R^2$ is hydroxy, hydrogen, cyano, $C_1$–$C_4$ alkyl, or (phenyl or benzyl substituted with 0–2 $C_1$–$C_3$ alkyl, $C_1$–$C_3$ alkoxy or halo groups);

or $R^2$ is amino substituted with phenyl or benzyl, substituted with 0–2 $C_1$–$C_3$ alkyl, $C_1$–$C_3$ alkoxy, halo or trifluoromethyl groups;

or $R^2$ is absent when the dotted line is a double bond;

$R^3$ is $C_1$–$C_4$ alkyl,
   substituted with 0–2 phenyl groups,
      substituted with 0–2 $C_1$–$C_3$ alkyl, $C_1$–$C_3$ alkoxy or halo groups;

or $R^3$ is $C_1$–$C_4$ alkyl substituted with hydroxyimino or hydroxy;

or $R^3$ is phenoxy,
   substituted with 0–1 methylenedioxy or substituted with 0–2 $C_1$–$C_3$ alkyl, $C_1$–$C_3$ alkoxy, trifluoromethyl or halo groups;

or $R^3$ is dibenzocycloheptenyl, benzodioxolyl, benzodioxinyl, or dibenzocyclohexenyl;

or $R^3$ is phenyl, naphthyl, tetralinyl, tetrazolyl, benzimidazolyl, indolyl, benzofuryl, benzothienyl, piperidino or morpholino,
   substituted with 0–2 $C_1$–$C_3$ alkyl, $C_1$–$C_3$ alkoxy, $C_4$–$C_8$ cycloalkylalkoxy, halo, nitro, trifluoromethyl, difluoromethyl, hydroxy or trifluoromethoxy groups; or substituted with 0–1 phenyl, piperidinonyl, hexahydropyridazinonyl or piperazinonyl group,
      substituted with 0–2 $C_1$–$C_3$ alkyl, oxo, $C_1$–$C_3$ alkoxy, halo or trifluoromethyl groups;

provided that $R^3$ is not halo- or trifluoromethyl-substituted phenyl when $R^2$ is hydroxy;

or $R^2$ and $R^3$ combine to form $C_1$–$C_4$ alkylidene,
   substituted with 0–2 phenyl groups,
      substituted with 0–2 $C_1$–$C_3$ alkyl, $C_1$–$C_3$ alkoxy, halo or trifluoromethyl groups;

$R^5$ is $C_1$–$C_6$ alkyl;

or $R^5$ is $C_1$–$C_3$ alkyl substituted with benzodioxinyl or benzodioxolyl,
   substituted on the phenyl ring with 0–2 $C_1$–$C_3$ alkyl, $C_1$–$C_3$ alkoxy or halo groups;

or $R^5$ is pyridinyl, pyrimidinyl, indolyl, benzofuryl, benzothienyl, pyrazinyl, quinolinyl, isoquinolinyl, pyridazinyl or quinazolinyl,
   substituted with 0–2 $C_1$–$C_3$ alkyl, trifluoromethyl, $C_1$–$C_3$ alkoxy or halo groups;

or $R^5$ is

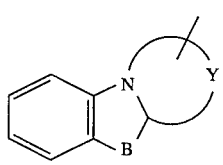   VII

B is oxygen or sulfur;

Y is a residue which combines with the atoms to which it is attached to complete a triazolyl, imidazolyl, thiazolyl or pyrrolyl ring;

A is a residue which combines with the nitrogen atom to which it is attached to complete a) an azabicyclo(octyl, nonyl or decyl) group;

b) 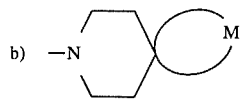   VIII c) 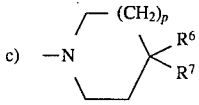   IX or d) 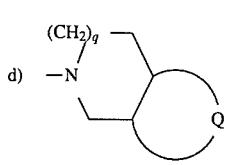   X

M is a residue which combines with the carbon atom to which it is attached to complete an indanyl, indenyl, pyrrolidinyl, tetralinyl, benzopyranyl, dihydroindolyl, naphthodihydrofuranyl, benzodihydrothienyl, benzodihydrofuranyl, benzodihydropyranyl, naphthodihydrothienyl, or naphthodihydropyrrolyl group wherein the spiro junction is not to an aromatic ring,
   substituted with 0–2 $C_1$–$C_3$ alkyl, oxo, $C_1$–$C_3$ alkoxy, pyrrolidinyl- or piperidinyl-$C_1$–$C_3$ alkoxy, $C_1$–$C_2$ alkylenedioxy, phenoxy, benzyloxy, phenyl or halo groups;

p represents 0–2;

$R^6$ and $R^7$ independently represent phenyl groups,
   substituted with 0–2 $C_1$–$C_3$ alkyl, $C_1$–$C_3$ alkoxy or halo groups;

or $R^6$ and $R^7$ combine with the atom to which they are attached to complete a fluorenyl or dihydroanthracenyl group;

or $R^6$ and $R^7$ represent hydrogen, provided that p must not be 1;

q represents 0–2;

Q represents a residue which combines with the atoms to which it is attached to complete a phenyl or naphthyl group,
   substituted with 0–2 $C_1$–$C_3$ alkyl, $C_1$–$C_3$ alkoxy or halo groups;

$R^8$ is hydrogen or $C_1$–$C_3$ alkyl;

or a pharmaceutically acceptable salt thereof.

The following genus of compounds, which is enclosed within the compounds of formula I, have efficacy as serotonin reuptake inhibitors, as well as activity at the 5HT-$1_A$ receptor.

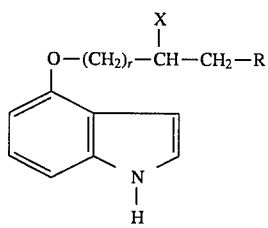   XI wherein r is 0–3;

X is hydrogen or hydroxy;

R is

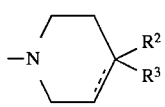  III or

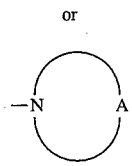  V the dotted line is an optional double bond;
$R^2$ is hydroxy or hydrogen, or is absent when the dotted line is a double bond;
$R^3$ is $C_1$–$C_4$ alkyl,
  substituted with 1–2 phenyl groups,
    substituted with 0–2 halo groups;
or $R^3$ is dibenzocycloheptenyl or benzodioxinyl;
or $R^3$ is phenyl, benzothienyl, naphthyl, indolyl or piperidino,
  substituted with 0–2 $C_1$–$C_3$ alkoxy, hydroxy, cyano, $C_1$–$C_3$ alkyl, $C_4$–$C_8$ cycloalkylalkoxy, halo, nitro, trifluoromethyl or trifluoromethoxy groups;
or $R^2$ and $R^3$ combine to form $C_1$–$C_4$ alkylidene,
  substituted with 1–2 phenyl groups,
    substituted with 0–2 halo groups;
  provided that $R^3$ is not halo- or trifluoromethyl-substituted phenyl when $R^2$ is hydroxy;
A is a residue which combines with the nitrogen atom to which it is attached to complete

  VIII

M is a residue which combines with the carbon atom to which it is attached to complete a benzopyranyl, naphthodihydrofuranyl, benzodihydrothienyl, or benzodihydrofuranyl group, wherein the spiro junction is not to an aromatic ring,
  substituted with 0–2 $C_1$–$C_3$ alkoxy, benzyloxy, phenyl or halo groups;
or a pharmaceutically acceptable salt thereof.

The invention also provides pharmaceutical compositions comprising the above compounds.

Pharmaceutical methods of use are provided by the invention, which methods comprise the administration to patients in need of such methods of use of a compound of the following formula.

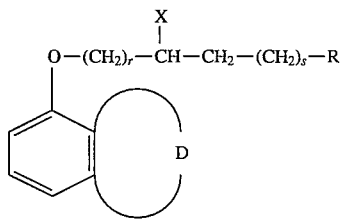  XII wherein
r is 0–4;
s is 0–1;
D is a residue which combines with the carbon atoms to which it is attached to complete a pyrrolyl, imidazolyl, pyridinyl, pyrazinyl, pyridazinyl or pyrimidinyl group;
wherein X is hydrogen, phenyl, hydroxy or methoxy;
provided that X is hydrogen or phenyl when r is 0;
R is

  II

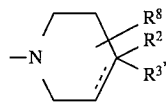  III

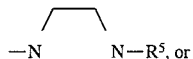  IV

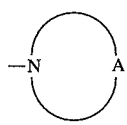  V the dotted line is an optional double bond;
$R^1$ is piperidinyl, adamantyl, piperazino, morpholino or pyrrolyl,
  substituted with 0–1 phenyl or benzyl group or 0–4 $C_1$–$C_3$ alkyl, $C_1$–$C_3$ alkoxy or halo groups;
    which phenyl or benzyl group is substituted with 0–2 $C_1$–$C_3$ alkyl, halo, trifluoromethyl or $C_1$–$C_3$ alkoxy groups;
or $R^1$ is

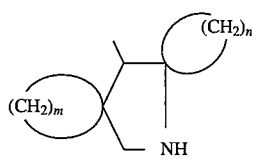  VI n and m are independently 4–5, and the group of Formula VI may be substituted with 0–1 oxo group and 0–2 $C_1$–$C_3$ alkyl, $C_1$–$C_3$ alkoxy or halo groups;
or $R^1$ is $C_1$–$C_4$ alkyl,
substituted with pyrrolyl, adamantyl, furyl, thienyl, pyridinyl, morpholinyl, piperidinyl, tetrahydropyrrolyl, piperazinyl, tetrahydrofuryl, benzazepinyl, dibenzazepinyl or quinolinyl,
  substituted with 0–4 $C_1$–$C_3$ alkyl, $C_1$–$C_3$ alkoxy or halo groups;
$R^2$ is hydroxy, hydrogen, cyano, $C_1$–$C_4$ alkyl, or (phenyl or benzyl substituted with 0–2 $C_1$–$C_3$ alkyl, $C_1$–$C_3$ alkoxy or halo groups);
or $R^2$ is amino substituted with phenyl or benzyl,
  substituted with 0–2 $C_1$–$C_3$ alkyl, $C_1$–$C_3$ alkoxy, halo or trifluoromethyl groups;
or $R^2$ is absent when the dotted line is a double bond;
$R^3$ is $C_1$–$C_4$ alkyl,
  substituted with 0–2 phenyl groups,
    substituted with 0–2 $C_1$–$C_3$ alkyl, $C_1$–$C_3$ alkoxy or halo groups;
or $R^3$ is $C_1$–$C_4$ alkyl substituted with hydroxyimino or hydroxy;
or $R^3$ is phenoxy,
  substituted with 0–1 methylenedioxy or substituted with 0–2 $C_1$–$C_3$ alkyl, $C_1$–$C_3$ alkoxy, trifluoromethyl or halo groups;
or $R^3$ is dibenzocycloheptenyl, benzodioxolyl, benzodioxinyl, or dibenzocyclohexenyl;

or R³ is phenyl, naphthyl, tetralinyl, tetrazolyl, benzimidazolyl, indolyl, benzofuryl, benzothienyl, piperidino or morpholino,
  substituted with 0-2 $C_1$-$C_3$ alkyl, $C_1$-$C_3$ alkoxy, $C_4$-$C_8$ cycloalkylalkoxy, halo, nitro, trifluoromethyl, difluoromethyl, hydroxy or trifluoromethoxy groups; or substituted with 0-1 phenyl, piperidinonyl, hexahydropyridazinonyl or piperazinonyl group,
    substituted with 0-2 $C_1$-$C_3$ alkyl, oxo, $C_1$-$C_3$ alkoxy, halo or trifluoromethyl groups;

or R² and R³ combine to form $C_1$-$C_4$ alkylidene,
  substituted with 0-2 phenyl groups,
    substituted with 0-2 $C_1$-$C_3$ alkyl, $C_1$-$C_3$ alkoxy, halo or trifluoromethyl groups;

R⁵ is $C_1$-$C_6$ alkyl or $C_1$-$C_4$ acyl;

or R⁵ is $C_1$-$C_3$ alkyl substituted with phenyl, benzodioxinyl or benzodioxolyl,
  substituted on the phenyl ring with 0-2 $C_1$-$C_3$ alkyl, $C_1$-$C_3$ alkoxy or halo groups;

or R⁵ is pyridinyl, phenyl, naphthyl, tetralinyl, pyrimidinyl, indolyl, benzofuryl, benzothienyl, pyrazinyl, quinolinyl, isoquinolinyl, pyridazinyl or quinazolinyl,
  substituted with 0-2 $C_1$-$C_3$ alkyl, trifluoromethyl, $C_1$-$C_3$ alkoxy or halo groups;

or R⁵ is

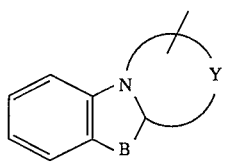

VII

B is oxygen or sulfur;

Y is a residue which combines with the atoms to which it is attached to complete a triazolyl, imidazolyl, thiazolyl or pyrrolyl ring;

A is a residue which combines with the nitrogen atom to which it is attached to complete
  a) an azabicyclo(octyl, nonyl or decyl) group;
  b) 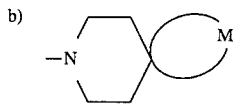 VIII
  c) 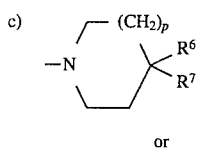 IX or d) 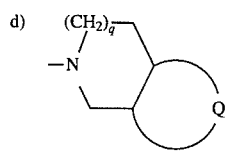 X M is a residue which combines with the carbon atom to which it is attached to complete an indanyl, indenyl, pyrrolidinyl, tetralinyl, benzopyranyl, dihydroindolyl, naphthodihydrofuranyl, benzodihydrothienyl, benzodihydrofuranyl, benzodihydropyranyl, naphthodihydrothienyl, or naphthodihydropyrrolyl group wherein the spiro junction is not to an aromatic ring,
  substituted with 0-2 $C_1$-$C_3$ alkyl, oxo, $C_1$-$C_3$ alkoxy, pyrrolidinyl- or piperidinyl-$C_1$-$C_3$ alkoxy, $C_1$-$C_2$ alkylenedioxy, phenoxy, benzyloxy, phenyl or halo groups;

p represents 0-2;

R⁶ and R⁷ independently represent phenyl groups,
  substituted with 0-2 $C_1$-$C_3$ alkyl, $C_1$-$C_3$ alkoxy or halo groups;

or R⁶ and R⁷ combine with the atom to which they are attached to complete a fluorenyl or dihydroanthracenyl group;

or R⁶ and R⁷ represent hydrogen, provided that p must not be 1;

q represents 0-2;

Q represents a residue which combines with the atoms to which it is attached to complete a phenyl or naphthyl group,
  substituted with 0-2 $C_1$-$C_3$ alkyl, $C_1$-$C_3$ alkoxy or halo groups;

R⁸ is hydrogen or $C_1$-$C_3$ alkyl;

or a pharmaceutically acceptable salt thereof.

Further, pharmaceutical methods of use combining activity at the $1_A$ receptor and inhibition of serotonin reuptake are carried out by the administration of compounds of the following formula.

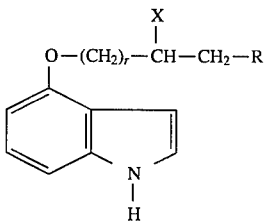

XIII wherein
r is 0-3;
X is hydrogen or hydroxy;
R is

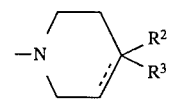

III

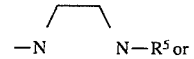

IV

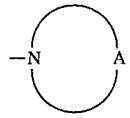

V the dotted line is an optional double bond;

R² is hydroxy or hydrogen, or is absent when the dotted line is a double bond;

R³ is $C_1$-$C_4$ alkyl,
  substituted with 1-2 phenyl groups,
    substituted with 0-2 halo groups;

or R³ is dibenzocycloheptenyl or benzodioxinyl;

or R³ is phenyl, benzothienyl, naphthyl, indolyl or piperidino,
  substituted with 0-2 $C_1$-$C_3$ alkoxy, hydroxy, $C_1$-$C_3$ alkyl, cyano, $C_4$-$C_8$ cycloalkylalkoxy, halo, nitro, trifluoromethyl or trifluoromethoxy groups;

or R² and R³ combine to form $C_1$-$C_4$ alkylidene,
  substituted with 1-2 phenyl groups, substituted with 0–2 halo groups;

$R^5$ is phenyl, phenyl-$C_1$–$C_3$ alkyl, or diphenyl-$C_1$–$C_3$ alkyl, substituted with 1–2 halo, $C_1$–$C_3$ alkoxy or trifluoromethyl groups;

A is a residue which combines with the nitrogen atom to which it is attached to complete

VIII

M is a residue which combines with the carbon atom to which it is attached to complete a benzopyranyl, naphthodihydrofuranyl, benzodihydrothienyl, or benzodihydrofuranyl group, wherein the spiro junction is not to an aromatic ring, substituted with 0–2 $C_1$–$C_3$ alkoxy, benzyloxy, phenyl or halo groups;

or a pharmaceutically acceptable salt thereof.

Still further, the invention provides a method of affecting the serotonin $1_A$ receptor which comprises administering to a subject in need of such treatment an effective amount of a compound of Formula XII. More specific methods of treatment include a method of alleviating the symptoms caused by withdrawal or partial withdrawal from the use of tobacco or of nicotine; a method of treating anxiety; and a method of treating a condition chosen from the group consisting of depression, hypertension, cognitive disorders, psychosis, sleep disorders, gastric motility disorders, sexual dysfunction, brain trauma, memory loss, eating disorders and obesity, substance abuse, obsessive-compulsive disease, panic disorder and migraine; which methods comprise administering to a subject in need of such treatment an effective amount of a compound of Formula XII. Further, the invention provides a method of alleviating the symptoms caused by withdrawal or partial withdrawal from the use of tobacco or of nicotine; and a method of potentiating the action of a serotonin reuptake inhibitor in increasing the availability of serotonin, norepinephrine and dopamine in the brain, comprising administering to a subject in need of such treatment a compound of Formula XII in combination with a serotonin reuptake inhibitor.

The invention also provides a method of inhibiting the reuptake of serotonin which comprises administering to a subject in need of such treatment an effective amount of a compound of Formula XIII; a method of inhibiting the reuptake of serotonin wherein the serotonin $1_A$ receptor of the subject is also affected is further provided by administering an effective amount of one of the same compounds.

Methods of treating depression and of treating both anxiety and depression are also provided by administering to a subject in need of such treatment an effective amount of a compound of Formula XIII.

Further, the administration of a compound of Formula XIII also provides a method of treating a condition chosen from the group consisting of obsessive-compulsive disease, obesity, migraine, pain, particularly neuropathic pain, bulimia, premenstrual syndrome or late luteal syndrome, alcoholism, tobacco abuse, panic disorder, anxiety, post-traumatic stress disorder, memory loss, dementia of aging, social phobia, attention-deficit hyperactivity disorder, disruptive behavior disorders, impulsive control disorders, borderline personality disorder, chronic fatigue syndrome, premature ejaculation, erectile difficulty, anorexia nervosa, disorders of sleep, autism, mutism and trichotilomania.

DESCRIPTION OF PREFERRED EMBODIMENTS

In the present document, all descriptions of concentrations, amounts, ratios and the like will be expressed in weight units unless otherwise stated. All temperatures are in degrees Celsius.

The Compounds

It is believed that the general description of the compounds above is sufficient to explain their nature to the skilled reader; attention to the Examples which follow is also encouraged. Some additional description will be provided to assure that no misunderstanding occurs.

In the general description, the general chemical terms are all used in their normal and customary meanings. For example, the small alkyl and alkoxy groups include, depending on the size of the groups, methyl, ethyl, propyl, isopropyl, n-butyl, s-butyl, t-butyl, pentyl, 3-methylbutyl, hexyl, and branched hexyl groups, and the corresponding alkoxy groups, as may be allowed by the individually named groups. Where a number of possible substituent groups are permitted on a group, such as the 0–4 alkyl, alkoxy or halo groups permitted on an $R^1$ morpholino group, it will be understood by the reader that only substitution which is chemically, electronically and sterically feasible is intended.

The term halo is used in the above formula to refer to fluoro, chloro, bromo or iodo.

Group D completes a bicyclic nitrogen-containing heterocycle which, most often, is indolyl, but may also be quinolinyl, isoquinolinyl, benzimidazolyl, quinazolinyl and the like.

The subscripts r and s indicate that as many as 7 methylene groups may be in the linker alkylene chain. Thus, the chain is straight-chain alkyl from ethyl through heptyl, which may be substituted with the group X as shown. The preferred groups are hydrogen and hydroxy.

The term $C_4$–$C_8$ cycloalkylalkoxy includes groups such as cyclopropylmethoxy, cyclohexylethoxy, cyclopentylmethoxy and the like.

In the above formula, the components of the compounds, for example, the group of Formula IV, are illustrated in a manner which shows the point of attachment to the basic structure. In Formula IV, for example, the attachment must be at the 1-position of the piperazinyl ring, and the substituent $R^5$ is at the 4-position.

The group of Formula III is a piperidine or tetrahydropyridine with the $R^2$ and $R^3$ groups at the 4-position, and an optional $R^8$ group at any other position of the ring. While the $R^3$ group may represent any of several definitions, the $R^2$ and $R^3$ groups are both relatively simple and the reader will readily understand the nature of them. It should be noted, however, that the novel compounds of the present invention do not include certain combinations of $R^2$ and $R^3$ substituents, as explained above in the Summary of the Invention.

It may be noted again that bulky $R^3$ groups such as dibenzocycloheptene or naphthyl may be linked in any reasonable orientation, as may substituent parts of the $R^3$ group such as piperazinonyl.

Where the orientation of a group is not stated, for example, a pyrrolyl group substituted on alkyl in the definition of $R^1$, it is intended that any reasonable orientation be used. The pyrrolyl group, thus, may be substituted at the 2- or 3-positions, and may itself be substituted at will with alkyl, alkoxy or halo groups. Again, there is no intent to describe unreasonable or impossible substituted groups.

The spiro-linked group of Formula VI represents structures of which the following are typical:

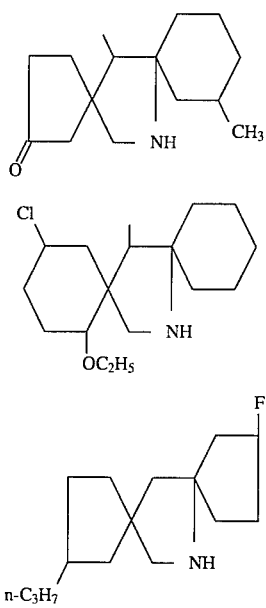

The fused aryl heterocyclic group of Formula VII represents, for example, the following structures.

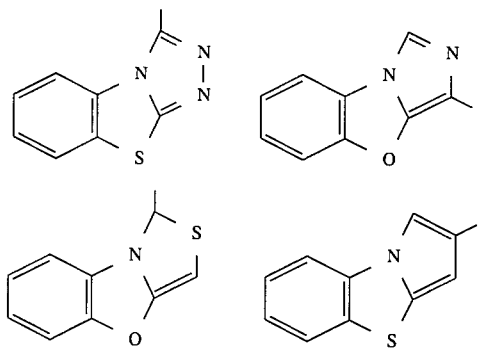

The group of Formula V has four definitions, of which the group of Formula VIII is preferred. Formula VIII represents a spiro structure wherein M represents the atoms necessary to complete one of the designated cyclic groups. Several of the M groups are multiple ring structures, such as naphthodihydropyrrolyl, wherein one or more of the rings is aromatic and one is not aromatic. The skilled reader will of course understand that the spiro junction necessarily is formed by a ring of the M group which is not aromatic. For example, the dihydropyrrolyl group in naphthodihydropyrrolyl must form the spiro junction.

The non-aromatic ring of such M groups may be oriented in any feasible manner that does not place the hetero atom at the spiro junction. Some nomenclatural schemes would describe a benzodihydrothienyl group as one where the sulfur atom is at the 1-position and would term it isodihydrobenzothienyl if the sulfur atom is at the 2-position. In the present document, however, all such compounds are termed benzodihydrothienyl, and the position of the sulfur atom is indicated by a number in the chemical name. The same principle of nomenclature is applied in naming all of the M groups. The examples below illustrate numerous typical M groups, and several of the complex, and especially the spiro, R groups are drawn in the examples to assure comprehension.

Where a cyclic structure is substituted with an oxo group, as for example a group of Formula VIII substituted with oxo, it will be understood that the oxo group may not occupy an aromatic ring of the cyclic structure. It will also be understood that such groups may form tautomeric structures, where the oxygen is in the hydroxy form and a double bond is formed within the cyclic structure.

The examples below show the synthesis of numerous compounds having a spiro M group. It will be seen that one group of preferred such compounds includes those where the spiro ring is dihydrofuran, frequently carrying an oxo group, and fused to a phenyl or naphthyl group. It will be understood that in each case the designation of a preferred compound here includes its pharmaceutically acceptable salts. Appropriate substituents on such compounds, particularly on the phenyl or naphthyl portion of the group, include alkoxy, benzyloxy and halo.

The spiro-fused group of Formula VIII represents groups such as the following. Again, it is intended that the heterocyclic groups formed by the group completed by M may be arranged in any feasible orientation, provided that an aromatic group may not form the spiro junction, and there is no intention to describe impossible groups or those which cannot be synthesized by the knowledgeable organic chemist.

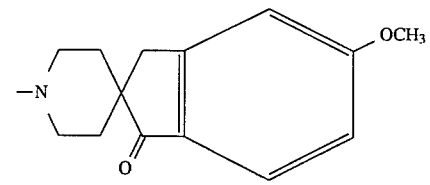

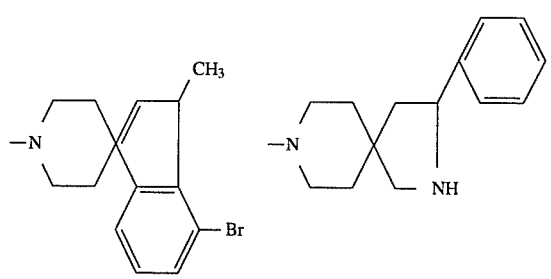

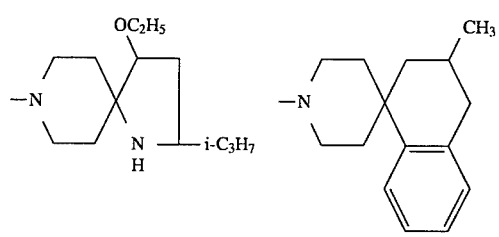

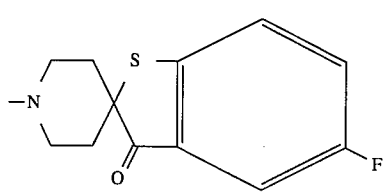

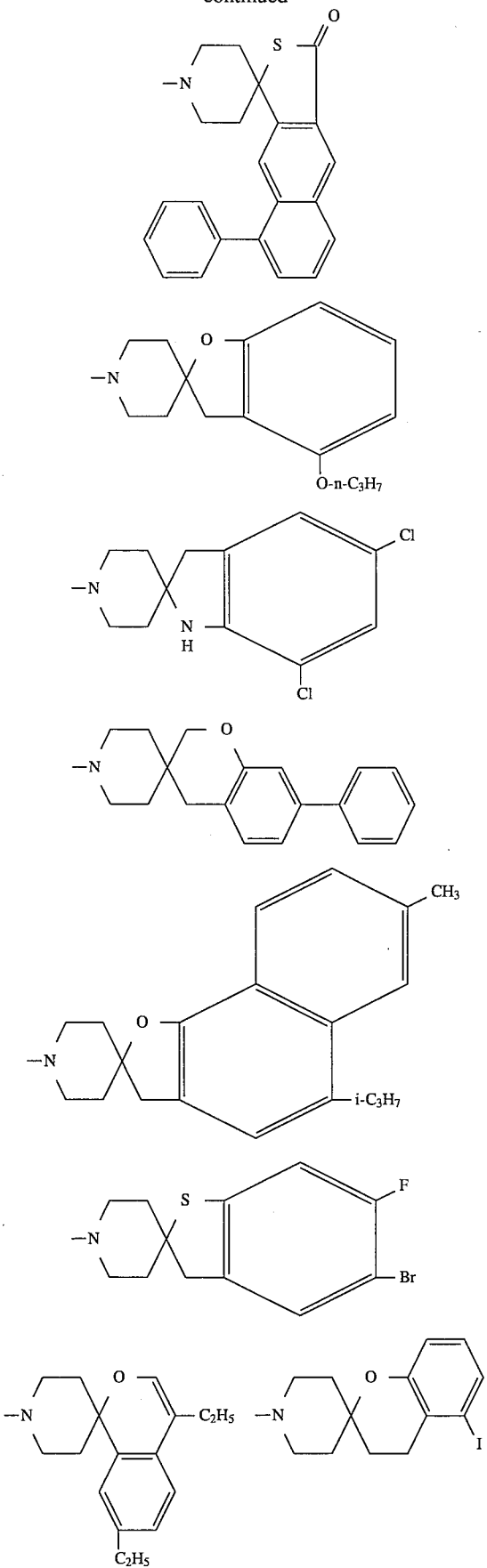
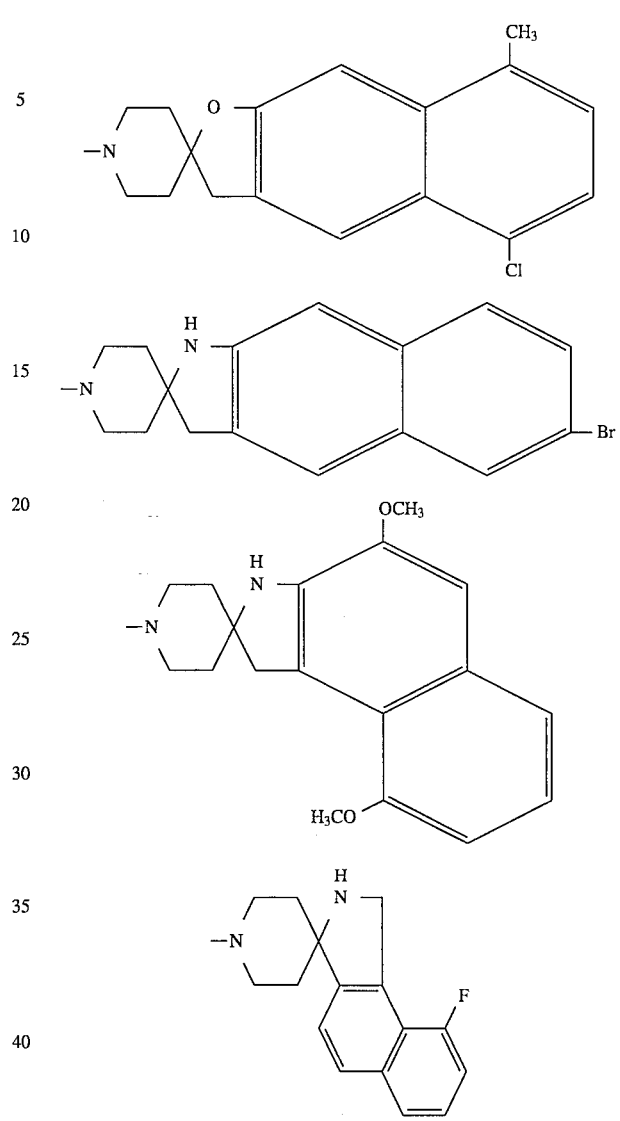

The group of Formula IX is a polymethyleneimino of from 4 to 6 methylene groups, having the $R^6$ and $R^7$ substituents on the same carbon atom. Those substituents may represent phenyl or substituted phenyl groups or hydrogen, or $R^6$ and $R^7$ may combine to form a spiro-linked fluorenyl or dihydro anthracenyl group.

The group of Formula X is a polymethylene group of 4 to 6 methylene groups, fused to a phenyl or naphthyl group.

The compounds of Formulae XI and XIII constitute a particular class of the compounds described in this document, which are unique in their dual activity as antagonists at the 5-$HT_1A$ receptor and inhibitors of serotonin reuptake. It will be seen that the dual activity compounds are enclosed within Formulae I and XII and are described in the same manner as are the broader groups of compounds. It will be noted that the compounds of Formula XIII include a class wherein the group R is a piperazine of Formula IV, which is not included within the compounds of Formula XI, and accordingly the $R^5$ group of Formula IV is also included in Formula XIII.

The compounds described in this document are highly active, important and particularly useful in the treatment methods of the present invention, but certain classes of the compounds are preferred. The following paragraphs describe such preferred classes. It will be understood that the preferred classes are applicable both to the treatment methods and to the new compounds of the present invention, except where a certain class is included only in a treatment method genus, and not in a definition of new compounds. It will be further understood that when a certain group is referred to as preferred, its allowable substitutions are also intended; for example, the preferred class, $R^1$ is $C_1$–$C_4$ alkyl substituted with adamantyl, is to be understood as including the possible alkyl, alkoxy or halo substitutions shown in the general formula.

The first group of preferred classes of compounds is applicable to the compounds of Formulae XI and XIII.

1) r is 1–2;
2) r is 1;
3) X is hydrogen;
4) X is hydroxy;
5) R is of Formula III;
6) R is of Formula IV;
7) R is of Formula V;
8) the dotted line does not represent a double bond and $R^2$ is hydrogen;
9) $R^3$ is $C_1$–$C_2$ alkyl substituted with 1–2 phenyl groups;
10) $R^3$ is phenyl or naphthyl;
11) $R^3$ is benzothienyl or indolyl;
12) $R^3$ is piperidino;
13) $R^3$ is benzothienyl substituted with 1–2 $C_1$–$C_3$ alkoxy, $C_1$–$C_3$ alkyl, $C_4$–$C_8$ cycloalkylalkoxy, halo, nitro, trifluoromethyl or trifluoromethoxy groups;
14) $R^3$ is indolyl substituted with 1–2 $C_1$–$C_3$ alkoxy, $C_1$–$C_3$ alkyl, $C_4$–$C_8$ cycloalkylalkoxy, halo, nitro, trifluoromethyl or trifluoromethoxy groups;
15) M completes a benzopyranyl group;
16) M completes a naphthodihydrofuranyl group;
17) M completes a benzodihydrothienyl group;
18) M completes a benzodihydrofuranyl group;
19) the group completed by M is substituted with 1–2 alkoxy or benzyloxy groups;
20) the group completed by M is substituted with 1–2 phenyl groups;
21) the group completed by M is substituted with 1–2 alkoxy, benzyloxy or halo groups;
22) $R^5$ is phenyl;
23) $R^5$ is phenyl-$C_1$–$C_3$ alkyl;
24) the group completed by M is diphenyl-$C_1$–$C_3$ alkyl;
25) the compound is a pharmaceutically acceptable salt.

The following preferred definitions apply to the compounds of Formulae I and XII.

a) X is hydroxy;
b) X is hydrogen;
c) $R^1$ is piperidinyl, piperazino, morpholino or pyrrolyl;
d) $R^1$ is adamantyl;
e) $R^1$ is a group of Formula VI;
f) $R^1$ is $C_1$–$C_2$ alkyl substituted with pyrrolyl, adamantyl, furyl, thienyl, pyridinyl, morpholinyl, piperidinyl, tetrahydropyrrolyl, piperazinyl, tetrahydrofuryl, benzazepinyl, dibenzazepinyl or quinolinyl;
g) $R^1$ is $C_1$–$C_4$ alkyl substituted with adamantyl;
h) $R^1$ is $C_1$–$C_4$ alkyl substituted with pyrrolyl, furyl, thienyl, benzazepinyl or dibenzazepinyl;
i) $R^1$ is $C_1$–$C_4$ alkyl substituted with pyridinyl, morpholinyl, piperidinyl, tetrahydropyrrolyl, piperazinyl, tetrahydrofuryl or quinolinyl;
j) $R^2$ is hydroxy or hydrogen;
k) $R^2$ is cyano, alkyl, or (phenyl or benzyl substituted with 0–2 alkyl, alkoxy or halo groups);
l) $R^2$ is hydroxy;
m) $R^3$ is alkyl substituted with phenyl;
n) $R^3$ is phenoxy;
o) $R^3$ is phenyl;
p) $R^3$ is naphthyl or piperidino;
q) $R^3$ is phenyl, substituted with alkyl, alkoxy, alkylenedioxy, halo, trifluoromethyl or trifluoromethoxy;
r) $R^5$ is alkyl;
s) $R^5$ is alkyl substituted with benzodioxinyl, phenyl or benzodioxolyl;
t) $R^5$ is pyridinyl, pyrimidinyl, pyrazinyl, quinolinyl, isoquinolinyl, phenyl, pyridazinyl or quinazolinyl;
u) $R^5$ is pyridinyl, pyrimidinyl, pyrazinyl, quinolinyl, isoquinolinyl, pyridazinyl or quinazolinyl;
v) R is a group of Formula II;
w) R is a group of Formula III;
x) R is a group of Formula IV;
y) R is a group of Formula V;
z) $R^5$ is a group of Formula VII;
aa) A is a group of Formula VIII;
ab) A is a group of Formula IX;
ac) A is a group of Formula X;
ad) M completes a benzopyranyl, benzodihydropyranyl, naphthodihydrofuranyl or benzodihydrofuranyl group;
ae) M completes a benzodihydrothienyl or naphthodihydrothienyl group;
af) M completes a pyrrolidinyl, dihydroindolyl, or naphthodihydropyrrolyl group;
ag) M completes an indanyl, indenyl, or tetralinyl group;
ah) the compound is a salt;
ai) halo is chloro, bromo or fluoro;
aj) the dotted line does not represent a double bond and $R^2$ is present;
ak) D completes a pyrrolyl group;
al) D completes an imidazolyl group;
am) D completes a pyridinyl group;
an) D completes a pyrazinyl, pyridazinyl or pyrimidinyl group;
ao) r is 1–3;
ap) r is 1;
aq) X is hydrogen, hydroxy or methoxy;
ar) X is hydrogen or hydroxy;
as) $R^1$ is tetralinyl or naphthyl;
at) $R^3$ is benzodioxolyl or benzodioxinyl;
au) $R^3$ is naphthyl or tetralinyl;
av) $R^3$ is tetrazolyl or benzimidazolyl;
aw) $R^3$ is indolyl, benzofuryl or benzothienyl;
ax) $R^3$ is indolyl substituted with 1–2 alkyl, alkoxy, cycloalkylalkoxy, halo, nitro, trifluoromethyl, difluoromethyl, hydroxy or trifluoromethoxy groups;
ay) $R^3$ is benzothienyl substituted with 1–2 alkyl, alkoxy, cycloalkylalkoxy, halo, nitro, trifluoromethyl, difluoromethyl, hydroxy or trifluoromethoxy groups;
az) $R^5$ is naphthyl or tetralinyl;
ba) $R^5$ is indolyl;
bb) $R^5$ is benzofuryl or benzothienyl;

bc) $R^5$ is quinolinyl or isoquinolinyl;

bd) the group completed by M is substituted with 0–2 alkyl, oxo, alkoxy, phenyl or halo groups;

be) the group completed by M is substituted with 0–2 alkoxy, phenoxy or benzyloxy groups;

bf) the group completed by M is substituted with pyrrolidinyl- or piperidinyl-$C_1$–$C_3$ alkoxy groups;

bg) s is 0.

Further, a preferred class of compounds of Formula I includes the following subgenus.

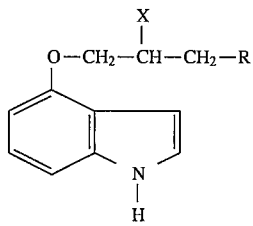

wherein X is hydrogen, hydroxy or methoxy; R is $-NH-R^1$,     II

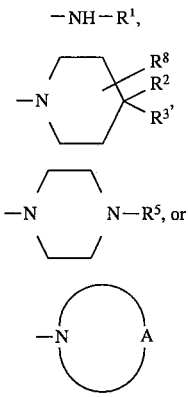

$R^1$ is piperidinyl, piperazino, morpholino or pyrrolyl,
   substituted with 0–1 benzyl group or 0–4 $C_1$–$C_3$ alkyl, $C_1$–$C_3$ alkoxy or halo groups;

or $R^1$ is

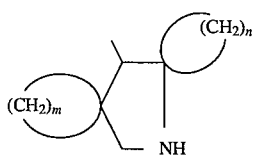

n and m are independently 4–5, and the group of Formula VI may be substituted with 0–1 oxo group and 0–2 $C_1$–$C_3$ alkyl, $C_1$–$C_3$ alkoxy or halo groups;

or $R^1$ is $C_1$–$C_4$ alkyl,
   substituted with pyrrolyl, furyl, thienyl, pyridinyl, morpholinyl, piperidinyl, tetrahydropyrrolyl, piperazinyl, tetrahydrofuryl, benzazepinyl, dibenzazepinyl or quinolinyl,
      substituted with 0–4 $C_1$–$C_3$ alkyl, $C_1$–$C_3$ alkoxy or halo groups;

$R^2$ is hydroxy, hydrogen, cyano, $C_1$–$C_4$ alkyl, or (phenyl or benzyl substituted with 0–2 $C_1$–$C_3$ alkyl, $C_1$–$C_3$ alkoxy or halo groups);

$R^3$ is $C_1$–$C_4$ alkyl,
   substituted with 0–2 phenyl groups,
      substituted with 0–2 $C_1$–$C_3$ alkyl, $C_1$–$C_3$ alkoxy or halo groups;

or $R^3$ is phenoxy,
   substituted with 0–1 methylenedioxy or substituted with 0–2 $C_1$–$C_3$ alkyl, $C_1$–$C_3$ alkoxy, trifluoromethyl or halo groups;

or $R^3$ is dibenzocycloheptene or dibenzocyclohexene;

or $R^3$ is phenyl, naphthyl, piperidino or morpholino,
   substituted with 0–2 $C_1$–$C_3$ alkyl, $C_1$–$C_3$ alkoxy, halo, $C_1$–$C_2$ alkylenedioxy, trifluoromethyl, hydroxy or trifluoromethoxy groups;
   or substituted with 0–1 phenyl, piperidinonyl, hexahydropyridazinonyl or piperazinonyl group,
      substituted with 0–2 $C_1$–$C_3$ alkyl, oxo, $C_1$–$C_3$ alkoxy, halo or trifluoromethyl groups;

provided that $R^3$ is not halo- or trifluoromethyl-substituted phenyl when $R^2$ is hydroxy;

$R^5$ is $C_1$–$C_6$ alkyl or $C_1$–$C_4$ acyl;

or $R^5$ is $C_1$–$C_3$ alkyl substituted with benzodioxinyl or benzodioxolyl,
   substituted on the phenyl ring with 0–2 $C_1$–$C_3$ alkyl, $C_1$–$C_3$ alkoxy or halo groups;

or $R^5$ is pyridinyl, pyrimidinyl, pyrazinyl, quinolinyl, isoquinolinyl, pyridazinyl or quinazolinyl,
   substituted with 0–2 $C_1$–$C_3$ alkyl, trifluoromethyl, $C_1$–$C_3$ alkoxy or halo groups;

or $R^5$ is

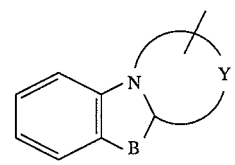

B is oxygen or sulfur;

Y is a residue which combines with the atoms to which it is attached to complete a triazolyl, imidazolyl, thiazolyl or pyrrolyl ring;

A is a residue which combines with the nitrogen atom to which it is attached to complete
   a) an azabicyclo(octyl, nonyl or decyl) group;

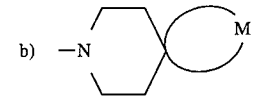

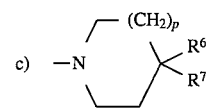

or

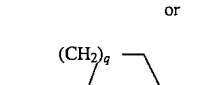

M is a residue which combines with the carbon atom to which it is attached to complete an indanyl, indenyl, pyrrolidinyl, tetralinyl, benzopyranyl, dihydroindolyl, naphthodihydrofuranyl, benzodihydrothienyl, benzodihydrofuranyl, benzodihydropyranyl, naphthodihydrothienyl, or naphthodihydropyrrolyl group wherein the spiro junction is not to an aromatic ring,
   substituted with 0–2 $C_1$–$C_3$ alkyl, oxo, $C_1$–$C_3$ alkoxy, phenyl or halo groups;

p represents 0–2;

R[6] and R[7] independently represent phenyl groups,
    substituted with 0–2 $C_1$–$C_3$ alkyl, $C_1$–$C_3$ alkoxy or halo groups;
or R[6] and R[7] combine with the atom to which they are attached to complete a fluorenyl or dihydroanthracenyl group;
or R[6] and R[7] represent hydrogen, provided that p must not be 1;
q represents 0–2;
Q represents a residue which combines with the atoms to which it is attached to complete a phenyl or naphthyl group,
    substituted with 0–2 $C_1$–$C_3$ alkyl, $C_1$–$C_3$ alkoxy or halo groups;
R[8] is hydrogen or $C_1$–$C_3$ alkyl;
or a pharmaceutically acceptable salt thereof.

Another preferred aspect of the invention includes methods of use of the compounds of Formula XII described by the following subgenus.

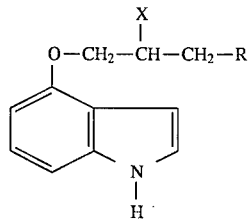

wherein X is hydrogen, hydroxy or methoxy; R is

    II

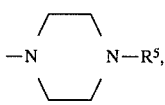    III

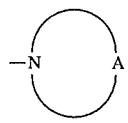    IV or

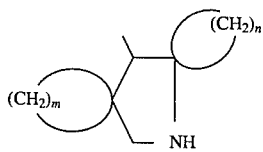    V

R[1] is piperidinyl, adamantyl, piperazino, morpholino or pyrrolyl,
    substituted with 0–1 benzyl group or 0–4 $C_1$–$C_3$ alkyl, $C_1$–$C_3$ alkoxy or halo groups;
or R[1] is

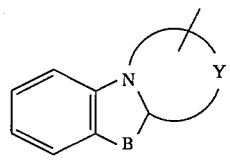    VI n and m are independently 4–5, and the group of Formula VI may be substituted with 0–1 oxo group and 0–2 $C_1$–$C_3$ alkyl, $C_1$–$C_3$ alkoxy or halo groups;
or R[1] is $C_1$–$C_4$ alkyl,
    substituted with pyrrolyl, adamantyl, furyl, thienyl, pyridinyl, morpholinyl, piperidinyl, tetrahydropyrrolyl, piperazinyl, tetrahydrofuryl, benzazepinyl, dibenzazepinyl or quinolinyl,
    substituted with 0–4 $C_1$–$C_3$ alkyl, $C_1$–$C_3$ alkoxy or halo groups;
R[2] is hydroxy, hydrogen, cyano, $C_1$–$C_4$ alkyl, or (phenyl or benzyl substituted with 0–2 $C_1$–$C_3$ alkyl, $C_1$–$C_3$ alkoxy or halo groups);
R[3] is $C_1$–$C_4$ alkyl,
    substituted with 0–2 phenyl groups,
        substituted with 0–2 $C_1$–$C_3$ alkyl, $C_1$–$C_3$ alkoxy or halo groups;
or R is benzimidazolyl or indolyl,
    substituted with 0–2 phenyl, oxo, $C_1$–$C_3$ alkyl, $C_1$–$C_3$ alkoxy or halo groups;
or R[3] is phenoxy,
    substituted with 0–1 methylenedioxy or substituted with 0–2 $C_1$–$C_3$ alkyl, $C_1$–$C_3$ alkoxy, trifluoromethyl or halo groups;
or R[3] is dibenzocycloheptene or dibenzocyclohexene;
or R[3] is phenyl, naphthyl, piperidino or morpholino,
    substituted with 0–2 $C_1$–$C_3$ alkyl, $C_1$–$C_3$ alkoxy, halo, $C_1$–$C_2$ alkylenedioxy, trifluoromethyl, hydroxy or trifluoromethoxy groups;
    or substituted with 0–1 phenyl, piperidinonyl, hexahydropyridazinonyl or piperazinonyl group,
        substituted with 0–2 $C_1$–$C_3$ alkyl, oxo, $C_1$–$C_3$ alkoxy, halo or trifluoromethyl groups;
R[5] is $C_1$–$C_6$ alkyl or $C_1$–$C_4$ acyl;
or R[5] is $C_1$–$C_3$ alkyl substituted with benzodioxinyl, phenyl or benzodioxolyl,
    substituted on the phenyl ring with 0–2 $C_1$–$C_3$ alkyl, $C_1$–$C_3$ alkoxy or halo groups;
or R[5] is pyridinyl, pyrimidinyl, pyrazinyl, quinolinyl, isoquinolinyl, phenyl, pyridazinyl or quinazolinyl,
    substituted with 0–2 $C_1$–$C_3$ alkyl, trifluoromethyl, $C_1$–$C_3$ alkoxy or halo groups;
or R[5] is

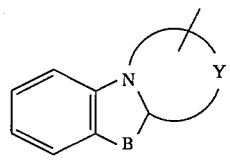    VII

B is oxygen or sulfur;
Y is a residue which combines with the atoms to which it is attached to complete a triazolyl, imidazolyl, thiazolyl or pyrrolyl ring;
A is a residue which combines with the nitrogen atom to which it is attached to complete
a) an azabicyclo(octyl, nonyl or decyl) group;

    VIII

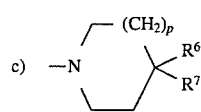    IX or d) 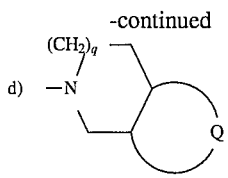

M is a residue which combines with the carbon atom to which it is attached to complete an indanyl, indenyl, pyrrolidinyl, tetralinyl, benzopyranyl, dihydroindolyl, naphthodihydrofuranyl, benzodihydrothienyl, benzodihydrofuranyl, benzodihydropyranyl, naphthodihydrothienyl, or naphthodihydropyrrolyl group wherein the spiro junction is not to an aromatic ring, substituted with 0–2 $C_1$–$C_3$ alkyl, oxo, $C_1$–$C_3$ alkoxy, phenyl or halo groups;

p represents 0–2;

$R^6$ and $R^7$ independently represent phenyl groups, substituted with 0–2 $C_1$–$C_3$ alkyl, $C_1$–$C_3$ alkoxy or halo groups;

or $R^6$ and $R^7$ combine with the atom to which they are attached to complete a fluorenyl or dihydroanthracenyl group;

or $R^6$ and $R^7$ represent hydrogen, provided that p must not be 1;

q represents 0–2;

Q represents a residue which combines with the atoms to which it is attached to complete a phenyl or naphthyl group, substituted with 0–2 $C_1$–$C_3$ alkyl, $C_1$–$C_3$ alkoxy or halo groups;

$R^8$ is hydrogen or $C_1$–$C_3$ alkyl;

or a pharmaceutically acceptable salt thereof.

The above compounds are used in methods of affecting, particularly methods of antagonizing, the 5HT-$1_A$ receptor, and therapeutic methods which are related to their effect on the 5HT-$1_A$ receptor. Such methods of treatment include, particularly, methods of alleviating the symptoms caused by withdrawal or partial withdrawal from the use of tobacco or of nicotine, comprising the administration to a patient in need of such treatment of a compound of Formula I.

Further, such therapeutic methods include methods of treatment of anxiety, depression, hypertension, cognitive disorders, psychosis, sleep disorders, gastric motility disorders, sexual dysfunction, brain trauma, memory loss, eating disorders and obesity, substance abuse, obsessive-compulsive disease, panic disorder and migraine. A further such method is the enhancement of the action of a serotonin reuptake inhibitor by administering a compound of the above subgenus in combination with the reuptake inhibitor.

The reader will understand that the above preferred classes of compounds may be combined to form additional, broader or narrower classes of preferred compounds.

Certain compounds of the present invention are particularly active or selective, and are accordingly even more highly preferred than other compounds and classes of compounds. The most highly preferred compounds for use in creating desired effects at the 5-$HT_1$A receptor are the compounds of Examples 63, 71, 78, 79, 82, 88, 94, 126 and 189 in the section immediately following. The most highly preferred compounds with dual activity at the $1_A$ receptor and also as serotonin reuptake inhibitors, include the compounds of Examples 64, 89, 193, 197, 196, 205, 154 and 151.

Since the compounds of this invention are basic in nature, they accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, subcrate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid or maleic acid.

Many of the compounds of Formula I can form optical isomers. In particular, the compounds wherein X is hydroxy or methoxy have an asymmetric center at the carbon atom to which X is attached. Further, many of the R groups can exist in multiple optical forms. In general, it is preferred for the asymmetric center to which X is attached to exist in the S-(–) form. However, when a compound of the present invention is named without an indication of asymmetric form, any and all of the possible asymmetric forms are intended.

Synthesis

The synthesis of the present compounds is carried out by methods which are conventional for the synthesis of related known compounds. The syntheses, in general, comprise the reaction of one intermediate which supplies the Het-oxypropane group with an intermediate which supplies the amine group R. The term Het will be used here to refer briefly to the group

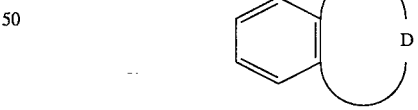

When a compound where X is hydroxy is to be prepared, the most useful intermediate is 4-oxiranylalkoxy-Het, which is readily reacted with the amine compound which provides the R group. The oxiranyl intermediate is readily prepared by known methods as the racemate or either enantiomer. When a compound where R is of Formula II is to be prepared, the reactant is a simple amine, such as adamantylamine; when a more complex group is to be prepared, the oxiranyl group readily reacts with the nitrogen of the appropriate heterocycle to prepare the desired product in good yield. Moderate reaction conditions, such as from ambient temperature to about 100°, are satisfactory, and any solvent which is inert to the reactants and has adequate solvency for them may be used. It has been found that a preferred reaction condition is the reflux temperature at ambient pressure in an alcohol such as methanol. No catalyst or activating agent is necessary, and conventional isolation procedures are effective. The examples below illustrate the synthesis of many compounds of the present invention by such processes. When the process is carried out with intermediates in a single asymmetric form, little or no racemization has been observed, so that the products are obtained in the desired single asymmetric form.

Another convenient method of synthesis of the present compounds is by use of a 1-chloro(Het-oxy)alkane, which may optionally be substituted with a phenyl, hydroxy or methoxy group. Alternatively, other leaving groups besides chloro may be used on the Het-oxyalkane, of course, such as sulfonates, particularly methane-sulfonate or toluene-sulfonate, bromo, and the like. The Het-oxyalkane intermediate is reacted with the amine-containing intermediate which provides the R group, in the presence of any convenient acid scavenger. The usual bases such as alkali metal or alkaline earth metal carbonates, bicarbonates and hydroxides are useful acid scavengers, as are some organic bases such as trialkylamines and trialkanolamines. The reaction medium for such reactions may be any convenient organic solvent which is inert to the basic conditions; acetonitrile, esters such as ethyl acetate and the like and halogenated alkane solvents are useful, as organic chemists will readily understand. Usually the reactions will be carried out at elevated temperatures such as from ambient temperature to the reflux temperature of the reaction mixture, particularly from about 50° to about 100°.

Methods of synthesis of the Her intermediates are found in the literature, together with methods of preparing the isolated enantiomers thereof, and the reader will require no assistance to obtain them.

Intermediates where X is methoxy, (Het-oxy)methoxyalkanes, are best prepared from a dimethyl methoxyalkanedioic acid, which is first treated with lithium aluminum hydride to obtain, after quenching of excess reagent, a dihydroxymethoxyalkane. That intermediate is converted to the ditosylate, which is reacted with hydroxy-Het to prepare the desired intermediate having a tosyl protecting group at the terminus of the alkane. Reaction with the intermediate providing the R group is carried out as usual with that intermediate.

Similarly, the intermediates which provide the amine-containing R groups are all prepared by conventional procedures which may be found in the literature. Particular mention will be made of the spiro groups of Formula V where A is of Formula VIII, which are somewhat unusual. Methods for their preparation are found in the literature, and the following articles are pointed out as useful.

Marxer, et al., *J. Org. Chem.*, 40, 1427–1433, (1975)

Parham, et al., *J. Org. Chem.*, 41, 2628–2635, (1976)

Yamato, et al., *J. Med. Chem.*, 24, 194–198, (1981)

Evans, et al., *J. Med. Chem.*, 35, 3919–3927, (1992)

Efange, et al., *J. Med. Chem.*, 37, 2574–2582, (1994)

Chambers, et al., *J. Med. Chem.*, 35, 2033–2039, (1992)

The spiropiperidine intermediates are prepared, in general, by reaction of a 4-piperidinone or a piperidine having an activated group at the 4-position with a reagent which can attack the 4-position of the piperidine and form the necessary cyclic structure. For example, when the group attached spiro to the piperidine is a dihydrofuran ring, the starting material is an N-alkylated-4-piperidinone, which is reacted with an N,N-disubstituted benzamide or naphthylamide, carrying the desired substituents on the phenyl or naphthyl rings. The amide is first reacted with an alkyllithium reagent to form the metallated derivative. Reaction of that derivative with the piperidinone results in attack at the ketone of the piperidinone. A second step of quenching with a proton source, particularly with a dilute mineral acid, cyclizes the dihydrofuran ring, leaving it with an oxo group appended. The product may be reduced, as by treatment with a borane, if desired, and the nitrogen of the piperidine is dealkylated with excess 1-chloroethylchloroformate. The spiro intermediate is then reacted directly with the indole intermediate.

When the group joining the piperidine is a dihydrothienyl group, the process for synthesis is similar, but the starting material is a phenyl or naphthyl compound having a 1-mercaptomethyl group. A bromine or other strong leaving group is ortho to the mercaptomethyl group. Reaction with the piperidinone, followed by quenching with either a Lewis or protic acid, produces the desired benzodihydrothienyl or naphthodihydrothienyl spiro group. The process for preparing pyran and dihydropyran spiro groups proceeds substantially the same, but starting with a compound having a 1-hydroxymethyl rather than a 1-mercaptomethyl group.

Substituents on the spiropiperidine groups of Formula VIII, if not originating with the phenyl or naphthyl starting material, may be placed in later steps according to conventional processes.

Spiro compounds of Formula VIII which comprise an indanyl, indenyl or tetralinyl group are prepared directly from the corresponding indane, indene or tetralin which is activated at the desired point of attachment by formation of a salt, by treatment with a strong base such as potassium hexamethyldisilylamide, which is reacted with di(2-chloroethyl)amine, carrying a protecting group such as t-butoxycarbonyl on the nitrogen. The desired spiropiperidine is produced in a single step, but retaining the protecting group on the nitrogen of the piperidine. Deprotection by conventional means produces the desired intermediate.

Similarly, spiro intermediates having a pyrrolidinyl, dihydroindolinyl or naphthodihydropyrrolyl group are made by reacting a 2-oxopyrrolidine having a protecting group on the nitrogen, such as t-butoxycarbonyl, with protected di(2-chloroethyl)amine. The desired spiropiperidine, with an oxo group on the 5-membered ring and the protecting group on the piperidine nitrogen is obtained. Deprotection is conventional, and the oxo may be reduced, if desired, with lithium aluminum hydride or another conventional agent. The following Preparations illustrate the synthesis of such intermediates further.

The important group of compounds where R is a piperidine or tetrahydropyridine of Formula III, and $R^3$ is a cyclic group such as naphthyl or indole, are readily prepared by first making the R group complete, protecting the nitrogen of the piperidine or tetrahydropyridine as necessary during the synthesis, and reacting it with either an oxiranyl intermediate, or an alkoxy-Het bearing a chloro atom or other leaving group, as described above.

Thus, the general process for preparing the present compounds has two main variations, which may briefly be described as follows:

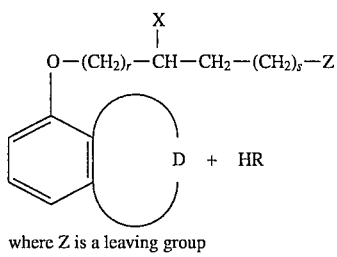

where Z is a leaving group

↓ compounds of Formula I, XI, XII and XIII

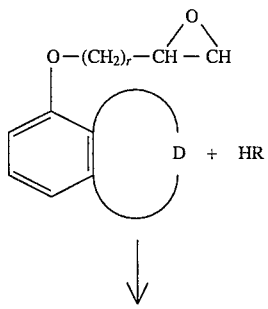

↓ compounds of Formula I, XI, XII and XIII,
where s is O and X is hydroxy

It is believed that all chemical names used here are unambiguous. However, drawings of the various complex R groups are given with the example in which each exemplified complex structure appears for the first time.

In the following Examples and Preparations, the abbreviation FDMS means field desorption mass spectroscopy.

The first group of Preparations illustrates typical syntheses of spiropiperidine intermediates used for preparing compounds where R is of Formula V and A is of Formula VIII.

Preparation 1

Preparation of 4-methoxyspiro[benzodihydrofuran-1(3H),4'-piperidin]-3-one

A three-neck flask was charged with 2-methoxy-N,N-diethylbenzamide (11.45 g., 55.3 mmol), 90 mL tetrahydrofuran (THF) and N,N,N',N'-tetramethylethylenediamine (TMEDA) (1.0 equivalent). The mixture was cooled to −78° C., and s-butyllithium (1.5 equiv. of a 1.3M solution in cyclohexane) was added dropwise, and the mixture was stirred for one hour. A solution of 1-methyl-4-piperidone (6.57 g. 1 equiv.) in 45 mL of THF was slowly added, at low temperature. The cooling bath was removed, and the mixture allowed to stir, at room temperature, for 12 h. 5N hydrochloric acid (60 mL) was added, and the aqueous and organic layers were separated. The organic layer was washed again with 1N hydrochloric acid, the aqueous layers were combined and treated with saturated aqueous ammonium hydroxide solution, and extracted into chloroform. The organic layer was washed with brine, and dried over sodium sulfate. The mixture was concentrated and purified by silica gel column chromatography (2–5% methanol in dichloromethane eluent gradient) to provide the N-methylated derivative of the title compound. It was dissolved in 1,2-dichloroethane, cooled to 0° C., and treated with excess 1-chloroethylchloroformate, allowed to warm to room temperature, and then heated at reflux for 12 hours. The mixture was cooled to 0° C. and concentrated in solution, methanol (50 mL) was added, and heating was continued for 3.5 additional hours, after which time the mixture was cooled to room temperature, diluted with water, treated with saturated aqueous ammonium hydroxide solution, and extracted into chloroform. The organic layer was separated, washed with brine, dried over sodium sulfate, concentrated, and purified by silica gel column chromatography (2% methanol in dichloromethane) to give 4.5 g (31% yield over two steps) of the title compound as a waxy solid. FDMS (m/e=233).

Preparation 2

Preparation of 4-methoxyspiro[benzodihydrofuran-1(3H),4'-piperidine]

A three-neck flask was charged with 2-methoxy-N,N-diethylbenzamide (11.45 g., 55.3 mmol), 90 mL tetrahydrofuran (THF) and N,N,N',N'-tetramethylethylenediamine (TMEDA) (1.0 equivalent). The mixture was cooled to −78° C., and s-butyllithium (1.5 equiv. of a 1.3M solution in cyclohexane) was added dropwise, and the mixture was stirred for one hour. A solution of 1-methyl-4-piperidone (6.57 g. 1 equiv.) in 45 mL of THF was slowly added, at low temperature. The cooling bath was removed, and the mixture allowed to stir, at room temperature, for 12 h. 5N hydrochloric acid (60 mL) was added, and the aqueous and organic layers were separated. The organic layer was washed again with 1N hydrochloric acid, the aqueous layers were combined and treated with saturated aqueous ammonium hydroxide solution, and extracted into chloroform. The organic layer was washed with brine, and dried over sodium sulfate. The mixture was concentrated and purified by silica gel column chromatography (2–5% methanol in dichloromethane eluent gradient) to provide the N-methyl-3-keto derivative of the title compound, which was dissolved in 70 mL of anhydrous tetrahydrofuran, cooled to 0° C., and treated with 2.5 equivalents of borane (1M solution in THF). The mixture was allowed to warm to room temperature, and was then heated at reflux for 12 hours. The mixture was cooled to 0° C., 5N hydrochloric acid (14 mL) was added to the cooled mixture, and heating at reflux was then continued for an additional 5 hours. The mixture was cooled, concentrated, and partitioned between water and diethyl ether. The organic phase was separated, and the aqueous phase was treated with concentrated ammonium hydroxide solution, and extracted with ether. The combined organic layer was washed with brine, dried over sodium sulfate and purified by silica gel column chromatography (2% methanol in dichloromethane eluent) to give the N-methylated derivative of the title compound, which was dissolved in 1,2-dichloroethane, cooled to 0° C., and treated with excess 1-chloroethylchloroformate, allowed to warm to room temperature, and then heated at reflux for 12 hours. To the mixture was added methanol (50 mL) and heating was continued for 3.5 additional hours, after which time the mixture was cooled to room temperature, diluted with water, treated with saturated acqueous ammonium hydroxide solution, and extracted into chloroform. The organic layer was separated, washed with brine, dried over sodium sulfate, concentrated, and purified by silica gel column chromatography (2% methanol in dichloromethane) to give 2.25 g (19% yield over three steps) of the title compound as a waxy solid. FDMS (m/e=219).

Preparations 3–18

The following derivatives were prepared in similar fashion as in Preparations 1 and 2, by starting with the appropriately substituted N,N-diethylbenzamide or naphthylamide derivative:

4-chlorospiro[benzodihydrofuran-1(3H),4'-piperidin]-3-one: 18% yield, FDMS (m/e=237).
6-chlorospiro[benzodihydrofuran-1(3H),4'-piperidin]-3-one: 17% yield, FDMS (m/e=237).
benzo[e]spiro[benzodihydrofuran-1(3H),4'-piperidin]-3-one: 30% yield, FDMS (m/e=253).
benzo[e]spiro[benzodihydrofuran-1(3H),4'-piperidin]: 14% yield, FDMS (m/e=239).
benzo[c]spiro[benzodihydrofuran-1(3H),4'-piperidin]-3-one: 60% yield, FDMS (m/e=253).
benzo[c]spiro[benzodihydrofuran-1(3H),4'-piperidin]: 20% yield, FDMS (m/e=239).
6-methylspiro[benzodihydrofuran-1(3H),4'-piperidin]-3-one: 13% yield, FDMS (m/e=217).
6-methylspiro[benzodihydrofuran-1(3H),4'-piperidin]: 9% yield, FDMS (m/e=203).
5-chlorospiro[benzodihydrofuran-1(3H),4'-piperidin]-3-one: 19% yield, FDMS (m/e=237).
5-chlorospiro[benzodihydrofuran-1(3H),4'-piperidin]: 12% yield, FDMS (m/e=223).
6-methoxyspiro[benzodihydrofuran-1(3H),4'-piperidin]-3-one: 19% yield, FDMS (m/e=233).
6-methoxyspiro[benzodihydrofuran-1(3H),4'-piperidin]: 15% yield, FDMS (m/e=219).
5-methoxyspiro[benzodihydrofuran-1(3H),4'-piperidin]: 31% yield, FDMS (m/e=219). 4-fluorospiro[benzodihydrofuran-1(3H),4'-piperidin]-3-one: 23% yield, FDMS (m/e=221). 4-benzyloxyspiro[benzodihydrofuran-1(3H),4'-piperidin]-3-one: 30% yield, FDMS (m/e=309).
6-benzyloxyspiro[benzodihydrofuran-1(3H),4'-piperidin]-3-one: 10% yield, FDMS (m/e=309).

EXAMPLE 1

Preparation of (2S)-(−)-1-(4-indolyloxy)-3-(4-[1-benzyl]piperidinylamino)-2-propanol A solution of (S)-(+)-4-(oxiranylmethoxy)-1H-indole (400 mg, 2.1 mmol) and 4-amino-1-benzylpiperidine (443 mg, 2.1 mmol) in 10 mL of methanol was heated at reflux for 18 h. The solution was cooled, concentrated and purified by silica gel chromatography (dichloromethane—5% methanol in dichloromethane solvent gradient) to give 618 mg (78%) of the title compound as an amorphous solid. FDMS m/e=379 ($M^+$ of free base). $\alpha[D]_{589}$=−8.90 (c=0.52, chloroform).

| analysis | calculated | found |
| --- | --- | --- |
| C | 72.79 | 72.69 |
| H | 7.70 | 7.42 |
| N | 11.07 | 11.02 |

EXAMPLE 2

Preparation of (2S)-(−)-1-(4-indolyloxy)-3-(6-(12-azadispiro[4.1.4.2]tridecan-13-one)amino)-2-propanol ethanedioate The title compound was prepared in similar fashion from (S)-(+)-4-(oxiranylmethoxy)-1H-indole and 6-amino-12-azadispiro[4.1.4.2]tridecan-13-one. The resulting free base was dissolved in ethyl acetate, and precipitated with one equivalent of oxalic acid in ethyl acetate in 68% overall yield. mp 115°–117°. FDMS m/e=397 ($M^+$ of free base). $\alpha[D]_{589}$=−5.11 (c=1.02, methanol).

| analysis | calculated | found |
| --- | --- | --- |
| C | 61.59 | 61.44 |
| H | 6.82 | 7.04 |
| N | 8.62 | 8.45 |

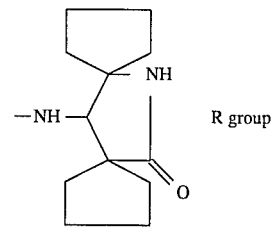

EXAMPLE 3

Preparation of (2S)-(−)-1-(4-indolyloxy)-3-(4-[2,2,6,6-tetramethyl]piperidinylamino)-2-propanol The title compound was prepared in similar fashion from (S)-(+)-4-(oxiranylmethoxy)-1H-indole and 4-amino-2,2,6,6-tetramethylpiperidine in 68% yield. FDMS m/e=345 ($M^+$ of free base). $\alpha[D]_{589}$=−2.54 (c=0.9, methanol).

| analysis | calculated | found |
| --- | --- | --- |
| C | 69.53 | 69.77 |
| H | 9.04 | 9.17 |
| N | 12.16 | 12.28 |

EXAMPLE 4

Preparation of (2S)-(−)-1-(4-indolyloxy)-3-(3-(10,11-dihydro-5H-dibenz[b,f]azepin-5-yl)propylamino)-2-propanol ethanedioate The title compound was prepared in similar fashion from (S)-(+)-4-(oxiranylmethoxy)-1H-indole and 3-(10,11-dihydro-5H)-dibenz[b,f]azepin-5-yl-propanamine in 53% overall yield. FDMS m/e=441 ($M^+$ of free base). $\alpha[D]_{589}$=−19.48 (c=0.62, methanol).

EXAMPLE 5

Preparation of (2S)-(−)-1-(4-indolyloxy)-3-(2-tetrahydrofurfurylamino)-2-propanol ethanedioate The title compound was prepared in similar fashion from (S)-(+)-4-(oxiranylmethoxy)-1H-indole and 2-tetrahydrofurfurylamine. The resulting free base was dissolved in ethyl acetate, and precipitated with one equivalent of oxalic acid in ethyl acetate in 49% overall yield. mp 112°–114°. FDMS m/e=290 ($M^+$ of free base). $\alpha[D]_{589}$=−12.79 (c=1.0, methanol).

| analysis | calculated | found |
|---|---|---|
| C | 56.84 | 56.59 |
| H | 6.36 | 6.39 |
| N | 7.36 | 7.66 |

EXAMPLE 6

Preparation of (2S)-(−)-1-(4-indolyloxy)-3-(3-[N-morpholino]propylamino)-2-propanol ethanedioate The title compound was prepared in similar fashion from (S)-(+)-4-(oxiranylmethoxy)-1H-indole and 3-(N-morpholino)propylamine. The resulting free base was dissolved in ethyl acetate, and precipitated with one equivalent of oxalic acid in ethyl acetate in 33% overall yield. mp 120°–121°. FDMS m/e=333 ($M^+$ of free base). $\alpha[D]_{589}$=−20.8 (c=0.6, methanol).

| analysis | calculated | found |
|---|---|---|
| C | 56.73 | 56.87 |
| H | 6.90 | 6.96 |
| N | 9.92 | 9.77 |

EXAMPLE 7

Preparation of (2S)-(−)-1-(4-indolyloxy)-3-(4-(formyl)piperazin-1-yl)-2-propanol The title compound was prepared in similar fashion from (S)-(+)-4-(oxiranylmethoxy)-1H-indole and 1-formylpiperazine in 86% yield. mp 106°–107°. FDMS m/e=303 ($M^+$ of free base). $\alpha[D]_{589}$=−1.98 (c=1.0, methanol).

| analysis | calculated | found |
|---|---|---|
| C | 63.35 | 62.13 |
| H | 6.98 | 7.11 |
| N | 13.85 | 13.75 |

EXAMPLE 8

Preparation of (2S)-(−)-1-(4-indolyloxy)-3-(4-(2-pyridyl)piperazin-1-yl)-2-propanol ethanedioate The title compound was prepared in similar fashion from (S)-(+)-4-(oxiranylmethoxy)-1H-indole and 1-(2-pyridyl)piperazine. The resulting free base was dissolved in ethyl acetate, and precipitated with one equivalent of oxalic acid in ethyl acetate in 90% overall yield. FDMS m/e=352 ($M^+$ of free base). $\alpha[D]_{589}$=−31.14 (c=0.86, methanol).

| analysis | calculated | found |
|---|---|---|
| C | 59.72 | 59.43 |
| H | 5.92 | 6.13 |
| N | 12.66 | 12.79 |

EXAMPLE 9

Preparation of (2S)-(−)-1-(4-indolyloxy)-3-(4-[(2,3-dihydro-1,4-benzodioxin-2-yl)methyl]piperazin-1-yl)-2-propanol ethanedioate The title compound was prepared in similar fashion from (S)-(+)-4-(oxiranylmethoxy)-1H-indole and 1-[(2,3-dihydro-1,4-benzodioxin-2-yl)methyl]piperazine. The resulting free base was dissolved in ethyl acetate, and precipitated with one equivalent of oxalic acid in ethyl acetate in 77% overall yield. FDMS m/e=423 ($M^+$ of free base). $\alpha[D]_{589}$=−10.21 (c=0.82, methanol).

| analysis | calculated | found |
|---|---|---|
| C | 60.81 | 60.59 |
| H | 6.08 | 6.19 |
| N | 8.18 | 7.79 |

EXAMPLE 10

Preparation of (2S)-(−)-1-(4-indolyloxy)-3-(4-(2,6-dimethylphenyl)piperazin-1-yl)-2-propanol ethanedioate The title compound was prepared in similar fashion from (S)-(+)-4-(oxiranylmethoxy)-1H-indole and 1-(2,6-dimethylphenyl)piperazine. The resulting free base was dissolved in ethyl acetate, and precipitated with one equivalent of oxalic acid in ethyl acetate in 50% overall yield. FDMS m/e=379 ($M^+$ of free base). $\alpha[D]_{589}$=−11.89 (c=0.47, methanol).

| analysis | calculated | found |
|---|---|---|
| C | 63.95 | 63.93 |
| H | 6.65 | 6.36 |
| N | 8.95 | 8.64 |

EXAMPLE 11

Preparation of (2S)-(−)-1-(4-indolyloxy)-3-(4-(2,3-dimethylphenyl)piperazin-1-yl)-2-propanol ethanedioate The title compound was prepared in similar fashion from (S)-(+)-4-(oxiranylmethoxy)-1H-indole and 1-(2,3-dimethylphenyl)piperazine. The resulting free base was dissolved in ethyl acetate, and precipitated with one equivalent of oxalic acid in ethyl acetate in 83% overall yield. FDMS m/e=379 ($M^+$ of free base). $\alpha[D]_{589}$=−9.84 (c=0.75, methanol).

| analysis | calculated | found |
|---|---|---|
| C | 63.95 | 63.60 |
| H | 6.65 | 6.72 |
| N | 8.95 | 8.91 |

EXAMPLE 12

Preparation of (2S)-(−)-1-(4-indolyloxy)-3-(4-bis(4-fluorophenyl)methylenepiperidin-1-yl)-2-propanol ethanedioate The title compound was prepared in similar fashion from (S)-(+)-4-(oxiranylmethoxy)-1H-indole and 4-(bis(4-fluorophenyl)methylenepiperidine. The resulting free base was dissolved in ethyl acetate, and precipitated with one equivalent of oxalic acid in ethyl acetate in 88% overall yield. FDMS m/e=474 ($M^+$ of free base). $\alpha[D]_{589}$=−8.49 (c=0.71, methanol).

| analysis | calculated | found |
|---|---|---|
| C | 65.95 | 65.75 |
| H | 5.36 | 5.55 |
| N | 4.96 | 4.61 |

EXAMPLE 13

Preparation of (2S)-(−)-1-(4-indolyloxy)-3-(4-(4-quinolinyl)piperazin-1-yl)-2-propanol ethanedioate The title compound was prepared in similar fashion from (S)-(+)-4-(oxiranylmethoxy)-1H-indole and 1-(4-quinolinyl)piperazine. The resulting free base was dissolved in ethyl acetate, and precipitated with one equivalent of oxalic acid in ethyl acetate in 64% overall yield. mp 150°–151°. FDMS m/e=402 ($M^+$ of free base). $\alpha[D]_{589}$=−12.41 (c=0.76, methanol).

| analysis | calculated | found |
|---|---|---|
| C | 63.40 | 63.10 |
| H | 5.73 | 5.50 |
| N | 11.37 | 11.25 |

EXAMPLE 14

Preparation of (2S)-(−)-1-(4-indolyloxy)-3-(4-bis(4-chlorophenyl)methylpiperazin-1-yl)-2-propanol ethanedioate The title compound was prepared in similar fashion from (S)-(+)-4-(oxiranylmethoxy)-1H-indole and 1-(bis(4-chlorophenyl)methylpiperazine. The resulting free base was dissolved in ethyl acetate, and precipitated with one equivalent of oxalic acid in ethyl acetate in 82% overall yield. mp 123°–124°. FDMS m/e=510 ($M^+$ of free base). $\alpha[D]_{589}$=−8.46 (c=0.89, methanol).

| analysis | calculated | found |
|---|---|---|
| C | 60.00 | 59.72 |
| H | 5.20 | 5.50 |
| N | 6.98 | 6.68 |

EXAMPLE 15

Preparation of (2S)-(−)-1-(4-indolyloxy)-3-(4-(4-trifluoromethylphenyl)piperazin-1-yl)-2-propanol ethanedioate The title compound was prepared in similar fashion from (S)-(+)-4-(oxiranylmethoxy)-1H-indole and 1-(4-trifluoromethylphenyl)piperazine. The resulting free base was dissolved in ethyl acetate, and precipitated with one equivalent of oxalic acid in ethyl acetate in 89% overall yield. FDMS m/e=419 ($M^+$ of free base). $\alpha[D]_{589}$=−7.78 (c=0.72, methanol).

| analysis | calculated | found |
|---|---|---|
| C | 56.58 | 56.51 |
| H | 5.14 | 5.44 |
| N | 8.25 | 7.96 |

EXAMPLE 16

Preparation of (2S)-(−)-1-(4-indolyloxy)-3-(4-(2-trifluoromethylphenyl)piperazin-1-yl)-2-propanol ethanedioate The title compound was prepared in similar fashion from (S)-(+)-4-(oxiranylmethoxy)-1H-indole and 1-(2-trifluoromethylphenyl)piperazine. The resulting free base was dissolved in ethyl acetate, and precipitated with one equivalent of oxalic acid in ethyl acetate in 70% overall yield. mp 123°–124°. FDMS m/e=419 ($M^+$ of free base). $\alpha[D]_{589}$=−7.01 (c=0.66, methanol).

| analysis | calculated | found |
|---|---|---|
| C | 56.58 | 56.82 |
| H | 5.14 | 5.32 |
| N | 8.25 | 8.05 |

EXAMPLE 17

Preparation of (2S)-(−)-1-(4-indolyloxy)-3-(4-(3-bromophenyl)piperazin-1-yl)-2-propanol ethanedioate The title compound was prepared in similar fashion from (S)-(+)-4-(oxiranylmethoxy)-1H-indole and 1-(3-bromophenyl)piperazine. The resulting free base was dissolved in ethyl acetate, and precipitated with one equivalent of oxalic acid in ethyl acetate in 84% overall yield. mp 144°–145°. FDMS m/e=429 ($M^+$ of free base). $\alpha[D]_{589}$=−8.12 (c=0.81, methanol).

| analysis | calculated | found |
|---|---|---|
| C | 53.09 | 53.07 |
| H | 5.04 | 5.29 |
| N | 8.07 | 7.99 |

EXAMPLE 18

Preparation of (2S)-(−)-1-(4-indolyloxy)-3-(4-(t-butyl)piperazin-1-yl)-2-propanol ethanedioate The title compound was prepared in similar fashion from (S)-(+)-4-(oxiranylmethoxy)-1H-indole and 1-(4-t-butyl)piperazine. The resulting free base was dissolved in ethyl acetate, and precipitated with one equivalent of oxalic acid in ethyl acetate in 75% overall yield. mp 179°–180°. FDMS m/e=331 ($M^+$ of free base). $\alpha[D]_{589}$=−4.73 (c=0.93, methanol).

| analysis | calculated | found |
|---|---|---|
| C | 59.84 | 59.70 |
| H | 7.41 | 7.17 |
| N | 9.97 | 9.74 |

EXAMPLE 19

Preparation of (2S)-(–)-1-(4-indolyloxy)-3-(4-(3,4-dichlorophenyl)piperazin-1-yl)-2-propanol ethanedioate The title compound was prepared in similar fashion from (S)-(+)-4-(oxiranylmethoxy)-1H-indole and 1-(3,4-dichlorophenyl)piperazine. The resulting free base was dissolved in ethyl acetate, and precipitated with one equivalent of oxalic acid in ethyl acetate in 87% overall yield. FDMS m/e=419 ($M^+$ of free base). $\alpha[D]_{589}$=–7.76 (c=0.82, methanol).

| analysis | calculated | found |
|---|---|---|
| C | 54.13 | 54.43 |
| H | 4.94 | 5.03 |
| N | 8.23 | 8.32 |

EXAMPLE 20

Preparation of (2S)-(–)-1-(4-indolyloxy)-3-(4-(isopropyl)piperazin-1-yl)-2-propanol ethanedioate The title compound was prepared in similar fashion from (S)-(+)-4-(oxiranylmethoxy)-1H-indole and 1-(4-isopropyl)piperazine. The resulting free base was dissolved in ethyl acetate, and precipitated with one equivalent of oxalic acid in ethyl acetate in 65% overall yield. mp 150°–152°. FDMS m/e=317 ($M^+$ of free base). $\alpha[D]_{589}$=–6.63 (c=0.99, methanol).

| analysis | calculated | found |
|---|---|---|
| C | 58.96 | 58.68 |
| H | 7.17 | 6.87 |
| N | 10.31 | 10.07 |

EXAMPLE 21

Preparation of (2S)-(–)-1-(4-indolyloxy)-3-(4-phenylpiperidin-1-yl)-2-propanol ethanedioate The title compound was prepared in similar fashion from (S)-(+)-4-(oxiranylmethoxy)-1H-indole and 4-phenylpiperidine. The resulting free base was dissolved in ethyl acetate, and precipitated with one equivalent of oxalic acid in ethyl acetate in 80% overall yield. FDMS m/e=351 ($M^+$ of free base). $\alpha[D]_{589}$=–15.49 (c=0.86, methanol).

| analysis | calculated | found |
|---|---|---|
| C | 65.44 | 65.48 |
| H | 6.41 | 6.44 |
| N | 6.36 | 6.06 |

EXAMPLE 22

Preparation of (2S)-(–)-1-(4-indolyloxy)-3-(4-(3-phenylpropyl)piperidin-1-yl)-2-propanol ethanedioate The title compound was prepared in similar fashion from (S)-(+)-4-(oxiranylmethoxy)-1H-indole and 4-(3-phenylpropyl)piperidine. The resulting free base was dissolved in ethyl acetate, and precipitated with one equivalent of oxalic acid in ethyl acetate in 73% overall yield. FDMS m/e=392 ($M^+$ of free base). $\alpha[D]_{589}$=–13.53 (c=0.58, methanol).

| analysis | calculated | found |
|---|---|---|
| C | 67.20 | 67.50 |
| H | 7.10 | 7.14 |
| N | 5.80 | 5.62 |

EXAMPLE 23

Preparation of (2S)-(–)-1-(4-indolyloxy)-3-([4-(pyridazin-3-one-6-yl)phenyl]piperidin-1-yl)-2-propanol The title compound was prepared in similar fashion from (S)-(+)-4-(oxiranylmethoxy)-1H-indole and 4-[4-(pyridazin-3-one-6-yl)phenyl]piperidine in 72% yield. mp 202°–203°. FDMS m/e=446 ($M^+$ of free base). $\alpha[D]_{589}$=–9.94 (c=0.84, methanol).

| analysis | calculated | found |
|---|---|---|
| C | 69.93 | 69.84 |
| H | 6.77 | 6.92 |
| N | 12.55 | 12.80 |

EXAMPLE 24

Preparation of (2S)-(–)-1-(4-indolyloxy)-3-(4-hydroxy-4-(3-trifluoromethylphenyl)piperidin-1-yl)-2-propanol ethanedioate The title compound was prepared in similar fashion from (S)-(+)-4-(oxiranylmethoxy)-1H-indole and 4-hydroxy-4-(3-trifluoromethylphenyl)piperidine. The resulting free base was dissolved in ethyl acetate, and precipitated with one equivalent of oxalic acid in ethyl acetate in 59% overall yield. FDMS m/e=426 ($M^+$ of free base). $\alpha[D]_{589}$=–11.39 (c=0.56, methanol).

| analysis | calculated | found |
|---|---|---|
| C | 57.25 | 57.11 |
| H | 5.19 | 4.98 |
| N | 5.34 | 5.14 |

EXAMPLE 25

Preparation of (2S)-(–)-1-(4-indolyloxy)-3-(4,4-diphenylpiperidin-1-yl)-2-propanol ethanedioate The title compound was prepared in similar fashion from (S)-(+)-4-(oxiranylmethoxy)-1H-indole and 4,4-diphenylpiperidine. The resulting free base was dissolved in ethyl acetate, and precipitated with one equivalent of oxalic acid in ethyl acetate in 60% overall yield. mp 198°–199°. FDMS m/e=426 (M⁺ of free base). α[D]$_{589}$=−17.80 (c=0.66, methanol).

| analysis | calculated | found |
|---|---|---|
| C | 69.75 | 69.83 |
| H | 6.24 | 6.29 |
| N | 5.42 | 5.08 |

EXAMPLE 26

Preparation of (2S)-(−)-1-(4-indolyloxy)-3-(4-(10,11-dihydro-5H-dibenzo[a,d]cyclohepten-5-yl)piperidin-1-yl)-2-propanol ethanedioate The title compound was prepared in similar fashion from (S)-(+)-4-(oxiranylmethoxy)-1H-indole and 4-(10,11-dihydro-5H-dibenzo[a,d]cyclohepten-5-yl)piperidine. The resulting free base was dissolved in ethyl acetate, and precipitated with one equivalent of oxalic acid in ethyl acetate in 89% overall yield. FDMS m/e=466 (M⁺ of free base). α[D]$_{589}$=−10.02 (c=0.72, methanol).

| analysis | calculated | found |
|---|---|---|
| C | 71.20 | 71.03 |
| H | 6.52 | 6.84 |
| N | 5.03 | 4.72 |

EXAMPLE 27

Preparation of (2S)-(−)-1-(4-indolyloxy)-3-(4-(3-(1,2,4-triazolo[3,4-b]benzothiazolyl))piperazin-1-yl)-2-propanol ethanedioate The title compound was prepared in similar fashion from (S)-(+)-4-(oxiranylmethoxy)-1H-indole and 1-(3-(1,2,4-triazolo[3,4-b]benzothiazolyl))piperazine. The resulting free base was dissolved in ethyl acetate, and precipitated with one equivalent of oxalic acid in ethyl acetate in 56% overall yield. FDMS m/e=448 (M⁺ of free base). α[D]$_{589}$=−10.42 (c=0.50, methanol).

| analysis | calculated | found |
|---|---|---|
| C | 55.75 | 55.72 |
| H | 4.87 | 4.98 |
| N | 15.60 | 15.43 |

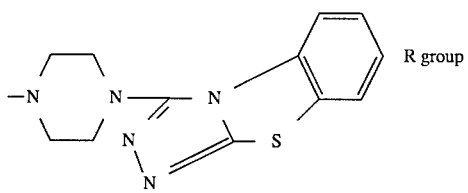

EXAMPLE 28

Preparation of (2S)-(−)-1-(4-indolyloxy)-3-(4-(diphenylmethyl)piperidin-1-yl)-2-propanol ethanedioate The title compound was prepared in similar fashion from (S)-(+)-4-(oxiranylmethoxy)-1H-indole and 4-(diphenylmethyl)piperidine. The resulting free base was dissolved in ethyl acetate, and precipitated with one equivalent of oxalic acid in ethyl acetate in 81% overall yield. mp 160°–161°. FDMS m/e=441 (M⁺ of free base). α[D]$_{589}$=−8.71 (c=0.89, methanol).

| analysis | calculated | found |
|---|---|---|
| C | 70.17 | 69.98 |
| H | 6.46 | 6.75 |
| N | 5.28 | 4.93 |

EXAMPLE 29

Preparation of (2S)-(−)-1-(4-indolyloxy)-3-(4-hydroxy-4-(4-fluorophenyl)piperidin-1-yl)-2-propanol ethanedioate The title compound was prepared in similar fashion from (S)-(+)-4-(oxiranylmethoxy)-1H-indole and 4-hydroxy-4-(4-fluorophenyl)piperidine. The resulting free base was dissolved in ethyl acetate, and precipitated with one equivalent of oxalic acid in ethyl acetate in 77% overall yield. FDMS m/e=384 (M⁺ of free base). α[D]$_{589}$=−11.40 (c=0.66, methanol).

| analysis | calculated | found |
|---|---|---|
| C | 60.75 | 60.46 |
| H | 5.74 | 5.79 |
| N | 5.90 | 5.64 |

EXAMPLE 30

Preparation of (2S)-(−)-1-(4-indolyloxy)-3-(4-(4-methoxyphenyl)piperidin-1-yl)-2-propanol ethanedioate The title compound was prepared in similar fashion from (S)-(+)-4-(oxiranylmethoxy)-1H-indole and 4-(4-methoxyphenyl)piperidine. The resulting free base was dissolved in ethyl acetate, and precipitated with one equivalent of oxalic acid in ethyl acetate in 66% overall yield. FDMS m/e=380 (M⁺ of free base). α[D]$_{589}$=−11.77 (c=0.61, methanol).

| analysis | calculated | found |
|---|---|---|
| C | 63.82 | 63.61 |
| H | 6.43 | 6.65 |
| N | 5.95 | 5.67 |

EXAMPLE 31

Preparation of (2S)-(−)-1-(4-indolyloxy)-3-(4-trifluoromethylphenyl)piperidin-1-yl)-2-propanol ethanedioate The title compound was prepared in similar fashion from (S)-(+)-4-(oxiranylmethoxy)-1H-indole and 4-(3-trifluoromethylphenyl)piperidine. The resulting free base was dissolved in ethyl acetate, and precipitated with one equivalent of oxalic acid in ethyl acetate in 50% overall yield. FDMS m/e=419 (M⁺ of free base). α[D]$_{589}$=−11.62 (c=0.45, methanol).

| analysis | calculated | found |
|---|---|---|
| C | 59.05 | 59.15 |
| H | 5.35 | 5.50 |
| N | 5.51 | 5.26 |

EXAMPLE 32

Preparation of (2S)-(–)-1-(4-indolyloxy)-3-(4-bis(4-fluorophenyl)methylpiperidin-1-yl)-2-propanol ethanedioate The title compound was prepared in similar fashion from (S)-(+)-4-(oxiranylmethoxy)-1H-indole and 4-(bis(4-fluorophenyl)methylpiperidine. The resulting free base was dissolved in ethyl acetate, and precipitated with one equivalent of oxalic acid in ethyl acetate in 64% overall yield. FDMS m/e=476 ($M^+$ of free base). $\alpha[D]_{589}$=–9.85 (c=0.89, methanol).

| analysis | calculated | found |
|---|---|---|
| C | 65.71 | 65.46 |
| H | 5.69 | 5.95 |
| N | 4.94 | 4.74 |

EXAMPLE 33

Preparation of (2S)-(–)-1-(4-indolyloxy)-3-(4-hydroxy-4-phenylpiperidin-1-yl)-2-propanol ethanedioate The title compound was prepared in similar fashion from S)-(+)-4-(oxiranylmethoxy)-1H-indole and 4-hydroxy-4-phenylpiperidine. The resulting free base was dissolved in ethyl acetate, and precipitated with one equivalent of oxalic acid in ethyl acetate in 69% overall yield. FDMS m/e=366 ($M^+$ of free base). $\alpha[D]_{589}$=–10.45 (c=0.61, methanol).

| analysis | calculated | found |
|---|---|---|
| C | 63.15 | 62.81 |
| H | 6.18 | 6.08 |
| N | 6.14 | 5.99 |

EXAMPLE 34

Preparation of (2S)-(–)-1-(4-indolyloxy)-3-(4-hydroxy-4-(3-methoxyphenyl)piperidin-1-yl)-2-propanol ethanedioate The title compound was prepared in similar fashion from (S)-(+)-4-(oxiranylmethoxy)-1H-indole and 4-hydroxy-4-(3-methoxyphenyl)piperidine. The resulting free base was dissolved in ethyl acetate, and precipitated with one equivalent of oxalic acid in ethyl acetate in 76% overall yield. FDMS m/e=396 ($M^+$ of free base). $\alpha[D]_{589}$=–8.13 (c=0.69, methanol).

| analysis | calculated | found |
|---|---|---|
| C | 61.73 | 61.51 |
| H | 6.21 | 6.18 |
| N | 5.76 | 5.59 |

EXAMPLE 35

Preparation of (2S)-(–)-1-(4-indolyloxy)-3-(4-piperidin-1-yl)piperidin-1-yl)-2-propanol ethanedioate The title compound was prepared in similar fashion from (S)-(+)-4-(oxiranylmethoxy)-1H-indole and 4-(piperidin-1-yl)piperidine. The resulting free base was dissolved in ethyl acetate, and precipitated with one equivalent of oxalic acid in ethyl acetate in 60% overall yield. mp 220°–221°. FDMS m/e=358 ($M^+$ of free base).

| analysis | calculated | found |
|---|---|---|
| C | 61.73 | 61.33 |
| H | 7.43 | 7.06 |
| N | 9.39 | 8.96 |

EXAMPLE 36

Preparation of (2S)-(–)-1-(4-indolyloxy)-3-(spiro[benzodihydrofuran-3-one-1(3H),4'-piperidin]-1'-yl)-2-propanol ethanedioate The title compound was prepared in similar fashion from (S)-(+)-4-(oxiranylmethoxy)-1H-indole and spiro[benzodihydrofuran-3-one-1(3H),4'-piperidine]. The resulting free base was dissolved in ethyl acetate, and precipitated with one equivalent of oxalic acid in ethyl acetate in 73% overall yield. mp 198°–199°. FDMS m/e=392 ($M^+$ of free base). $\alpha[D]_{589}$=–12.04 (c=0.85, methanol).

| analysis | calculated | found |
|---|---|---|
| C | 62.23 | 62.10 |
| H | 5.43 | 5.39 |
| N | 5.81 | 5.93 |

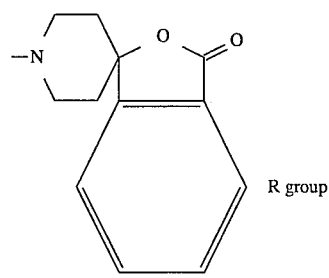

R group

EXAMPLE 37

Preparation of (2S)-(–)-1-(4-indolyloxy)-3-(spiro[benzodihydrofuran-1(3H),4'-piperidin]-1'-yl)-2-propanol ethanedioate The title compound was prepared in similar fashion from (S)-(+)-4-(oxiranylmethoxy)-1H-indole and spiro[benzodihydrofuran-1(3H),4'-piperidine]. The resulting free base was dissolved in ethyl acetate, and precipitated with one equivalent of oxalic acid in ethyl acetate in 85% overall yield. FDMS m/e=378 ($M^+$ of free base). $\alpha[D]_{589}$=–10.28 (c=0.45, methanol).

| analysis | calculated | found |
|---|---|---|
| C | 64.09 | 63.92 |
| H | 6.02 | 6.26 |
| N | 5.98 | 5.93 |

EXAMPLE 38

Preparation of (2S)-(−)-1-(4-indolyloxy)-3-(4-phenoxypiperidin-1-yl)-2-propanol ethanedioate The title compound was prepared in similar fashion from (S)-(+)-4-(oxiranylmethoxy)-1H-indole and 4-(phenoxy)piperidine. The resulting free base was dissolved in ethyl acetate, and precipitated with one equivalent of oxalic acid in ethyl acetate in 69% overall yield. FDMS m/e=366 ($M^+$ of free base). $\alpha[D]_{589}$=−14.29 (c=0.5, methanol).

| analysis | calculated | found |
|---|---|---|
| C | 63.15 | 63.89 |
| H | 6.18 | 6.08 |
| N | 6.14 | 5.94 |

EXAMPLE 39

Preparation of (2S)-(−)-1-(4-indolyloxy)-3-(4-[1-(2-phenyl)benzimidazolyl]piperidinyl-1)-2-propanol ethanedioate The title compound was prepared in similar fashion from (S)-(+)-4-(oxiranylmethoxy)-1H-indole and 4-(1-(2-phenyl)benzimidazolyl)piperidine. The resulting free base was dissolved in ethyl acetate, and precipitated with one equivalent of oxalic acid in ethyl acetate in 71% overall yield. mp 168°–170°. FDMS m/e=466 ($M^+$ of free base). $\alpha[D]_{589}$=−8.44 (c=0.59, methanol).

| analysis | calculated | found |
|---|---|---|
| C | 66.89 | 66.51 |
| H | 5.80 | 5.87 |
| N | 10.07 | 9.77 |

EXAMPLE 40

Preparation of (2S)-(−)-1-(4-indolyloxy)-3-(4-[5-chloro-1-indol-2-one]piperidin-1-yl)-2-propanol ethanedioate The title compound was prepared in similar fashion from (S)-(+)-4-(oxiranylmethoxy)-1H-indole and 4-(5-chloro-1-indol-2-one)piperidine. The resulting free base was dissolved in ethyl acetate, and precipitated with one equivalent of oxalic acid in ethyl acetate in 59% overall yield. mp 230°–231°. FDMS m/e=439 ($M^+$ of free base).

| analysis | calculated | found |
|---|---|---|
| C | 58.93 | 59.13 |
| H | 5.33 | 5.41 |
| N | 7.93 | 8.10 |

EXAMPLE 41

Preparation of (2S)-(−)-1-(4-indolyloxy)-3-(4-[2-(1-methyl)benzimidazolyl]piperidin-1-yl)-2-propanol ethanedioate The title compound was prepared in similar fashion from (S)-(+)-4-(oxiranylmethoxy)-1H-indole and 4-(2-(1-methyl)benzimidazolyl)piperidine. The resulting free base was dissolved in ethyl acetate, and precipitated with one equivalent of oxalic acid in ethyl acetate in 70% overall yield. FDMS m/e=404 ($M^+$ of free base). $\alpha[D]_{589}$=−6.04 (c=0.53, methanol).

| analysis | calculated | found |
|---|---|---|
| C | 63.15 | 63.09 |
| H | 6.11 | 6.47 |
| N | 11.33 | 11.43 |

EXAMPLE 42

Preparation of (2S)-(−)-1-(4-indolyloxy)-3-(4-phenyl-4-(4-trifluoromethylphenoxy)piperidin-1-yl)-2-propanol ethanedioate The title compound was prepared in similar fashion from (S)-(+)-4-(oxiranylmethoxy)-1H-indole and 4-phenyl-4-(4-trifluoromethylphenoxy)piperidine. The resulting free base was dissolved in ethyl acetate, and precipitated with one equivalent of oxalic acid in ethyl acetate in 49% overall yield. FDMS m/e=510 ($M^+$ of free base). $\alpha[D]_{589}$=−11.99 (c=0.42, methanol).

| analysis | calculated | found |
|---|---|---|
| C | 62.00 | 61.82 |
| H | 5.20 | 5.43 |
| N | 4.66 | 4.58 |

EXAMPLE 43

Preparation of (2S)-(−)-1-(4-indolyloxy)-3-(1-heptamethyleneimino)-2-propanol ethanedioate The title compound was prepared in similar fashion from (S)-(+)-4-(oxiranylmethoxy)-1H-indole and heptamethyleneimine. The resulting free base was dissolved in ethyl acetate, and precipitated with one equivalent of oxalic acid in ethyl acetate in 62% overall yield. FDMS m/e=302 ($M^+$ of free base). $\alpha[D]_{589}$=−13.48 (c=0.61, methanol).

| analysis | calculated | found |
|---|---|---|
| C | 61.21 | 60.98 |
| H | 7.19 | 7.35 |
| N | 7.14 | 6.89 |

EXAMPLE 44

Preparation of (2S)-(−)-1-(4-indolyloxy)-3-(1-azabicyclo[3.2.2]nonanyl)-2-propanol ethanedioate The title compound was prepared in similar fashion from (S)-(+)-4-(oxiranylmethoxy)-1H-indole and 1-azabicyclo[3.2.2]nonane. The resulting free base was dissolved in ethyl acetate, and precipitated with one equivalent of oxalic acid in ethyl acetate in 85% overall yield. FDMS m/e=314 (M⁺ of free base). $\alpha[D]_{589}$=−20.39 (c=0.48, methanol).

| analysis | calculated | found |
|---|---|---|
| C | 62.36 | 62.09 |
| H | 6.98 | 6.94 |
| N | 6.93 | 6.59 |

EXAMPLE 45

Preparation of (2S)-(−)-1-(4-indolyloxy)-3-(4-hydroxy-4-(4-chlorophenyl)piperidin-1-yl)-2-propanol ethanedioate The title compound was prepared in similar fashion from (S)-(+)-4-(oxiranylmethoxy)-1H-indole and 4-hydroxy-4-(4-chlorophenyl)piperidine. The resulting free base was dissolved in ethyl acetate, and precipitated with one equivalent of oxalic acid in ethyl acetate in 83% overall yield. FDMS m/e=401 (M⁺ of free base). $\alpha[D]_{589}$=−14.17 (c=0.45, methanol).

| analysis | calculated | found |
|---|---|---|
| C | 58.72 | 59.06 |
| H | 5.54 | 5.66 |
| N | 5.71 | 5.54 |

EXAMPLE 46

Preparation of (2S)-(−)-1-(4-indolyloxy)-3-(4-[1-benzimidazol-2-one]piperidin-1-yl)-2-propanol ethanedioate The title compound was prepared in similar fashion from (S)-(+)-4-(oxiranylmethoxy)-1H-indole and 4-(1-benzimidazol-2-one)piperidine. The resulting free base was dissolved in ethyl acetate, and precipitated with one equivalent of oxalic acid in ethyl acetate in 88% overall yield. mp 123°–125°. FDMS m/e=406 (M⁺ of free base). $\alpha[D]_{589}$=−17.22 (c=0.48, methanol).

| analysis | calculated | found |
|---|---|---|
| C | 60.48 | 60.38 |
| H | 5.68 | 5.86 |
| N | 11.28 | 11.32 |

EXAMPLE 47

Preparation of (2S)-(−)-1-(4-indolyloxy)-3-(4-cyano-4-phenylpiperidin-1-yl)-2-propanol ethanedioate The title compound was prepared in similar fashion from (S)-(+)-4-(oxiranylmethoxy)-1H-indole and 4-cyano-4-phenylpiperidine. The resulting free base was dissolved in ethyl acetate, and precipitated with one equivalent of oxalic acid in ethyl acetate in 57% overall yield. FDMS m/e=(M⁺ of free base). $\alpha[D]_{589}$=−12.76 (c=0.48, methanol).

| analysis | calculated | found |
|---|---|---|
| C | 64.51 | 64.37 |
| H | 5.85 | 6.00 |
| N | 9.03 | 8.71 |

EXAMPLE 48

Preparation of (2S)-(−)-1-(4-indolyloxy)-3-(4-hydroxy-4-(4-bromophenyl)piperidin-1-yl)-2-propanol ethanedioate The title compound was prepared in similar fashion from (S)-(+)-4-(oxiranylmethoxy)-1H-indole and 4-hydroxy-4-(4-bromophenyl)piperidine. The resulting free base was dissolved in ethyl acetate, and precipitated with one equivalent of oxalic acid in ethyl acetate in 80% overall yield. FDMS m/e=444, 446 (M⁺ of free base). $\alpha[D]_{589}$=−7.52 (c=0.45, methanol).

| analysis | calculated | found |
|---|---|---|
| C | 59.33 | 59.54 |
| H | 5.66 | 5.56 |
| N | 6.29 | 5.98 |

EXAMPLE 49

Preparation of (2S)-(−)-1-(4-indolyloxy)-3-(4-hydroxy-4-(3-trifluoromethyl-4-chlorophenyl)piperidin-1-yl)-2-propanol ethanedioate The title compound was prepared in similar fashion from (S)-(+)-4-(oxiranylmethoxy)-1H-indole and 4-hydroxy-4-(3-trifluoromethyl-4-chlorophenyl)piperidine. The resulting free base was dissolved in ethyl acetate, and precipitated with one equivalent of oxalic acid in ethyl acetate in 85% overall yield. FDMS m/e=469 (M⁺ of free base). $\alpha[D]_{589}$=−11.53 (c=0.54, methanol).

| analysis | calculated | found |
|---|---|---|
| C | 53.72 | 53.53 |
| H | 4.69 | 5.01 |
| N | 5.01 | 4.83 |

EXAMPLE 50

Preparation of (2S)-(−)-1-(4-indolyloxy)-3-(4-spiro[9H-fluorene-9,4']hexamethyleneimino-1-yl)-2-propanol ethanedioate The title compound was prepared in similar fashion from (S)-(+)-4-(oxiranylmethoxy)-1H-indole and 4-spiro[9H-fluorene-9,4']hexamethyleneimine. The resulting free base was dissolved in ethyl acetate, and precipitated with one equivalent of oxalic acid in ethyl acetate in 64% overall yield. FDMS m/e=438 (M⁺ of free base). mp 131°–133°. $\alpha[D]_{589}$=−10.78 (c=0.43, methanol).

| analysis | calculated | found |
|---|---|---|
| C | 70.44 | 70.38 |
| H | 6.10 | 6.34 |
| N | 5.30 | 4.91 |

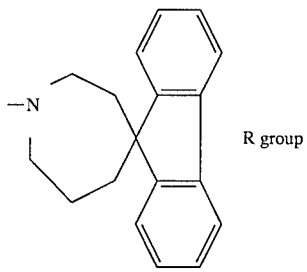

R group

EXAMPLE 51

Preparation of (2S)-(−)-1-(4-indolyloxy)-3-(trans-4-(3-hydroxyphenyl)-3-methyl-4-propylpiperidin-1-yl)-2-propanol ethanedioate The title compound was prepared in similar fashion from (S)-(+)-4-(oxiranylmethoxy)-1H-indole and trans-4-(3-hydroxyphenyl)-3-methyl-4-propylpiperidine. The resulting free base was dissolved in ethyl acetate, and precipitated with one equivalent of oxalic acid in ethyl acetate in 79% overall yield. mp 116°–118°. FDMS m/e=422 (M$^+$ of free base). α[D]$_{589}$=−9.85 (c=1.02, methanol).

| analysis | calculated | found |
|---|---|---|
| C | 65.61 | 65.77 |
| H | 7.08 | 7.09 |
| N | 5.46 | 5.17 |

EXAMPLE 52

Preparation of (2S)-(−)-1-(4-indolyloxy)-3-(3,3-diphenylpyrrolidin-1-yl)-2-propanol ethanedioate The title compound was prepared in similar fashion from (S)-(+)-4-(oxiranylmethoxy)-1H-indole and 3,3-diphenylpyrrolidine. The resulting free base was dissolved in ethyl acetate, and precipitated with one equivalent of oxalic acid in ethyl acetate in 68% overall yield. FDMS m/e=412 (M$^+$ of free base). mp 193°–194°. α[D]$_{589}$=−9.11 (c=0.33, methanol).

| analysis | calculated | found |
|---|---|---|
| C | 69.31 | 69.06 |
| H | 6.02 | 5.94 |
| N | 5.57 | 5.43 |

EXAMPLE 53

Preparation of (2S)-(−)-1-(4-indolyloxy)-3-(4,4-diphenylhexamethyleneimino-1-yl)-2-propanol ethanedioate The title compound was prepared in similar fashion from (S)-(+)-4-(oxiranylmethoxy)-1H-indole and 4,4-diphenylhexamethyleneimine. The resulting free base was dissolved in ethyl acetate, and precipitated with one equivalent of oxalic acid in ethyl acetate in 60% overall yield. FDMS m/e=440 (M$^+$ of free base). mp 103°–104°. α[D]$_{589}$=−9.11 (c=0.39, methanol).

| analysis | calculated | found |
|---|---|---|
| C | 70.17 | 70.04 |
| H | 6.46 | 6.71 |
| N | 5.28 | 4.93 |

EXAMPLE 54

Preparation of (2S)-(−)-1-(4-indolyloxy)-3-(4-(4-methylphenyl)piperidin-1-yl)-2-propanol ethanedioate The title compound was prepared in similar fashion from S)-(+)-4-(oxiranylmethoxy)-1H-indole and 4-(4-methylphenyl)piperidine. The resulting free base was dissolved in ethyl acetate, and precipitated with one equivalent of oxalic acid in ethyl acetate in 78% overall yield. FDMS m/e=364 (M$^+$ of free base). α[D]$_{589}$=−11.77 (c=0.34, methanol).

| analysis | calculated | found |
|---|---|---|
| C | 66.06 | 66.19 |
| H | 6.65 | 6.81 |
| N | 6.16 | 5.90 |

EXAMPLE 55

Preparation of (2S)-(−)-1-(4-indolyloxy)-3-(2,3,4,5-tetrahydro-1H-3-benzazepin-3-yl)-2-propanol ethanedioate The title compound was prepared in similar fashion from (S)-(+)-4-(oxiranylmethoxy)-1H-indole and 2,3,4,5-tetrahydro-1H-3-benzazepine. The resulting free base was dissolved in ethyl acetate, and precipitated with one equivalent of oxalic acid in ethyl acetate in 73% overall yield. FDMS m/e=336 (M$^+$ of free base). α[D]$_{589}$=−14.17 (c=0.61, methanol).

| analysis | calculated | found |
|---|---|---|
| C | 64.78 | 64.48 |
| H | 6.14 | 5.84 |
| N | 6.57 | 6.64 |

EXAMPLE 56

Preparation of (2S)-(−)-1-(4-indolyloxy)-3-(7,8-dimethoxy-2,3,4,5-tetrahydro-1H-3-benzazepin-3-yl)-2-propanol ethanedioate The title compound was prepared in similar fashion from (S)-(+)-4-(oxiranylmethoxy)-1H-indole and 7,8-dimethoxy-2,3,4,5-tetrahydro-1H-3-benzazepine. The resulting free base was dissolved in ethyl acetate, and precipitated with one equivalent of oxalic acid in ethyl acetate in 48% overall yield. FDMS m/e=396 (M$^+$ of free base). α[D]$_{589}$=−9.34 (c=0.47, methanol).

EXAMPLE 57

Preparation of (2S)-(−)-1-(4-indolyloxy -3-(6,7-dichloro-2,3,4,5-tetrahydro-1H-3-benzazepin-3-yl)-2-propanol ethanedioate The title compound was prepared in similar fashion from (S)-(+)-4-(oxiranylmethoxy)-1H-indole and 6,7-dichloro-2,3,4,5-tetrahydro-1H-3-benzazepine. The resulting free base was dissolved in ethyl acetate, and precipitated with one equivalent of oxalic acid in ethyl acetate in 77% overall yield. FDMS m/e=405 (M$^+$ of free base). $\alpha[D]_{589}$=−6.87 (c=0.44, methanol).

| analysis | calculated | found |
|---|---|---|
| C | 61.72 | 61.76 |
| H | 6.21 | 6.60 |
| N | 5.76 | 5.91 |

| analysis | calculated | found |
|---|---|---|
| C | 55.77 | 55.70 |
| H | 4.88 | 5.14 |
| N | 5.65 | 5.69 |

EXAMPLE 58

Preparation of (2S)-(−)-1-(4-indolyloxy)-3-(4-(2-fluorophenyl)piperidin-1-yl)-2-propanol ethanedioate The title compound was prepared in similar fashion from (S)-(+)-4-(oxiranylmethoxy)-1H-indole and 4-(2-fluorophenyl)piperidine. The resulting free base was dissolved in ethyl acetate, and precipitated with one equivalent of oxalic acid in ethyl acetate in 40% overall yield. FDMS m/e=368 (M$^+$ of free base). $\alpha[D]_{589}$=−12.31 (c=0.61, methanol).

| analysis | calculated | found |
|---|---|---|
| C | 62.87 | 62.93 |
| H | 5.94 | 6.13 |
| N | 6.11 | 5.96 |

EXAMPLE 59

Preparation of (2S)-(−)-1-(4-indolyloxy)-3-(4-(2-methoxyphenyl)piperidin-1-yl)-2-propanol ethanedioate The title compound was prepared in similar fashion from (S)-(+)-4-(oxiranylmethoxy)-1H-indole and 4-(2-methoxyphenyl)piperidine. The resulting free base was dissolved in ethyl acetate, and precipitated with one equivalent of oxalic acid in ethyl acetate in 37% overall yield. FDMS m/e=380 (M$^+$ of free base). $\alpha[D]_{589}$=−14.83 (c=0.81, methanol).

| analysis | calculated | found |
|---|---|---|
| C | 63.82 | 63.87 |
| H | 6.43 | 6.58 |
| N | 5.95 | 5.53 |

EXAMPLE 60

Preparation of (2S)-(−)-1-(4-indolyloxy)-3-(benzo[c]spiro[benzodihydrofuran-1(3H),4'-piperidin]-3-one-1'-yl)-2-propanol ethanedioate The title compound was prepared in similar fashion from (S)-(+)-4-(oxiranylmethoxy)-1H-indole and benzo[c]spiro[benzodihydrofuran-1(3H),4'-piperidin]-3-one. The resulting free base was dissolved in ethyl acetate, and precipitated with one equivalent of oxalic acid in ethyl acetate in 87% overall yield. FDMS m/e=442 (M$^+$ of free base). $\alpha[D]_{589}$=−2.92 (c=1.02, methanol).

| analysis | calculated | found |
|---|---|---|
| C | 65.41 | 65.31 |
| H | 5.30 | 5.40 |
| N | 5.26 | 5.03 |

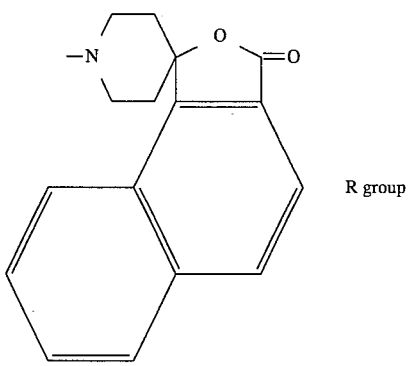

R group

EXAMPLE 61

Preparation of (2S)-(−)-1-(4-indolyloxy)-3-(5-methoxyspiro[benzodihydrofuran-1(3H),4'-piperidin]-3-one-1'-yl)-2-propanol ethanedioate The title compound was prepared in similar fashion from (S)-(+)-4-(oxiranylmethoxy)-1H-indole and 5-methoxyspiro[benzodihydrofuran-1(3H),4'-piperidin]-3-one. The resulting free base was dissolved in ethyl acetate, and precipitated with one equivalent of oxalic acid in ethyl acetate in 40% overall yield. mp 195°–197°. FDMS m/e=422 (M$^+$ of free base).

| analysis | calculated | found |
|---|---|---|
| C | 60.93 | 60.61 |
| H | 5.51 | 5.89 |
| N | 5.47 | 5.71 |

EXAMPLE 62

Preparation of (2S)-(−)-1-(4-indolyloxy)-3-(4-(4-trifluoromethoxyphenyl)piperidin-1-yl -2-propanol ethanedioate The title compound was prepared in similar fashion from (S)-(+)-4-(oxiranylmethoxy)-1H-indole and 4-(4-trifluoromethoxyphenyl)piperidine. The resulting free base was dissolved in ethyl acetate, and precipitated with one equivalent of oxalic acid in ethyl acetate in 76% overall yield.

FDMS m/e=434 (M⁺ of free base). α[D]₅₈₉=−13.45 (c=1.04, methanol).

| analysis | calculated | found |
|---|---|---|
| C | 57.25 | 56.99 |
| H | 5.19 | 5.43 |
| N | 5.34 | 5.04 |

EXAMPLE 63

Preparation of (2S)-(−)-1-(4-indolyloxy)-3-(4-(3,4-methylenedioxy)phenyl)piperidin-1-yl)-2-propanol ethanedioate The title compound was prepared in similar fashion from (S)-(+)-4-(oxiranylmethoxy)-1H-indole and 4-(3,4-methylenedioxyphenyl)piperidine. The resulting free base was dissolved in ethyl acetate, and precipitated with one equivalent of oxalic acid in ethyl acetate in 71% overall yield FDMS m/e=394 (M⁺ of free base). α[D]₅₈₉=−15.73 (c=1.02, methanol).

| analysis | calculated | found |
|---|---|---|
| C | 61.98 | 61.65 |
| H | 5.82 | 5.89 |
| N | 5.78 | 5.44 |

EXAMPLE 64

Preparation of (2s)-(−)-1-(4-indolyloxy)-3-(4-(2-naphthyl)piperidin-1-yl)-2-propanol ethanedioate The title compound was prepared in similar fashion from (S)-(+)-4-(oxiranylmethoxy)-1H-indole and 4-(2-naphthyl)piperidine. The resulting free base was dissolved in ethyl acetate, and precipitated with one equivalent of oxalic acid in ethyl acetate in 74% overall yield. mp. 171°–172°. FDMS m/e=400 (M⁺ of free base). α[D]₅₈₉=−13.51 (c=1.04, methanol).

| analysis | calculated | found |
|---|---|---|
| C | 68.56 | 68.28 |
| H | 6.16 | 6.45 |
| N | 5.71 | 5.51 |

EXAMPLE 65

Preparation of (2S)-(−)-1-(4-indolyloxy)-3-(4-(4-trifluoromethylphenyl)piperidin-1-yl)-2-propanol ethanedioate The title compound was prepared in similar fashion from (S)-(+)-4-(oxiranylmethoxy)-1H-indole and 4-(4-trifluoromethylphenyl)piperidine. The resulting free base was dissolved in ethyl acetate, and precipitated with one equivalent of oxalic acid in ethyl acetate in 34% overall yield. FDMS m/e=419 (M⁺ of free base). α[D]₅₈₉=−10.15 (c=0.47, methanol).

| analysis | calculated | found |
|---|---|---|
| C | 59.05 | 59.04 |
| H | 5.35 | 5.32 |
| N | 5.51 | 5.03 |

EXAMPLE 66

Preparation of (2S)-(−)-1-(4-indolyloxy)-3-(3,3-dimethylspiro[benzodihydrofuran-1(3H),4'-piperidin]-1'-yl)-2-propanol ethanedioate The title compound was prepared in similar fashion from (S)-(+)-4-(oxiranylmethoxy)-1H-indole and 3,3-dimethylspiro[benzodihydrofuran-1(3H),4'-piperidine]. The resulting free base was dissolved in ethyl acetate, and precipitated with one equivalent of oxalic acid in ethyl acetate in 52% overall yield. FDMS m/e=406 (M⁺ of free base). α[D]₅₈₉=−11.87 (c=0.72, methanol).

| analysis | calculated | found |
|---|---|---|
| C | 65.31 | 65.28 |
| H | 6.50 | 6.58 |
| N | 5.64 | 5.43 |

EXAMPLE 67

Preparation of (2S)-(−)-1-(4-indolyloxy)-3-(spiro[benzodihydrothiophene-1(3H),4'-piperidin]-1'-yl)-2-propanol ethanedioate The title compound was prepared in similar fashion from (S)-(+)-4-(oxiranylmethoxy)-1H-indole and spiro[benzodihydrothiophene-1(3H),4'-piperidine]. The resulting free base was dissolved in ethyl acetate, and precipitated with one equivalent of oxalic acid in ethyl acetate in 70% overall yield. FDMS m/e=394 (M⁺ of free base). α[D]₅₈₉=−10.86 (c=0.40, methanol).

| analysis | calculated | found |
|---|---|---|
| C | 61.97 | 61.73 |
| H | 5.82 | 5.89 |
| N | 5.78 | 5.51 |

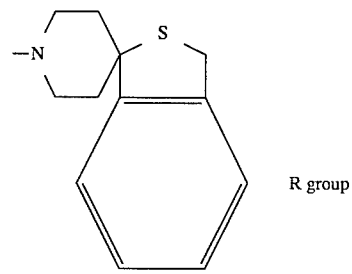

EXAMPLE 68

Preparation of (2S)-(−)-1-(4-indolyloxy)-3-(4-(4-fluorophenyl)piperidin-1-yl)-2-propanol ethanedioate The title compound was prepared in similar fashion from (S)-(+)-4-(oxiranylmethoxy)-1H-indole and 4-(4-fluorophenyl)piperidine. The resulting free base was dissolved in ethyl acetate, and precipitated with one equivalent of oxalic acid in ethyl acetate in 30% overall yield. FDMS m/e=369 (M⁺ of free base). α[D]₅₈₉=−2.49 (c=0.24, methanol).

| analysis | calculated | found |
|---|---|---|
| C | 62.87 | 62.61 |
| H | 5.94 | 5.73 |
| N | 6.11 | 5.82 |

EXAMPLE 69

Preparation of (2S)-(−)-1-(4-indolyloxy)-3-(4-(3-methoxyphenyl)piperidin-1-yl)-2-propanol ethanedioate The title compound was prepared in similar fashion from (S)-(+)-4-(oxiranylmethoxy)-1H-indole and 4-(3-methoxyphenyl)piperidine. The resulting free base was dissolved in ethyl acetate, and precipitated with one equivalent of oxalic acid in ethyl acetate in 30% overall yield. mp 121°–123°. FDMS m/e=381 (M⁺ of free base). α[D]₅₈₉=−12.69 (c=0.53, methanol).

| analysis | calculated | found |
|---|---|---|
| C | 63.82 | 63.59 |
| H | 6.43 | 6.51 |
| N | 5.95 | 5.90 |

EXAMPLE 70

Preparation of (2S)-(−)-1-(4-indolyloxy)-3-(spiro[indane-1,4'-piperidin]-1'-yl)-2-propanol ethanedioate The title compound was prepared in similar fashion from (S)-(+)-4-(oxiranylmethoxy)-1H-indole and spiro[indane-1,4'-piperidine]. The resulting free base was dissolved in ethyl acetate, and precipitated with one equivalent of oxalic acid in ethyl acetate in 76% overall yield. mp 110°–112°. FDMS m/e=376 (M⁺ of free base). α[D]₅₈₉=−11.60 (c=0.46, methanol).

| analysis | calculated | found |
|---|---|---|
| C | 66.94 | 66.64 |
| H | 6.48 | 6.52 |
| N | 6.00 | 6.05 |

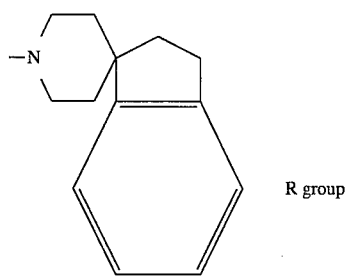
R group

EXAMPLE 71

Preparation of (2S)-(−)-1-(4-indolyloxy)-3-(spiro[1H-indene-1,4'-piperidin]-1'-yl)-2-propanol ethanedioate The title compound was prepared in similar fashion from (S)-(+)-4-(oxiranylmethoxy)-1H-indole and spiro[1H-indene-1,4'-piperidine]. The resulting free base was dissolved in ethyl acetate, and precipitated with one equivalent of oxalic acid in ethyl acetate in 80% overall yield. mp 119°–120°. FDMS m/e=374 (M⁺ of free base). α[D]₅₈₉=−5.51 (c=0.47, methanol).

| analysis | calculated | found |
|---|---|---|
| C | 67.23 | 66.91 |
| H | 6.08 | 6.11 |
| N | 6.03 | 5.88 |

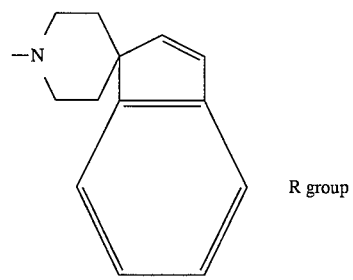
R group

EXAMPLE 72

Preparation of (2S)-(−)-1-(4-indolyloxy)-3-(4-spiro[9H-fluorene-9,4']-piperidin-1-yl)-2-propanol ethanedioate The title compound was prepared in similar fashion from (S)-(+)-4-(oxiranylmethoxy)-1H-indole and spiro[9H-fluorene-9,4'-piperidine]. The resulting free base was dissolved in ethyl acetate, and precipitated with one equivalent of oxalic acid in ethyl acetate in 57% overall yield. mp 133°–134°. FDMS m/e=424 (M⁺ of free base) α[D]₅₈₉=−9.15 (c=0.50, methanol).

| analysis | calculated | found |
|---|---|---|
| C | 70.02 | 69.85 |
| H | 5.88 | 6.08 |
| N | 5.44 | 5.29 |

EXAMPLE 73

Preparation of (2S)-(−)-1-(4-indolyloxy)-3-(4-(3,4-dimethoxyphenyl)piperidin-1-yl)-2-propanol ethanedioate The title compound was prepared in similar fashion from (S)-(+)-4-(oxiranylmethoxy)-1H-indole and 4-(3,4-dimethoxyphenyl)piperidine. The resulting free base was dissolved in ethyl acetate, and precipitated with one equivalent of oxalic acid in ethyl acetate in 82% overall yield. FDMS m/e=410 (M⁺ of free base). α[D]₅₈₉=−11.84 (c=0.46, methanol).

| analysis | calculated | found |
|---|---|---|
| C | 62.39 | 62.12 |
| H | 6.44 | 6.48 |
| N | 5.60 | 5.37 |

EXAMPLE 74

Preparation of (2S)-(−)-1-(4-indolyloxy)-3-(6-chlorospiro[benzodihydrofuran-1(3H),4'-piperidin]-1'-yl)-2-propanol ethanedioate The title compound was prepared in similar fashion from (S)-(+)-4-(oxiranylmethoxy)-1H-indole and 6-chlorospiro[benzodihydrofuran-1(3H),4'-piperidine]. The resulting free base was dissolved in ethyl acetate, and precipitated with one equivalent of oxalic acid in ethyl acetate in 68% overall yield. FDMS m/e=412 ($M^+$ of free base). $\alpha[D]_{589}$=−5.60 (c=0.36, methanol).

| analysis | calculated | found |
|---|---|---|
| C | 59.70 | 59.62 |
| H | 5.41 | 5.19 |
| N | 5.57 | 5.59 |

EXAMPLE 75

Preparation of 1-(4-indolyloxy)-3-(8-[1-phenyl-1,3,8-triazaspiro[4.5]decan-4-one])-2-propanol The title compound was prepared in similar fashion from 4-(oxiranylmethoxy)-1H-indole and 1-phenyl-1,3,8-triazaspiro[4.5]decan-4-one in 47% yield. FDMS m/e=420. mp 213°–214°.

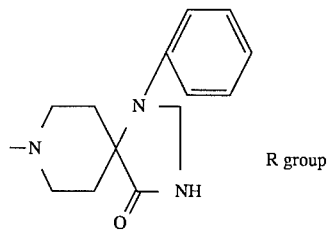

R group

EXAMPLE 76

Preparation of 1-(4-indolyloxy)-3-([2-(1-methyl-1H-pyrrol-2-yl)ethyl]amino)-2-propanol The title compound was prepared in similar fashion from 4-(oxiranylmethoxy)-1H-indole and 2-(1-methyl-1H-pyrrol-2-yl)ethylamine in 60% yield. FDMS m/e=313. mp 105°–106°.

EXAMPLE 77

Preparation of 1-(4-indolyloxy)-3-(4-phenylmethylpiperidin-1-yl)-2-propanol ethanedioate The title compound was prepared in similar fashion from 4-(oxiranylmethoxy)-1H-indole and 4-phenylmethylpiperidine. The resulting free base was dissolved in ethyl acetate, and precipitated with one equivalent of oxalic acid in ethyl acetate in 52% overall yield. FDMS m/e=364 ($M^+$ of free base). mp 105°–107°.

EXAMPLE 78

Preparation of (2S)-(−)-1-(4-indolyloxy)-3-(5-methoxyspiro[benzodihydrofuran-1(3H),4'-piperidin]-1'-yl)-2-propanol ethanedioate The title compound was prepared in similar fashion from (S)-(+)-4-(oxiranylmethoxy)-1H-indole and 5-methoxyspiro[benzodihydrofuran-1(3H),4'-piperidine]. The resulting free base was dissolved in ethyl acetate, and precipitated with one equivalent of oxalic acid in ethyl acetate in 86% overall yield. FDMS m/e=408 ($M^+$ of free base). $\alpha[D]_{589}$=−23.58 (c=0.51, methanol).

| analysis | calculated | found |
|---|---|---|
| C | 62.64 | 62.81 |
| H | 6.07 | 6.31 |
| N | 5.62 | 5.90 |

EXAMPLE 79

Preparation of (2S)-(−)-1-(4-indolyloxy)-3-(4-(3,4-ethylenedioxy)phenyl)piperidin-1-yl)-2-propanol ethanedioate The title compound was prepared in similar fashion from (S)-(+)-4-(oxiranylmethoxy)-1H-indole and 4-(3,4-ethylenedioxyphenyl)piperidine. The resulting free base was dissolved in ethyl acetate, and precipitated with one equivalent of oxalic acid in ethyl acetate in 66% overall yield FDMS m/e=408 ($M^+$ of free base). $\alpha[D]_{589}$=−9.39 (c=0.53, methanol).

| analysis | calculated | found |
|---|---|---|
| C | 62.64 | 62.46 |
| H | 6.07 | 5.96 |
| N | 5.62 | 5.39 |

EXAMPLE 80

Preparation of (2S)-(−)-1-(4-indolyloxy)-3-(4-fluorospiro[benzodihydrofuran-1(3H),4'-piperidin]-3-one-1'-yl)-2-propanol ethanedioate The title compound was prepared in similar fashion from (S)-(+)-4-(oxiranylmethoxy)-1H-indole and 4-fluorospiro[benzodihydrofuran-1(3H),4'-piperidin]-3-one. The resulting free base was dissolved in ethyl acetate, and precipitated with one equivalent of oxalic acid in ethyl acetate in 88% overall yield. mp 222°–223°. FDMS m/e=410 ($M^+$ of free base). $\alpha[D]_{589}$=−94.9 (c=0.52, methanol).

| analysis | calculated | found |
|---|---|---|
| C | 62.52 | 62.35 |
| H | 5.25 | 5.29 |
| N | 2.80 | 2.69 |

EXAMPLE 81

Preparation of (2S)-(–)-1-(4-indolyloxy)-3-(benzo[c]spiro[benzodihydrofuran-1(3H),4'-piperidin]-1'-yl)-2-propanol ethanedioate The title compound was prepared in similar fashion from (S)-(+)-4-(oxiranylmethoxy)-1H-indole and benzo[c]spiro[benzodihydrofuran-1(3H),4'-piperidine]. The resulting free base was dissolved in ethyl acetate, and precipitated with one equivalent of oxalic acid in ethyl acetate in 73% overall yield. FDMS m/e=428 ($M^+$ of free base). $\alpha[D]_{589}$=–31.5 (c=0.54, methanol).

| analysis | calculated | found |
|---|---|---|
| C | 67.17 | 67.42 |
| H | 5.83 | 6.04 |
| N | 5.40 | 5.55 |

EXAMPLE 82

Preparation of (2S)-(–)-1-(4-indolyloxy)-3-(3,4-dihydro-2-oxospiro[naphthalene-1(2H),4'-piperidin]-1'-yl)-2-propanol ethanedioate The title compound was prepared in similar fashion from (S)-(+)-4-(oxiranylmethoxy)-1H-indole and 3,4-dihydro-2-oxospiro[naphthalene-1(2H),4'-piperidine]. The resulting free base was dissolved in ethyl acetate, and precipitated with one equivalent of oxalic acid in ethyl acetate in 68% overall yield. FDMS m/e=404 ($M^+$ of free base). $\alpha[D]_{589}$=–15.81 (C=0.51, methanol).

| analysis | calculated | found |
|---|---|---|
| C | 65.58 | 65.33 |
| H | 6.11 | 5.91 |
| N | 5.66 | 5.37 |

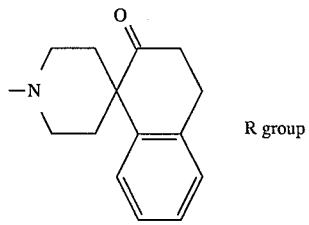

R group

EXAMPLE 83

Preparation of (2S)-(–)-1-(4-indolyloxy)-3-(3,4-dihydro-2-oxo-7-methoxyspiro[naphthalene-1(2H),4'-piperidin]-1'-yl)-2-propanol ethanedioate The title compound was prepared in similar fashion from (S)-(+)-4-(oxiranylmethoxy)-1H-indole and 3,4-dihydro-2-oxo-7-methoxyspiro[naphthalene-1(2H),4'-piperidine]. The resulting free base was dissolved in ethyl acetate, and precipitated with one equivalent of oxalic acid in ethyl acetate in 55% overall yield. FDMS m/e=434 ($M^+$ of free base). $\alpha[D]_{589}$=–5.55 (c=0.54, methanol).

| analysis | calculated | found |
|---|---|---|
| C | 64.11 | 64.40 |
| H | 6.15 | 6.38 |
| N | 5.34 | 5.29 |

EXAMPLE 84

Preparation of (2S)-(–)-1-(4-indolyloxy)-3-(4-chlorospiro[benzodihydrofuran-1(3H),4'-piperidin]-3-one-1'-yl)-2-propanol ethanedioate The title compound was prepared in similar fashion from (S)-(+)-4-(oxiranylmethoxy)-1H-indole and 4-chlorospiro[benzodihydrofuran-1(3H),4'-piperidin]-3-one. The resulting free base was dissolved in ethyl acetate, and precipitated with one equivalent of oxalic acid in ethyl acetate in 49% overall yield. mp 222°–224°. FDMS m/e=426 ($M^+$ of free base). $\alpha[D]_{589}$=–14.95 (c=0.54, methanol).

| analysis | calculated | found |
|---|---|---|
| C | 58.09 | 58.19 |
| H | 4.87 | 4.97 |
| N | 5.42 | 5.53 |

EXAMPLE 85

Preparation of (2S)-(–)-1-(4-indolyloxy)-3-(6-chlorospiro[benzodihydrofuran-1(3H),4'-piperidin]-3-one-1'-yl)-2-propanol ethanedioate The title compound was prepared in similar fashion from (S)-(+)-4-(oxiranylmethoxy)-1H-indole and 6-chlorospiro[benzodihydrofuran-1(3H),4'-piperidin]-3-one. The resulting free base was dissolved in ethyl acetate, and precipitated with one equivalent of oxalic acid in ethyl acetate in 45% overall yield. mp 147°–148°. FDMS m/e=426 ($M^+$ of free base). $\alpha[D]_{589}$=–9.74 (c=0.72, methanol).

| analysis | calculated | found |
|---|---|---|
| C | 58.09 | 58.31 |
| H | 4.87 | 4.73 |
| N | 5.42 | 5.79 |

EXAMPLE 86

Preparation of (2S)-(–)-1-(4-indolyloxy)-3-(benzo[e]spiro[benzodihydrofuran-1(3H),4'-piperidin]-3-one-1'-yl)-2-propanol The title compound was prepared in similar fashion from (S)-(+)-4-(oxiranylmethoxy)-1H-indole and benzo[e]spiro[benzodihydrofuran-1(3H),4'-piperidin]-3-one in yield. mp 170°–172°. FDMS m/e=442 ($M^+$ of free base). $\alpha[D]_{589}$=–38.1 (c=0.55, methanol).

| analysis | calculated | found |
|---|---|---|
| C | 73.29 | 72.97 |
| H | 5.92 | 5.83 |
| N | 6.33 | 6.05 |

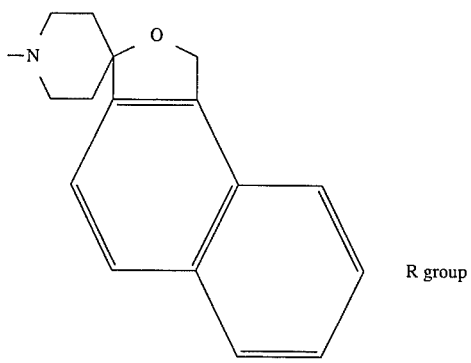

R group

EXAMPLE 87

Preparation of (2S)-(−)-1-(4-indolyloxy)-3-(1,5-dihydrospiro[4H-2-benzopyran-1,4'-piperidin]-1'-yl)-2-propanol ethanedioate The title compound was prepared in similar fashion from (S)-(+)-4-(oxiranylmethoxy)-1H-indole and 1,5-dihydrospiro[4H-2-benzopyran-1,4'-piperidine]. The resulting free base was dissolved in ethyl acetate, and precipitated with one equivalent of oxalic acid in ethyl acetate in 58% overall yield. FDMS m/e=392 ($M^+$ of free base). $[D]_{589}$=−23.56 (c=0.51, methanol).

| analysis | calculated | found |
|---|---|---|
| C | 64.72 | 65.09 |
| H | 6.27 | 6.44 |
| N | 5.81 | 6.14 |

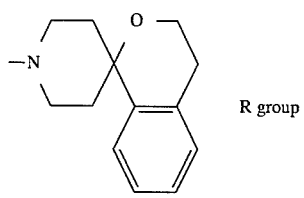

R group

EXAMPLE 88

Preparation of (2S)-(−)-1-(4-indolyloxy)-3-(4-methoxyspiro[benzodihydrofuran-1(3H),4'-piperidin]-3-one-1'-yl)-2-propanol ethanedioate The title compound was prepared in similar fashion from (S)-(+)-4-(oxiranylmethoxy)-1H-indole and 4-methoxyspiro[benzodihydrofuran-1(3H),4'-piperidin]-3-one. The resulting free base was dissolved in ethyl acetate, and precipitated with one equivalent of oxalic acid in ethyl acetate in 83% overall yield. mp 204°–205°. FDMS m/e=422 ($M^+$ of free base). $\alpha[D]_{589}$=−8.62 (c=0.58, methanol).

| analysis | calculated | found |
|---|---|---|
| C | 60.93 | 61.13 |
| H | 5.51 | 5.55 |
| N | 5.47 | 5.69 |

EXAMPLE 89

Preparation of (2S)-(−)-1-(4-indolyloxy)-3-(benzo[e]spiro[benzodihydrofuran-1(3H),4'-piperidin]-1'-yl)-2-propanol ethanedioate The title compound was prepared in similar fashion from (S)-(+)-4-(oxiranylmethoxy)-1H-indole and benzo[e]spiro[benzodihydrofuran-1(3H),4'-piperidine]. The resulting free base was dissolved in ethyl acetate, and precipitated with one equivalent of oxalic acid in ethyl acetate in 83% overall yield. FDMS m/e=428 ($M^+$ of free base). $\alpha[D]_{589}$=−5.65 (c=0.53, methanol).

| analysis | calculated | found |
|---|---|---|
| C | 67.17 | 66.99 |
| H | 5.83 | 5.92 |
| N | 5.40 | 5.66 |

EXAMPLE 90

Preparation of (2S)-(−)-1-(4-indolyloxy)-3-(6-methoxyspiro[benzodihydrofuran-1(3H),4'-piperidin]-3-one-1'-yl)-2-propanol The title compound was prepared in similar fashion from (S)-(+)-4-(oxiranylmethoxy)-1H-indole and 6-methoxyspiro[benzodihydrofuran-1(3H),4'-piperidin]-3-one, in 57% yield. mp 167°–168°. FDMS m/e=422 ($M^+$ of free base). $\alpha[D]_{589}$=−97.0 (c=0.78, methanol).

| analysis | calculated | found |
|---|---|---|
| C | 68.23 | 68.52 |
| H | 6.20 | 6.36 |
| N | 6.63 | 6.41 |

EXAMPLE 91

Preparation of (2S)-(−)-1-(4-indolyloxy)-3-(6-methylspiro[benzodihydrofuran-1(3H),4'-piperidin]-3-one-1'-yl)-2-propanol ethanedioate The title compound was prepared in similar fashion from (S)-(+)-4-(oxiranylmethoxy)-1H-indole and 6-methylspiro[benzodihydrofuran-1(3H),4'-piperidin]-3-one. The resulting free base was dissolved in ethyl acetate, and precipitated with one equivalent of oxalic acid in ethyl acetate in 96% overall yield. mp 227°–228°. FDMS m/e=406 ($M^+$ of free base). $\alpha[D]_{589}$=−93.1 (c=0.57, methanol).

| analysis | calculated | found |
|---|---|---|
| C | 62.90 | 62.66 |
| H | 5.68 | 5.80 |
| N | 5.64 | 5.72 |

EXAMPLE 92

Preparation of (2S)-(−)-1-(4-indolyloxy)-3-(6-methoxyspiro[benzodihydrofuran-1(3H),4'-piperidin]-1'-yl)-2-propanol ethanedioate The title compound was prepared in similar fashion from (S)-(+)-4-(oxiranylmethoxy)-1H-indole and 6-methoxyspiro[benzodihydrofuran-1(3H),4'-piperidine]. The resulting free base was dissolved in ethyl acetate, and precipitated with one equivalent of oxalic acid in ethyl acetate in 59% overall yield. FDMS m/e=408 (M⁺ of free base). α[D]$_{589}$=−7.07 (c=0.56, methanol).

| analysis | calculated | found |
|---|---|---|
| C | 62.64 | 62.79 |
| H | 6.07 | 6.16 |
| N | 5.62 | 5.83 |

EXAMPLE 93

Preparation of (2S)-(−)-1-(4-indolyloxy)-3-(6-methylspiro[benzodihydrofuran-1(3H),4'-piperidin]-1'-yl)-2-propanol ethanedioate The title compound was prepared in similar fashion from (S)-(+)-4-(oxiranylmethoxy)-1H-indole and 6-methylspiro[benzodihydrofuran-1(3H),4'-piperidine]. The resulting free base was dissolved in ethyl acetate, and precipitated with one equivalent of oxalic acid in ethyl acetate in 77% overall yield. FDMS m/e=392 (M⁺ of free base). α[D]$_{589}$=−21.47 (c=0.56, methanol).

| analysis | calculated | found |
|---|---|---|
| C | 64.72 | 63.79 |
| H | 6.27 | 6.28 |
| N | 5.81 | 5.59 |

EXAMPLE 94

Preparation of (2S)-(−)-1-(4-indolyloxy)-3-(4-methoxyspiro[benzodihydrofuran-1(3H),4'-piperidin]-1'-yl)-2-propanol ethanedioate The title compound was prepared in similar fashion from (S)-(+)-4-(oxiranylmethoxy)-1H-indole and 4-methoxyspiro[benzodihydrofuran-1(3H),4'-piperidine]. The resulting free base was dissolved in ethyl acetate, and precipitated with one equivalent of oxalic acid in ethyl acetate in 84% overall yield. FDMS m/e=408 (M⁺ of free base). α[D]$_{589}$=−16.60 (c=0.54, methanol).

| analysis | calculated | found |
|---|---|---|
| C | 62.64 | 62.38 |
| H | 6.07 | 5.91 |
| N | 5.62 | 5.47 |

EXAMPLE 95

Preparation of (2S)-(−)-1-(4-indolyloxy)-3-(spiro[3H-2-benzopyran-3,4'-piperidin]-1(4H)-3-one-1'-yl)-2-propanol ethanedioate The title compound was prepared in similar fashion from (S)-(+)-4-(oxiranylmethoxy)-1H-indole and spiro[3H-2-benzopyran-3,4'-piperidin]-1(4H)-3-one. The resulting free base was dissolved in ethyl acetate, and precipitated with one equivalent of oxalic acid in ethyl acetate in 81% overall yield. FDMS m/e=406 (M⁺ of free base). α[D]$_{589}$=−17.61 (c=0.51, methanol).

| analysis | calculated | found |
|---|---|---|
| C | 62.90 | 62.65 |
| H | 5.68 | 5.44 |
| N | 5.64 | 5.41 |

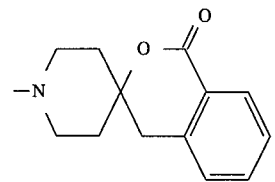

R group

EXAMPLE 96

Preparation of (2S)-(−)-1-(4-indolyloxy)-3-(5-chlorospiro[benzodihydrofuran-1(3H),4'-piperidin]-3-one-1'-yl)-2-propanol ethanedioate The title compound was prepared in similar fashion from (S)-(+)-4-(oxiranylmethoxy)-1H-indole and 5-chlorospiro[benzodihydrofuran-1(3H),4'-piperidin]-3-one. The resulting free base was dissolved in ethyl acetate, and precipitated with one equivalent of oxalic acid in ethyl acetate in 87% overall yield. mp 222°–224° (decomp). FDMS m/e=426 (M⁺ of free base). α[D]$_{589}$=−50.6 (c=0.57, methanol).

| analysis | calculated | found |
|---|---|---|
| C | 58.09 | 58.36 |
| H | 4.87 | 4.73 |
| N | 5.42 | 5.57 |

EXAMPLE 97

Preparation of (2S)-(−)-1-(4-indolyloxy)-3-(5-chlorospiro[benzodihydrofuran-1(3H),4'-piperidin]-1'-yl)-2-propanol ethanedioate The title compound was prepared in similar fashion from (S)-(+)-4-(oxiranylmethoxy)-1H-indole and 5-chlorospiro[benzodihydrofuran-1(3H),4'-piperidine]. The resulting free base was dissolved in ethyl acetate, and precipitated with one equivalent of oxalic acid in ethyl acetate in 77% overall yield. FDMS m/e=412 (M⁺ of free base). α[D]$_{589}$=−19.80 (c=0.50, methanol).

| analysis | calculated | found |
|---|---|---|
| C | 59.70 | 59.53 |
| H | 5.41 | 5.42 |
| N | 5.57 | 5.67 |

EXAMPLE 98

Preparation of (2S)-(−)-1-(4-indolyloxy)-3-(1,4-dihydrospiro[3H-2-benzopyran-3,4'-piperidin]-1'-yl)-2-propanol ethanedioate The title compound was prepared in similar fashion from (S)-(+)-4-(oxiranylmethoxy)-1H-indole and 1,4-dihydrospiro[3H-2-benzopyran-3,4'-piperidine]. The resulting free base was dissolved in ethyl acetate, and precipitated with one equivalent of oxalic acid in ethyl acetate in 78% overall yield. FDMS m/e=392 ($M^+$ of free base). $\alpha[D]_{589}$= −12.34 (c=0.57, methanol).

| analysis | calculated | found |
|---|---|---|
| C | 64.72 | 64.75 |
| H | 6.27 | 6.08 |
| N | 5.81 | 5.82 |

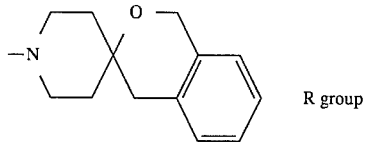

R group

EXAMPLE 99

Preparation of 1-(4-indolyloxy)-3-(spiro[3H-2-benzopyran-3,4'-piperidin]-1(4H)-3-one-1'-yl)propane ethanedioate A solution of 1-chloro-3-(1H-indole-4-oxy)propane, spiro [3H-2-benzopyran-3,4'-piperidin]-1(4H)-3-one and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 53% overall yield. FDMS m/e=390 ($M^+$ of free base).

| analysis | calculated | found |
|---|---|---|
| C | 64.99 | 65.28 |
| H | 5.87 | 5.95 |
| N | 5.83 | 5.99 |

EXAMPLE 100

Preparation of 1-(4-indolyloxy)-3-(1-adamantylamino)-2-propanol hydrochloride

A mixture of 4-(oxiranylmethoxy)-1H-indole (0.946 g, 5 mmol) and 1-adamantylamine (1.51 g, 10 mmol) in methanol (25 mL) was heated to reflux for 18 h. The methanol was evaporated and flash chromatography [silica gel, methylene chloride/methanol/ammonium hydroxide (100/10/0.5)] yielded 1.49 g solid. Crystallization as the hydrochloride salt from ethyl acetate/methanol provided 1.47 g of colorless crystals (one mole of ethyl acetate bound to crystals). Mp 159°–161° C. Mass spectrum, $m^+$=340. Anal ($C_{25}H_{37}ClN_2O_4$) theory C, 64.57; H, 8.02; N, 6.02; found C, 64.71; H, 7.88; N, 6.30.

EXAMPLE 101

Preparation of (2S)-(−)-1-(4-indolyloxy)-3-(1-adamantylamino)-2-propanol hydrochloride A mixture of (S)-(+)-4-(oxiranylmethoxy)-1H-indole (1.89 g, 10 mmol) and 1-adamantylamine (1.66 g, 11 mmol) in methanol (50 mL) was heated to reflux for 18 h. The methanol was evaporated and flash chromatography [silica gel, methylene chloride/methanol/ammonium hydroxide (100/10/0.5)] yielded 2.40 g solid. Crystallization as the hydrochloride salt from ethyl acetate/methanol provided 1.68 g of colorless crystals (one mole of ethyl acetate bound to crystals). Mp 94° C. Mass spectrum, $m^+$=341. $[\alpha]^{23}_{365}$= −52.4° (C=0.01 g/mL, MeOH). Anal ($C_{25}H_{37}ClN_2O_4$) theory C, 64.57; H, 8.02; N, 6.02; found C, 64.80; H, 8.04; N, 6.22.

EXAMPLE 102

Preparation of 1-(4-indolyloxy)-3-(2-adamantylamino)-2-propanol hydrochloride

A mixture of 4-(oxiranylmethoxy)-1H-indole (0.927 g, 4.9 mmol) and 2-adamantylamine (0.808 g, 5.3 mmol) in methanol (25 mL) was heated to reflux for 18 h. The methanol was evaporated and flash chromatography [silica gel, methylene chloride/methanol (85/15)] yielded 0.855 g oil. Crystallization as the hydrochloride salt from ethyl acetate/methanol provided 0.62 g of colorless crystals. Mp>250° C. Mass spectrum, $m^+$=340. Anal ($C_{21}H_{29}ClN_2O_2$) theory C, 66.92; H, 7.75; N, 7.43; found C, 66.92; H, 7.78; N, 7.27.

EXAMPLE 103

Preparation of (2R)-(+)-1-(4-indolyloxy)-3-(1-adamantylamino)-2-propanol hydrochloride A mixture of (R)-(−)-4-(oxiranylmethoxy)-1H-indole (1.89 g, 10 mmol) and 1-adamantylamine (1.66 g, 11 mmol) in methanol (50 mL) was heated to reflux for 18 h. The methanol was evaporated and flash chromatography [silica gel, methylene chloride/methanol/ammonium hydroxide (100/10/0.5)] yielded 2.54 g oil. Crystallization as the hydrochloride salt from ethyl acetate/methanol provided 1.52 g of colorless crystals (one mole of ethyl acetate bound to crystals). Mp 95° C. Mass spectrum, $m^+$=340. $[\alpha]^{23}_{365}$= +46.1° (C=0.01 g/mL, MeOH). Anal ($C_{25}H_{37}ClN_2O_4$) theory C, 64.57; H, 8.02; N, 6.02; found C, 64.65; H, 7.79; N, 6.25.

EXAMPLE 104

Preparation of (2S)-(−)-1-(4-indolyloxy)-3-(2-adamantylamino)-2-propanol hydrochloride A mixture of (S)-(+)-4-(oxiranylmethoxy)-1H-indole (1.89 g, 10 mmol) and 2-adamantylamine (1.66 g, 11 mmol) in methanol (50 mL) was heated to reflux for 18 h. The methanol was evaporated to an oil and crystallization as the hydrochloride salt from ethyl acetate/methanol provided 1.45 g of colorless crystals Mp>250° C. Mass spectrum, $m^+$=340. $[\alpha]^{23}_{365}$=−48.8° (C=0.0032 g/mL, MeOH). Anal ($C_{21}H_{29}ClN_2O_2$) theory C, 66.92; H, 7.76; N, 7.43; found C, 66.64; H, 7.83; N, 7.61.

EXAMPLE 105

Preparation of 1-(4-indolyloxy)-3-(1-adamantylmethylamino)-2-propanol hydrochloride A mixture of 4-(oxiranylmethoxy)-1H-indole (0.568 g, 3 mmol) and 1-adamantylmethylamine (0.545 g, 3.3 mmol) in methanol (25 mL) was heated to reflux for 18 h. The methanol was evaporated and flash chromatography [silica gel, methylene chloride/methanol (90/10)] yielded 0.527 g oil. Crystallization as the hydrochloride salt from ethyl acetate/methanol provided 0.277 g of colorless crystals Mp 228° C. Mass spectrum, m$^+$=354. Anal (C$_{22}$H$_{31}$ClN$_2$O$_2$) theory C, 67.59; H, 7.99; N, 7.17; found C, 67.55; H, 8.16; N, 7.37.

EXAMPLE 106

Preparation of 1-(4-indolyloxy)-3-[4-(2-methoxyphenyl)-1-piperazinyl]-2-propanol dihydrochloride A mixture of 4-(oxiranylmethoxy)-1H-indole (0.946 g, 5 mmol) and 1-(2-methoxyphenyl)piperazine (1.05 g, 5.5 mmol) in methanol (30 mL) was heated to reflux for 18 h. The methanol was evaporated and flash chromatography [silica gel, methylene chloride/methanol (97/3)] yielded 1.75 g oil. Crystallization as the dihydrochloride salt from ethyl acetate/methanol provided 1.56 g of colorless crystals. Mp 108° C. Mass spectrum, m$^+$=381. Exact mass, theory 382.2131; found 382.2157.

EXAMPLE 107

Preparation of (2R)-(+)-1-(4-indolyloxy)-3-(2-adamantylamino)-2-propanol hydrochloride A mixture of (R)-(–)-4-(oxiranylmethoxy)-1H-indole (0.946 g, 5 mmol) and 2-adamantylamine (0.80 g, 5.25 mmol) in methanol (30 mL) was heated to reflux for 18 h. The methanol was evaporated t o an oil and crystallization as the hydrochloride sa it from ethanol provided 0.60 g of off-white crystals. Mp>250° C. Mass spectrum, m$^+$=340. [α]$^{23}_{365}$=+41.8° (C=0.01 g/mL, MeOH). Anal (C$_{21}$H$_{29}$ClN$_2$O$_2$) theory C, 66.92; H, 7.75; N, 7.43; found C, 66.97; H, 7.89; N, 7.42.

EXAMPLE 108

Preparation of (2S)-(–)-1-(4-indolyloxy)-3-[4-(2-methoxyphenyl)-1-piperazinyl]-2-propanol dihydrochloride A mixture of (S)-(+)-4-(oxiranylmethoxy)-1H-indole (1.89 g, 10 mmol) and 1-(2-methoxyphenyl)piperazine (2.11 g, 11 mmol) in methanol (75 mL) was heated to reflux for 18 h. The methanol was evaporated and flash chromatography (silica gel, ethyl acetate) yielded 3.52 g oil. Crystallization as the dihydrochloride salt in ethyl acetate provided 3.84 g of colorless crystals Mp 176° C. Mass spectrum, m$^+$=382. [α]$^{23}_{365}$=–37.1° (C=0.01 g/mL, MeOH). Anal (C$_{22}$H$_{29}$Cl$_2$N$_3$O$_3$) theory C, 58.15; H, 6.43; N, 9.25; found C, 58.44; H, 6.46; N, 9.17

EXAMPLE 109

Preparation of (2S)-(–)-1-(4-indolyloxy)-3-(1-adamantylmethylamino)-2-propanol hydrochloride A mixture of (S)-(+)-4-(oxiranylmethoxy)-1H-indole (0.946 g, 5 mmol) and 1-adamantylmethylamine (0.91 g, 5.5 mmol) in methanol (30 mL) was heated to reflux for 18 h. The methanol was evaporated and flash chromatography [silica gel, methylene chloride/methanol (90/10)] yielded 1.18 g oil. Crystallization as the hydrochloride salt from 2-propanol provided 0.711 g crystals. Mp 118° C. Mass spectrum, m$^+$=354. [α]$^{23}_{365}$=–41.3° (C=0.0075 g/mL, MeOH). Anal (C$_{22}$H$_{31}$ClN$_2$O$_2$) theory C, 67.59; H, 7.99; N, 7.16; found C, 67.68; H, 8.09; N, 6.95.

EXAMPLE 110

Preparation of (2S)-(–)-1-(4-indolyloxy)-3-[4-(2-pyrimidinyl)-1-piperazinyl]-2-propanol dihydrochloride A mixture of (S)-(+)-4-(oxiranylmethoxy)-1H-indole (1.65 g, 8.7 mmol) and 1-(2-pyrimidinyl)piperazine (1.58 g, 9.6 mmol) in methanol (75 mL) was heated to reflux for 18 h. The methanol was evaporated and flash chromatography [silica gel, ethyl acetate/ethanol (95/5)] yielded 2.81 g oil. Crystallization as the dihydrochloride salt from methanol provided 0.767 g of light yellow crystals. Mp 240° C. Mass spectrum m$^+$=353 [α]$^{23}_{589}$=–16.8° (C=0.01 g/mL MeOH). Anal (C$_{19}$H$_{25}$Cl$_2$N$_5$O$_2$) theory C, 53.53; H, 5.91; N, 16.43; found C, 53.46; H, 5.94; N, 16.49.

EXAMPLE 111

Preparation of (2S)-(–)-1-(4-indolyloxy)-3-[4-(1-naphthyl)-1-piperazinyl]-2-propanol hydrochloride A mixture of (S)-(+)-4-(oxiranylmethoxy)-1H-indole (1.72 g, 9.1 mmol) and 1-(1-naphthyl)piperazine [see J. Med. Chem. 29, 2375 (1986)] (2.12 g, 10 mmol) in methanol (75 mL) was heated to reflux for 18 h. The methanol was evaporated and flash chromatography (silica gel, ethyl acetate) yielded 1.86 g oil. Crystallization as the hydrochloride salt from methanol/diethyl ether provided 1.32 g of colorless crystals. Mp 140° C. Mass spectrum, m$^+$=401. [α]$^{23}_{365}$=–41.9° (C=0.0077 g/mL, MeOH). Anal (C$_{25}$H$_{28}$ClN$_3$O$_2$) theory C, 68.56; H, 6.44; N, 9.59; found C, 68.46; H, 6.59; N, 9.58.

EXAMPLE 112

Preparation of (2S)-(–)-1-(4-indolyloxy)-3-(3,5,7-trimethyl-1-adamantylamino)-2-propanol hydrochloride A mixture of (S)-(+)-4-(oxiranylmethoxy)-1H-indole (0.511 g, 2.7 mmol) and 3,5,7-trimethyl-1-adamantylamine (0.587 g, 3 mmol) in methanol (15 mL) was heated to reflux for 18 h. The methanol was evaporated and flash chromatography [silica gel, methylene chloride/methanol/ammonium hydroxide (100/5/0.5)] yielded 0.722 g solid foam. Crystallization as the hydrochloride salt in ethyl acetate provided 0.728 g of colorless crystals. Mp>250° C. Mass spectrum, m$^+$=382. [α]$^{23}_{365}$=–63.7° (C=0.0076 g/mL MeOH). Anal (C$_{24}$H$_{35}$ClN$_2$O$_2$) theory C, 68.80; H, 8.42; N, 6.69; found C, 68.60; H, 8.63; N, 6.60.

EXAMPLE 113

Preparation of (2S)-(–)-1-(4-indolyloxy)-3-(1-methyl-1-adamantylamino)-2-propanol hydrochloride A mixture of (S)-(+)-4-(oxiranylmethoxy)-1H-indole (0.511 g, 2.7 mmol) and 1-methyl-1-adamantylamine (see Org. Syn., Coll. Vol. 7, 433) (0.486 g, 2.9 mmol) in methanol (15 mL) was heated to reflux for 18 h. The methanol was evaporated and flash chromatography [silica gel, methylene chloride/methanol/ammonium hydroxide (100/3/0.5)] yielded 0.787 g oil. Crystallization as the hydrochloride salt from acetonitrile provided 0.623 g of colorless crystals. Mp 241° C. Mass spectrum, m$^+$=355. [α]$^{23}_{589}$=–16.6° (C=0.0073 g/mL, MeOH). Anal (C$_{22}$H$_{31}$ClN$_2$O$_2$) theory C, 67.58; H, 7.99; N, 7.17; found C, 67.35; H, 8.18; N, 7.15.

EXAMPLE 114

Preparation of (2S)-(–)-1-(4-indolyloxy)-3-[4-(5-methoxy-4-pyrimidinyl)-1-piperazinyl]-2-propanol dihydrochloride monohydrate A mixture of (S)-(+)-4-(oxiranylmethoxy)-1H-indole (0.946 g, 5 mmol) and 1-(5-methoxy-4-pyrimidinyl)piperazine (see European Patent App. 92121519.0) (1.07 g, 5.5 mmol) in methanol (30 mL) was heated to reflux for 18 h. The methanol was evaporated and flash chromatography [silica gel, methylene chloride/methanol (93/7)] yielded 0.873 g oil. Crystallization as the dihydrochloride monohydrate salt from methanol provided 0.625 g of colorless crystals Mp 222° C. Mass spectrum, m+=383. $[\alpha]^{23}_{589}$=–27.2° (C=0.0076 g/mL, MeOH). Anal ($C_{20}H_{29}Cl_2N_5O_4$) theory C, 50.64; H, 6.16; N, 14.76; found C, 50.77; H, 6.08; N, 14.53.

EXAMPLE 115

Preparation of (2S)-(–)-1-(4-indolyloxy)-3-(8-[1-phenyl-1,3,8-triazaspiro[4.5]decan-4-one])-2-propanol, maleate A mixture of (S)-(+)-4-(oxiranylmethoxy)-1H-indole (1.8 g, 9.5 mmol) and 1-phenyl-1,3,8-triazospiro[4,5]decan-4-one (2.2 g, 9.5 mmol) in methanol (25 mL) was heated to reflux for 18 h. The methanol was removed under reduced pressure. Preparative liquid chromatography [Waters Prep LC/500 A, Prep PAK-500/silica gel cartridge, 8 L gradient, methylene chloride/methanol/ammonium hydroxide (95/5/0.5)] yielded 3.3 g (82.5%) of a white foam. Crystallization as the maleate salt from ethyl acetate/methanol provided 0.7 g of pale yellow needles. mp 205°–206° C. mass spectrum (70 eV), m/e (relative intensity) 421 (M+1, 100); $[\alpha]_D^{23}$ –9.2° (c=1, MeOH), $[\alpha]_{365}^{23}$ –21.5° (C=1, MeOH). Anal ($C_{28}H_{32}N_4O_7$) Theory C, 62.68; H, 6.01; N, 10.44; Found C, 62.40; H, 5.97; N, 10.70.

EXAMPLE 116

Preparation of (2R)-(+)-1-(4-indolyloxy)-3-(8-[1-phenyl-1,3,8-triazaspiro[4.5]decan-4-one])-2-propanol, maleate The title compound was prepared in the same manner as the Example above, in 73.8% yield. Crystallization as the maleate salt from ethyl acetate/methanol provided 2.7 g of a white powder. mp 201°–202° C. mass spectrum (70 eV), m/e (relative intensity) 421 (M+1, 100); $[\alpha]_D^{23}$ +9.5° (C=1, MeOH), $[\alpha]_{365}^{23}$ +25.4° (c=1, MeOH) Anal ($C_{28}H_{32}N_4O_7$) Theory C, 62.68; H, 6.01; N, 10.44; Found C, 62.95; H, 6.30; N, 10.20.

Preparation 19

Preparation of 1-(1H-indole-4-oxy)-3-tosylate)-2-methoxypropane

A solution of dimethyl 2-methoxymalonate 14.6 ml, 105 mmol) in dry tetrahydrofuran (70 mL) was added dropwise to a 7° slurry of lithium aluminum hydride (10.0 g, 262 mmol) in dry tetrahydrofuran (160 mL). The resulting mixture was stirred 18 h at room temperature. The reaction mixture was cooled to 0° and the excess lithium aluminum hydride was quenched by the dropwise addition of a saturated sodium sulfate solution. Filtration and concentration of the filtrate provided 4.45 g of crude product. The filter cake was triturated with refluxing tetrahydrofuran for 18 h to provide an additional 4.2 g of crude product. This material was combined with the product of a previous reaction to give 10.55 g of crude product. Distillation yielded 7.5 g (54.3%) of homogeneous product as a clear colorless oil. bp 109°–112° at 4.5 torr. Anal ($C_4H_{10}O_3$) Theory C, 45.27; H, 9.50; Found C, 45.55; H, 9.45.

A mixture of the above 1,3-dihydroxy-2-methoxypropane (7.24 g, 68.2 mmol) and p-toluenesulfonyl chloride (29.9 g, 157 mmol) in pyridine (100 mL) was stirred 5 h at 0° and let stand at 0° for 18 h. Product isolation (water/ice, ethyl acetate, cold 5N hydrochloric acid, water, brine, sodium sulfate) yielded 27.5 g (97.2%) of a pale yellow oil. Mass spectrum (70 eV), m/e (relative intensity) 414 (M+, 100); Anal ($C_{18}H_{22}O_7S_2$) Theory C, 52.16; H, 5.35; Found C, 52.37; H, 5.42.

A solution of 4-hydroxyindole (6.94 g, 52.1 mmol) in dry dimethylformamide (80 mL) was added dropwise to a slurry of sodium hydride (2.2 g of a 60% dispersion in oil, 54.7 mmol) in dry dimethylformamide (20 mL). The resulting mixture was stirred one hour at room temperature. This mixture was added dropwise to a solution of the above 1,3-ditosylate-2-methoxypropane (27 g, 65.1 mmol) in dimethylformamide (155 mL) at 0°. The reaction was stirred at room temperature for 16 h. Product isolation (water, ether/ethyl acetate, water, brine, sodium sulfate) and flash chromatography (silica gel, methylene chloride) provided 17.9 g (91.3%) of product as a colorless oil. Mass spectrum (70 eV), m/e (relative intensity) 375 (M+, 100).

EXAMPLE 117

Preparation of 1-(4-indolyloxy)-3-(1-adamantylamino)-2-methoxypropane ethanedioate A mixture of 1-(1H-indole-4-oxy)-3-(tosylate)-2-methoxypropane (4.5 g, 11.9 mmol) and 1-adamantylamine (5.4 g, 35.7 mmol) in dimethylformamide (30 mL) was heated to 85° C. for 18 h. Product isolation (water, diethyl ether, water, brine, sodium sulfate) yielded 5.0 g of crude product. Preparative liquid chromatography [Waters Prep LC/500 A, Prep PAK-500/silica gel cartridge, 8 L gradient, methylene chloride/methanol/ammonium hydroxide (95/5/0.5)] yielded 2.28 g (54.0%) of a yellow foam. Crystallization as the oxalate salt from ethyl acetate provided 2.54 g of an off white powder. mp 132°–134° C. mass spectrum (70 eV), m/e (relative intensity) 355 (M+1, 100). Anal ($C_{24}H_{32}N_2O_6$) Theory C, 64.85; H, 7.26; N, 6.30; Found C, 64.82; H, 7.28; N, 6.23.

EXAMPLE 118

Preparation of (2S)-(–)-1-(4-indolyloxy)-3-(4-hydroxy-4-(4-fluorobiphenyl)piperidin-1-yl)-2-propanol ethanedioate To a solution of (2S)-(–)-1-(1H-indole-4-oxy)-3-(4-hydroxy-4-(4-bromophenyl)piperidin-1-yl)-2-propanol (250 mg, 0.56 mmol) in 2 mL of toluene and 0.1 mL of methanol was added tetrakis(triphenylphosphine) palladium (0) (0.02 equiv., 13 mg), 4-fluorophenylboronic acid ((1.2 equiv., 94 mg), and 0.6 mL of 2M $Na_2CO_3$ solution, and the mixture was heated at 80° C. for 20 h. The solution was cooled, diluted with a solution of dichloromethane/methanol/aqueous ammonium hydroxide (100:10:1) and the organic phase was separated and washed with 2M $Na_2CO_3$ and brine, and dried over sodium sulfate. The resulting oil was purified by silica gel chromatography (dichloromethane-5% methanol in dichloromethane gradient) to give the free base as a white foam which was dissolved in ethyl acetate and precipitated with one equivalent of oxalic acid in ethyl acetate, to give the title compound in 63% overall yield. mp. 123°–124° C. FDMS m/e=460 (M$^+$ of free base). $\alpha[D]_{589}$=−8.89 (c=0.89, methanol).

| analysis | calculated | found |
|---|---|---|
| C | 65.44 | 65.41 |
| H | 5.67 | 5.95 |
| N | 5.09 | 4.73 |

EXAMPLE 119

Preparation of (2S)-(−)-1-(4-indolyloxy)-3-(4-hydroxy-4-(3-trifluoromethylbiphenyl)piperidin-1-yl)-2-propanol ethanedioate The title compound was prepared as described above, via palladium-mediated coupling of (2S)-(−)-1-(1H-indole-4-oxy)-3-(4-hydroxy-4-(4-bromophenyl)piperidin-1-yl)-2-propanol and 3-trifluoromethylphenylboronic acid. The resulting free base was dissolved in ethyl acetate and precipitated with one equivalent of oxalic acid in ethyl acetate, to give the title compound in 58% overall yield. mp. 132°–134° C. FDMS m/e=510 (M$^+$ of free base). $\alpha[D]_{589}$=−8.47 (c=1.06, methanol).

| analysis | calculated | found |
|---|---|---|
| C | 62.00 | 62.16 |
| H | 5.20 | 5.49 |
| N | 4.66 | 4.49 |

EXAMPLE 120

Preparation of (2S)-(−)-1-(4-indolyloxy)-3-(4-hydroxy-4-(4-methoxybiphenyl)piperidin-1-yl)-2-propanol ethanedioate The title compound was prepared as described previously, via palladium-mediated coupling of (2S)-(−)-1-(1H-indole-4-oxy)-3-(4-hydroxy-4-(4-bromophenyl)piperidin-1-yl)-2-propanol and 4-methoxyphenylboronic acid. The resulting free base was dissolved in ethyl acetate and precipitated with one equivalent of oxalic acid in ethyl acetate, to give the title compound in 39% overall yield. mp. 175°–176° C. FDMS m/e=472 (M$^+$ of free base). $\alpha[D]_{589}$=−4.84 (c=1.03, methanol).

| analysis | calculated | found |
|---|---|---|
| C | 66.18 | 66.34 |
| H | 6.09 | 5.95 |
| N | 4.98 | 4.79 |

EXAMPLE 121

Preparation of 1-(4-indolyloxy)-3-(5-methoxyspiro[benzodihydrofuran-1(3H),4'-piperidin]-3-one-1'-yl)propane ethanedioate A solution of 1-chloro-3-(1H-indole-4-oxy)propane, 5-methoxyspiro[benzodihydrofuran-1(3H),4'-piperidin]-3-one and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 74% overall yield. mp 210°–211°. FDMS m/e=406 (M$^+$ of free base).

| analysis | calculated | found |
|---|---|---|
| C | 62.90 | 62.92 |
| H | 5.68 | 5.70 |
| N | 5.64 | 5.56 |

EXAMPLE 122

Preparation of 1-(4-indolyloxy)-3-(6-chlorospiro[benzodihydrofuran-1(3H),4'-piperidin]-3-one-1'-yl)propane ethanedioate A solution of 1-chloro-3-(1H-indole-4-oxy)propane, 6-chlorospiro[benzodihydrofuran-1(3H),4'-piperidin]-3-one and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 28% overall yield. FDMS m/e=410 (M$^+$ of free base).

| analysis | calculated | found |
|---|---|---|
| C | 59.94 | 60.06 |
| H | 5.03 | 5.19 |
| N | 5.59 | 5.76 |

EXAMPLE 123

Preparation of 1-(4-indolyloxy)-3-(5-methoxyspiro[benzodihydrofuran-1(3H),4'-piperidin]-1'-yl)propane ethanedioate A solution of 1-chloro-3-(1H-indole-4-oxy)propane, 5-methoxyspiro[benzodihydrofuran-1(3H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 62% overall yield. mp 181° (decomp.) FDMS m/e=392 (M$^+$ of free base).

| analysis | calculated | found |
|---|---|---|
| C | 64.72 | 64.42 |
| H | 6.27 | 6.35 |
| N | 5.81 | 5.62 |

EXAMPLE 124

Preparation of 1-(4-indolyloxy)-3-(6-chlorospiro[benzodihydrofuran-1(3H),4'-piperidin]-1-yl)propane ethanedioate A solution of 1-chloro-3-(1H-indole-4-oxy)propane, 6-chlorospiro[benzodihydrofuran-1(3H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 50% overall yield. FDMS m/e=396 ($M^+$ of free base).

| analysis | calculated | found |
|---|---|---|
| C | 61.66 | 61.67 |
| H | 5.59 | 5.67 |
| N | 5.75 | 5.72 |

EXAMPLE 125

Preparation of 1-(4-indolyloxy)-3-(3,4-dihydro-2-oxospiro[naphthalene-1(2H),4'-piperidin]-1'-yl)propane ethanedioate A solution of 1-chloro-3-(1H-indole-4-oxy)propane, 3,4-dihydro-2-oxospiro[naphthalene-1(2H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 37% overall yield. FDMS m/e=388 ($M^+$ of free base).

| analysis | calculated | found |
|---|---|---|
| C | 67.77 | 67.58 |
| H | 6.32 | 6.49 |
| N | 5.85 | 5.89 |

EXAMPLE 126

Preparation of 1-(4-indolyloxy)-3-(4-methoxyspiro[benzodihydrofuran-1(3H),4'-piperidin]-1'-yl)propane ethanedioate A solution of 1-chloro-3-(1H-indole-4-oxy)propane, 4-methoxyspiro[benzodihydrofuran-1(3H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 54% overall yield. FDMS m/e=392 ($M^+$ of free base).

| analysis | calculated | found |
|---|---|---|
| C | 64.72 | 64.98 |
| H | 6.27 | 6.29 |
| N | 5.81 | 5.62 |

EXAMPLE 127

Preparation of 1-(4-indolyloxy)-3-(6-methoxyspiro[benzodihydrofuran-1(3H),4'-piperidin]-1'-yl)propane ethanedioate A solution of 1-chloro-3-(1H-indole-4-oxy)propane, 6-methoxyspiro[benzodihydrofuran-1(3H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 58% overall yield. FDMS m/e=392 ($M^+$ of free base).

| analysis | calculated | found |
|---|---|---|
| C | 64.72 | 65.00 |
| H | 6.27 | 6.34 |
| N | 5.81 | 6.01 |

EXAMPLE 128

Preparation of 1-(4-indolyloxy)-3-(6-methylspiro[benzodihydrofuran-1(3H),4'-piperidin]-3-one -1'-yl)propane ethanedioate A solution of 1-chloro-3-(1H-indole-4-oxy)propane, 6-methylspiro[benzodihydrofuran-1(3H),4'-piperidin]-3-one and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 56% overall yield FDMS m/e=390 ($M^+$ of free base).

| analysis | calculated | found |
|---|---|---|
| C | 64.99 | 65.08 |
| H | 5.87 | 6.14 |
| N | 5.83 | 6.06 |

EXAMPLE 129

Preparation of 1-(4-indolyloxy)-3-(6-methylspiro[benzodihydrofuran-1(3H),4'-piperidin]-1'-yl)propane ethanedioate A solution of 1-chloro-3-(1H-indole-4-oxy)propane, 6-methylspiro[benzodihydrofuran-1(3H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 27% overall yield. FDMS m/e=376 ($M^+$ of free base).

| analysis | calculated | found |
|---|---|---|
| C | 66.94 | 67.15 |
| H | 6.48 | 6.64 |
| N | 6.00 | 6.23 |

EXAMPLE 130

Preparation of 1-(4-indolyloxy)-3-(5-chlorospiro [benzodihydrofuran-1(3H),4'-piperidin]-3-one-1'-yl)propane ethanedioate A solution of 1-chloro-3-(1H-indole-4-oxy propane, 5-chlorospiro[benzodihydrofuran-1(3H),4'-piperidin]-3-one and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 46% overall yield. mp 214°–217° (decomp.) FDMS m/e=410 ($M^+$ of free base).

| analysis | calculated | found |
|---|---|---|
| C | 59.94 | 60.12 |
| H | 5.03 | 5.12 |
| N | 5.59 | 5.89 |

EXAMPLE 131

Preparation of 1-(4-indolyloxy)-3-(5-chlorospiro [benzodihydrofuran-1(3H),4'-piperidin]-1'-yl)propane ethanedioate A solution of 1-chloro-3-(1H-indole-4-oxy)propane, 5-chlorospiro[benzodihydrofuran-1(3H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 58% overall yield. mp 200°–202°. FDMS m/e=396 ($M^+$ of free base).

| analysis | calculated | found |
|---|---|---|
| C | 61.66 | 61.66 |
| H | 5.59 | 5.70 |
| N | 5.75 | 5.69 |

EXAMPLE 132

Preparation of 1-(4-indolyloxy)-3-(1,4-dihydrospiro [3H-2-benzopyran-3,4'-piperidin]-1'-yl)propane ethanedioate A solution of 1-chloro-3-(4-indolyloxy)propane, 1,4-dihydrospiro[3H-2-benzopyran-3,4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 62% overall yield. FDMS m/e=376 ($M^+$ of free base).

| analysis | calculated | found |
|---|---|---|
| C | 66.94 | 66.14 |
| H | 6.48 | 6.44 |
| N | 6.00 | 6.00 |

EXAMPLE 133

Preparation of 1-(4-indolyloxy)-3-(4-phenyl-1-piperidinyl)propane oxalate

A mixture of 1-(1H-indole-4-oxy)-3-chloropropane (0.420 g, 2 mmol), 4-phenylpiperidine (0.322 g, 2 mmol), sodium carbonate (0.530 g, 5 mmol) and 10 mL dimethylformamide was heated at 100° C. for 18 h. Evaporation of dimethylformamide, dilution with methylene chloride, washing with water and drying (sodium sulfate) yielded 0.759 g oil. Flash chromatography [silica gel, methylene chloride/methanol (93/7)] yielded 0.509 g oil. Crystallization as the oxalate salt from ethanol provided 0.297 g of light yellow crystals. Mp 137°–139° C. Mass spectrum, $m^+$=334. Anal ($C_{24}H_{28}N_2O_5$) theory C, 67.91; H, 6.65; N, 6.60; found C, 68.00; H, 6.52; N, 6.76.

EXAMPLE 134

Preparation of 1-(4-indolyloxy)-3-[4-(2-methoxyphenyl)-1-piperazinyl]propane oxalate A mixture of 1-(1H-indole-4-oxy)-3-chloropropane (0.420 g, 2 mmol), 1-(2-methoxyphenyl)piperazine (0.384 g, 2 mmol), sodium carbonate (0.530 g, 5 mmol) and 10 mL dimethylformamide was heated at 100° C. for 18 h. Evaporation of dimethylformamide, dilution with methylene chloride, washing with water and drying (sodium sulfate) yielded 0.819 g oil. Flash chromatography [silica gel, methylene chloride/methanol (95/5)] yielded 0.629 g oil. Crystallization as the oxalate salt in ethyl acetate provided 0.309 g of colorless crystals. Mp 100° C. Mass spectrum, $m^+$=365. Anal ($C_{24}H_{29}N_3O_6$) theory C, 63.28; H, 6.42; N, 9.22; found C, 63.02; H, 6.33; N, 9.38.

EXAMPLE 135

Preparation of 4-(1-adamantylamino)-1-(4-indolyloxy)-3-butanol hydrochloride

Diethyl azodicarboxylate (12.5 ml, 79.3 mmol) was added dropwise to a 5° C. solution of 4-hydroxy-1H-indole (10.56 g, 79.3 mmol), 1,2-epoxy-4-butanol (6.99 g, 79.3 mmol) and triphenylphosphine (20.8 g, 79.3 mmol) in dry tetrahydrofuran (150 mL). The resulting mixture was stirred eighteen hours at room temperature. The tetrahydrofuran was removed under reduced pressure. The residue was diluted with diethyl ether and filtered to remove impurities. The diethyl ether was removed under reduced pressure to give 54.1 g of a brown oil, which was purified by preparative liquid chromatography [Waters Prep LC/500 A, Prep PAK-500/silica gel cartridge, 8L gradient, methylene chloride/methanol/ammonium hydroxide (99/1/0.5) to (97/3/0.5)] to obtain 3.5 g (21.7%) of a clear colorless oil. mass spectrum (70 eV), m/e (relative intensity) 203 ($M^+$, 100).

A mixture of the 1,2-epoxy-4-(1H-indol-4-yloxy)butane (1.52 g, 7.5 mmol) prepared above and 1-adamantylamine (1.25 g, 8.2 mmol) in methanol (20 mL) was heated to reflux for 18 h. The methanol was removed under reduced pressure to yield a white solid. Preparative liquid chromatography [Waters Prep LC/500 A, Prep PAK-500/silica gel cartridge, 8L gradient, methylene chloride/methanol/ammonium hydroxide (95/5/0.5)] yielded 2.0 g (75.5%) of a white solid. Crystallization as the hydrochloride salt from ethyl acetate/methanol provided 1.46 g of an off white powder. mp 260°–2° C. mass spectrum (70 eV), m/e (relative intensity) 354 ($M^+$, 100). Anal ($C_{22}H_{30}N_2O_2 \cdot HCl$) Theory C, 67.59; H, 7.99; N, 7.17; Found C, 67.55; H, 7.76; N, 7.24.

EXAMPLE 136

Preparation of (S)-(−)-1-(4-indolyloxy)-3-(2-adamantyl-N-methylamino)-2-propanol succinate A mixture of (S)-(+)-(4-oxiranylmethoxy)-1H-indole (0.910 g, 4.8 mmol) and 2-adamantyl-N-methylamine (0.872 g, 5.3 mmol) in methanol (30 mL) was heated to reflux for 3 h. The methanol was evaporated and flash chromatography [silica gel, methylene chloride/methanol (93/7)] yielded 1.41 g oil. Crystallization as the succinate salt in ethyl acetate provided 1.05 g of crystals. Mp 75°–78° C. Mass spectrum, $m^+=354$. $[\alpha]^{23}_{589}=-13.2°$ (C=0.0089 g/mL, MeOH). Anal ($C_{26}H_{36}N_2O_6$) theory C, 66.08; H, 7.68; N, 5.93; found C, 66.19; H, 7.80; N, 5.67.

EXAMPLE 137

Preparation of (S)-(+)-1-(4-indolyloxy)-1-phenyl-3-(4-phenylpiperidin-1-yl)propane hydrochloride A mixture of (R)-3-chloro-1-phenyl-1-propanol (5.11 g, 30 mmol), 4-hydroxy-1H-indole (4.0 g, 30 mmol) and triphenyl phosphine (7.86 g, 30 mmol) were stirred together in tetrahydrofuran (90 mL) at ambient temperature. Diethyl azodicarboxylate (4.72 mL, 30 mmol) was added slowly. The resulting solution was stirred at ambient temperature for 18 h. Evaporation of the tetrahydrofuran followed by flash chromatography [silica gel, hexanes/ethyl acetate (3/1)] yielded 3.07 g oil. Mass spectrum, $m^+=285$.

The above (S)-1-(4-indolyloxy)-1-phenyl-3-chloropropane (0.572 g, 2 mmol), 4-phenylpiperidine (0.322 g, 2 mmol) and sodium carbonate (0.53 g, 5 mmol) were mixed together in 10 mL dimethylformamide. This mixture was heated at 100° C. for 18 h. Evaporation of dimethylformamide, dilution with methylene chloride, washing with water and drying (sodium sulfate) yielded 0.863 g oil. Flash chromatography [silica gel, methylene chloride/methanol (95/5)] yielded 0.277 g oil. Crystallization as the hydrochloride salt in diethyl ether provided 0.195 g of colorless solid. Mp 130° C. mass spectrum, $m^+=410$. $[\alpha]^{23}_{589}=76.9°$ (C=0.009 g/mL, MeOH). Anal ($C_{28}H_{31}ClN_2O$) theory C, 75.23; H, 6.99; N, 6.27; found C, 74.96; H, 6.88; N, 6.48.

EXAMPLE 138

Preparation of 1-(4-indolyloxy)-3-[4-(1H-indol-3-yl)-1,2,3,6-tetrahydropyridin-1-yl]propane A mixture of 1-chloro-3-hydroxypropane (4.2mL, 50 mmol), 4-hydroxy-1H-indole (6.66 g, 50 mmol) and triphenyl phosphine (13.1 g, 50 mmol) were stirred together in tetrahydrofuran (150 mL) at ambient temperature. Diethyl azodicarboxylate (7.9 ml, 50 mmol) was added slowly. The resulting solution was stirred at ambient temperature 18 h. Evaporation of the tetrahydrofuran followed by dilution with diethyl ether (200 mL), filtration, washing resulting filtrate with a 2N sodium hydroxide solution and brine, gave after drying (sodium sulfate) and evaporation 24.97 g oil. Flash chromatography [silica gel, hexanes/ethyl acetate (3/1)] yielded 5.93 g oil which crystallized. Mass spectrum, $m^+=209$.

The above 1-(4-indolyloxy)-3-chloropropane (0.629 g, 3 mmol), 3-(1,2,3,6-tetrahydropyridin-4-yl)-1H-indole (0.595 g, 3 mmol) and sodium carbonate (0.795 g, 7.5 mmol) were mixed together in 15 mL dimethylformamide. This mixture was heated at 100° C. for 18 h. Evaporation of dimethylformamide, dilution with water and crystallization of the resulting precipitate from ethanol provided 0.582 g of yellow crystals. Mp 192°–194° C. Mass spectrum, $m^+=371$. Anal ($C_{24}H_{25}N_3O$) theory C, 77.60; H, 6.78; N, 11.31; found C, 77.49; H, 6.53; N, 11.29.

EXAMPLE 139

Preparation of 1-(4-indolyloxy)-3-[4-(2-naphthyl)piperazin-1-yl]propane oxalate 1-(4-indolyloxy)-3-chloropropane (0.159 g, 0.75 mmol), 1-(2-naphthyl)piperazine (0.161 g, 0.75 mmol) and sodium carbonate (0.201 g, 1.89 mmol) were mixed together in 7 mL dimethylformamide and heated at 100° C. for 18 h. Evaporation of dimethylformamide, dilution with water and extractions with ethyl acetate provided 0.303 g. of oil. Crystallization as the oxalate salt from methanol provided 0.083 g of colorless crystals. Mp 209° C. Mass spectrum, $m^+=385$. Anal ($C_{27}H_{29}N_3O_5$) theory C, 68.20; H, 6.15; N, 8.84; found C, 68.47; H, 6.33; N, 8.60.

EXAMPLE 140

Preparation of 1-(4-indolyloxy)-3-[4-(1H-indol-3-yl)piperidin-1-yl]propane hydrochloride The product of Example 138 (0.370 g, 1 mmol) was hydrogenated (Pd/C, 40° C./18 h) in ethanol. Filtration, evaporation and flash chromatography [silica gel, methylene chloride/methanol/ammonium hydroxide (100/3/0.5)] yielded 0.177 g oil. Crystallization as the hydrochloride salt in diethyl ether provided 0.154 g of colorless solid. Mass spectrum, $m^+=373$. Anal ($C_{24}H_{28}ClN_3O$) theory C, 70.31; H, 6.88; N, 10.25; found C, 70.01; H, 6.91; N, 10.07.

EXAMPLE 141

Preparation of (2S)-(–)-1-(4-indolyloxy)-3-(4-phenyl-1,2,3,6-tetrahydropyridin-1-yl)-2-propanol ethanedioate The title compound was prepared according to Example 1 from (S)-(+)-4-(oxiranylmethoxy)-1H-indole and 4-phenyl-1,2,3,6-tetrahydropyridine. The resulting free base was dissolved in ethyl acetate, and precipitated with one equivalent of oxalic acid in ethyl acetate in 60% overall yield as a white foam. FDMS m/e=348 ($M^+$ of free base). $\alpha[D]_{589}$=–17.09 (c=0.49, methanol).

| analysis | calculated | found |
| --- | --- | --- |
| C | 65.74 | 65.78 |
| H | 5.98 | 6.04 |
| N | 6.39 | 6.07 |

EXAMPLE 142

Preparation of (2S)-(–)-1-(4-indolyloxy)-3-(4-(2-hydroxyimino)ethyl-4-phenylpiperidin-1-yl)-2-propanol ethanedioate The title compound was prepared by treating a solution of (2S)-(–)-1-(4-indolyloxy)-3-(4-acetyl-4-phenylpiperidin-1-yl)-2-propanol with excess hydroxylamine hydrochloride (5 equivalents) and 5 molar aq. sodium hydroxide solution in ethanol, with heating at reflux for one hour. The mixture was cooled, diluted with dichloromethane/methanol/sat. aq. ammonium hydroxide solution (100:10:1) and brine. The organic phase was separated, dried over sodium sulfate, concentrated and chromatographed over silica gel (dichloromethane-5% methanol/dichloromethane solvent gradient) to give the free base which was dissolved in ethyl acetate/methanol (1:1) and precipitated with one equivalent of oxalic acid in ethyl acetate to give the title compound in 90% yield as a white solid. mp. 125°–127° C. FDMS m/e=408 ($M^+$ of free base). $\alpha[D]_{589}$=–6.47 (c=0.49, methanol).

| analysis | calculated | found |
| --- | --- | --- |
| C | 62.76 | 62.88 |
| H | 6.28 | 6.59 |
| N | 8.45 | 8.60 |

EXAMPLE 143

Preparation of 1-(4-indolyloxy)-4-(4-(2-naphthyl)piperidin-1-yl)butane ethanedioate A solution of 1-chloro-4-(4-indolyloxy)butane (prepared from 4-hydroxy-1H-indole and 1-bromo-4-chlorobutane), 4-(2-naphthyl)piperidine and 3 equivalents of potassium carbonate in acetonitrile was heated at reflux for 12 h. The mixture was cooled and diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 48% overall yield as a tan solid. mp. 113°–115° C. FDMS m/e=398 ($M^+$ of free base).

| analysis | calculated | found |
| --- | --- | --- |
| C | 71.29 | 71.40 |
| H | 6.60 | 6.47 |
| N | 5.73 | 5.95 |

EXAMPLE 144

Preparation of 1-(4-indolyloxy)-5-(4-(2-naphthyl)piperidin-1-yl)pentane ethanedioate A solution of 1-chloro-5-(4-indolyloxy)pentane, 4-(2-naphthyl)piperidine and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 47% overall yield as a white solid. mp. 178°–180° C. FDMS m/e=412 ($M^+$ of free base).

| analysis | calculated | found |
| --- | --- | --- |
| C | 71.69 | 71.93 |
| H | 6.82 | 6.79 |
| N | 5.57 | 5.69 |

EXAMPLE 145

Preparation of 1-(4-indolyloxy)-2-(4-(2-naphthyl)piperidin-1-yl)ethane ethanedioate A solution of 1-chloro-2-(4-indolyloxy)ethane, 4-(2-naphthyl)piperidine and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 29% overall yield as a white solid. mp. 119°–120° C. FDMS m/e=370 ($M^+$ of free base).

| analysis | calculated | found |
| --- | --- | --- |
| C | 70.42 | 70.52 |
| H | 6.13 | 6.35 |
| N | 6.08 | 5.88 |

Preparation 20

Preparation of 5-chloro-2-(4-hydroxy-N-t-butoxycarbonylpiperidin-4-yl)benzo[b]thiophene A solution of 5-chlorobenzo[b]thiophene (0.600 g, 3.56 mmol) in freshly distilled tetrahydrofuran (20 ml) was treated with n-butyllithium (1.2M, 2.94 ml, 3.56 mmol) under nitrogen atmosphere at –78° C. The anion was allowed to stir for 60 minutes, and then was treated with a solution of N-t-butoxycarbonyl-4-piperidone (0.779 g, 3.91 mmol) in tetrahydrofuran (5.0 ml) and allowed to warm to 0° C. The reaction was quenched with sat. sodium bicarbonate, diluted with hexanes/diethyl ether (1:1), separated, the organic phase washed with brine and dried over sodium sulfate. Flash chromatography (silica gel, toluene/ethyl acetate 9:1) gave 1.09 g of a colorless foam which was contaminated with 20% unreacted piperidone. FDMS m/e= 367.

Preparation 21

Preparation of 5-chloro-2-(1,2,3,6-tetrahydropyridin-4-yl)benzo[b]thiophene

A solution of the product of Preparation 20 (0.998 g, 2.72 mmol) in methylene chloride (10 ml) was treated with 2.0 ml of trifluoroacetic acid and stirred at 23° C. for 3 hours. The reaction was concentrated to a foam under reduced pressure and the residue chromatographed (silica gel, chloroform/methanol 95:5) to give 0.444 g (65%) of a tan colored solid. A sample was dissolved in ethyl acetate, treated with 1.0 equivalent of oxalic acid and evaporated. mp=235°–237 C., FDMS m/e=250 ($M^+$ of free base)

| analysis | calculated | found |
|---|---|---|
| C | 53.02 | 53.06 |
| H | 4.15 | 4.27 |
| N | 4.12 | 4.10 |

Preparation 22

Preparation of 3-bromo-5-chlorobenzo[b]thiophene

A solution of bromine (0.31 g, 1.95 mmol) in 1.0 ml glacial acetic acid was added to a stirred solution of 5-chlorobenzo[b]thiophene (0.300 g, 1.77 mmol) in glacial acetic acid (1.0 ml) under nitrogen atmosphere. The reaction was heated to 50° C. for 4 hours, the volatiles removed under reduced pressure, the residue diluted in methylene chloride, washed with aq. sodium bicarbonate and with brine and dried over sodium sulfate. Evaporation gave 0.335 g (76%) of a tan solid. mp 85°–86 C., FDMS m/e=249 (M+2).

| analysis | calculated | found |
|---|---|---|
| C | 38.82 | 39.12 |
| H | 1.63 | 1.72 |

Preparation 23

Preparation of 5-chloro-3-(4-hydroxy-N-t-butoxycarbonylpiperidin-4-yl)benzo[b]thiophene A flame dried 50 ml flask was charged with n-butyllithium (1.55 ml, 1.86 mmol) in diethyl ether (5.0 ml) under nitrogen atmosphere. The internal temperature was lowered to −78° C. and treated with an ethereal solution (10 ml) of 3-bromo-5-chlorobenzo[b]thiophene (0.418 g, 1.68 mmol) After stirring at −78° C. for 60 minutes the rust-colored solution was treated with N-t-butoxycarbonyl-4-piperidone (0.401 g, 2.0 mmol) in diethyl ether (5.0 ml) and stirring continued for 2 hours at −78° C. followed by slow warming to −20° C. over 55 minutes. The reaction was quenched with saturated sodium bicarbonate, diluted with additional diethyl ether, separated, the organics washed with brine, and dried over sodium sulfate. Chromatography (silica, toluene/ethyl acetate 9:1) gave 0.36 g of a colorless foam which was contaminated with a small amount of unreacted piperidone. FDMS m/e=367 ($M^+$)

Preparation 24

Preparation of 5-chloro-3-(1,2,3,6-tetrahydropyridin-4-yl)benzo[b]thiophene

A solution of the product of Preparation 23 (0.320 g, 0.86 mmol) in methylene chloride (3.0 ml) was treated with 2.0 ml of trifluoroacetic acid and stirred at 23° C. for 4 hours. The reaction was concentrated to a foam under reduced pressure and the residue chromatographed (silica gel, chloroform/methanol 95:5) to give 0.140 g (64%) of a foam. The sample was dissolved in ether, treated with excess hydrochloric acid in ether and evaporated to an orange solid. mp=230°–235° C., FDMS m/e=250 ($M^+$ of free base)

| analysis | calculated | found |
|---|---|---|
| C | 54.55 | 54.81 |
| H | 4.58 | 4.77 |
| N | 4.89 | 5.14 |

Preparation 25

Preparation of 2-(3-chloro-1-thiophenyl)acetaldehyde diethyl acetal

A three-neck round bottom flask was charged with 3-chloro-thiophenol (20.0 g, 0.138 mol) and potassium carbonate (21 g, 0.15 mol) in acetone (220 ml) and treated with a dropwise addition of bromoacetaldehyde diethyl acetal. After stirring for 17 hours at 23° C., the slurry was filtered through a small plug of celite, the filtrate evaporated under reduced pressure and the residue diluted with diethyl ether and water. The organics were washed with brine, dried over sodium sulfate, and evaporated to a rust-colored oil weighing 35.1 g (97%). FDMS m/e=260 ($M^+$).

| analysis | calculated | found |
|---|---|---|
| C | 55.27 | 55.37 |
| H | 6.57 | 6.35 |

Preparation 26

Preparation of a 1:1 mixture of 4-chloro/6-chlorobenzo[b]thiophene

A one neck round bottom flask was charged with polyphosphoric acid (12.8 g) in refluxing chlorobenzene (100 ml) and treated by the dropwise addition of 2-(3-chloro-1-thiophenyl)acetaldehyde diethyl acetal (6.0 g, 0.023 mol) in chlorobenzene (20 ml). The slurry was stirred at reflux for 1 hour, cooled to 23° C. and the organics decanted from the mixture. After washing with brine, drying over sodium sulfate and evaporation, 2.75 g (71%) of a thin, rust-colored oil was isolated.

Preparation 27

Preparation of a 1:1 mixture of 4-chloro-2-(4-hydroxy-N-t-butoxycarbonylpiperidin-4-yl)benzo[b]thiophene and 6-chloro-2-(4-hydroxy-N-t-butoxycarbonylpiperidin-4-yl)benzo[b]thiophene A solution of a 1:1 mixture of 4-chlorobenzo[b]thiophene/6-chlorobenzo[b]thiophene (1.5 g, 8.92 mmol) in freshly distilled tetrahydrofuran (30.0 ml) was treated with n-butyllithium (1.3M, 7.55 ml, 9.82 mmol) under nitrogen atmosphere at −78° C. The anion was allowed to stir for 60 minutes then was treated with a solution of N-t-butoxycarbonyl-4-piperidone (1.95 g, 9.82 mmol) in tetrahydrofuran (10.0 ml) and allowed to warm to −0.5° C. The reaction was quenched with 0.5M sodium hydrogen sulfate, diluted with hexanes/diethyl ether (1:1), separated, the organic phase washed with brine and dried over sodium sulfate. Flash chromatography (silica gel, toluene/ethyl acetate 9:1) gave 0.64 g of a colorless solid which was identified by its $^1$H NMR spectrum as the 4-chloro regioisomer.

| analysis | calculated | found |
|---|---|---|
| C | 58.77 | 59.01 |
| H | 6.03 | 6.20 |
| N | 3.81 | 3.87 |

The second fraction isolated provided 1.04 g of a colorless foam which was identified as the 6-chloro regioisomer.

| analysis | calculated | found |
|---|---|---|
| C | 58.77 | 58.97 |
| H | 6.03 | 6.08 |
| N | 3.81 | 3.98 |

Preparation 28

Preparation of 4-chloro-2-(1,2,3,6-tetrahydropyridin-4-yl)benzo[b]thiophene

A solution of 4-chloro-2-(4-hydroxy-N-t-butoxycarbonylpiperidin-4-yl)benzo[b]thiophene (0.290 g, 0.79 mmol) in methylene chloride (4.0 ml) was treated with 1.5 ml of trifluoroacetic acid and stirred at 23° C. for 4 hours. The reaction was concentrated to a foam under reduced pressure and the residue chromatographed (silica gel, chloroform/methanol 95:5) to give 0.175 g (88%) of a tan powder. FDMS m/e=250 (M$^+$ of free base)

Preparation 29

Preparation of 6-chloro-2-(1,2,3,6-tetrahydropyridin-4-yl)benzo[b]thiophene

A solution of 6-chloro-2-(4-hydroxy-N-t-butoxycarbonylpiperidin-4-yl)benzo[b]thiophene (1.04 g, 2.83 mmol) in methylene chloride (30.0 ml) was treated with 4.36 ml of trifluoroacetic acid and stirred at 23° C. for 4 hours. The reaction was concentrated to a foam under reduced pressure and the residue chromatographed (silica gel, CHCl$_3$/MeOH 95:5) to give 0.640 g (90%) of a tan powder. FDMS m/e=250 (M$^+$ of free base)

Preparation 30

Preparation of 7-chloro-3-(1,2,3,6-tetrahydropyridin-4-yl)-1H-indole

Potassium hydroxide (6.89 g, 0.12 mol) was dissolved in methanol (30 mL). To the solution were added 7-chloroindole (4.65 g, 0.031 mol), 4-piperidone hydrochloride hydrate (9.48 g, 0.061 mol). The mixture was stirred at reflux temperature under nitrogen for about a day, and was cooled and diluted with 50 mL of water, added dropwise. The solid was collected, washed with water and vacuum dried. Yield 5.6 g (78%) as a yellow solid. mp 197°–201° C. FDMS m/e=232 (M+).

| analysis | calculated | found |
|---|---|---|
| C | 67.10 | 66.98 |
| H | 5.63 | 5.54 |
| N | 12.04 | 11.86 |

Preparation 31

Preparation of 7-chloro-3-(piperidin-4-yl)-1H-indole

7-Chloro-3-(1,2,3,6-tetrahydropyridin-4-yl)-1H-indole (2.0 g, 8.62 mmol) and 0.5 g of platinum oxide were added to 100 mL of ethanol and the mixture was shaken under about 50 psi hydrogen at about ambient temperature for about a day. The mixture was filtered and the filtrate concentrated to yield a solid comprising the desired product. Yield 1.64 g (81%) as a yellow solid. FDMS m/e=234 (M+).

EXAMPLE 146

Preparation of 3-[4-(5-chloro-3-indolyl)-1,2,3,6-tetrahydropyridin-1-yl]-1-(4-indolyloxy)propane hydrochloride The title compound was prepared in a fashion similar to that described in Example 99 using 1-chloro-3-(1H-indole-4-oxy)propane (0.444 g, 2.13 mmol) and the hydrochloride salt of 5-chloro-3-(1,2,3,6-tetrahydropyridin-1-yl)-1H-indole (0.500 g, 2.13 mmol) in the presence of 3.0 equivalents of potassium carbonate (0.881 g, 6.39 mmol) in dimethylformamide at 90° C. Yield 0.320 g (34%) of the HCl salt as a light brown solid. mp 167°–172° C. FDMS m/e=407 (M+ of free base).

| analysis | calculated | found |
|---|---|---|
| C | 64.86 | 64.95 |
| H | 6.12 | 6.17 |
| N | 9.45 | 9.32 |

EXAMPLE 147

Preparation of (2S)-(−)-3-[4-(6-trifluoromethyl-3-indolyl)-1,2,3,6-tetrahydropyridin-1-yl]-1-(4-indolyloxy)-2-propanol ethanedioate The title compound was prepared in a fashion similar to that described in Example 1 using (S)-(+)-4-(oxiranylmethoxy)-1H-indole (0.716 g, 3.78 mmol) and 6-trifluoromethyl-3-(1,2,3,6-tetrahydropyridin-1-yl)-1H-indole (1.0 g, 3.78 mmol) using ethanol as reaction solvent. Yield 0.340 g (20%) as a tan foam, which was treated with 1.0 equivalent of oxalic acid in diethyl ether and evaporated to a tan solid, mp 135°–139° C. FDMS m/e=455 (M+ of free base). α[D]$_{589}$=−13.1 (c=1.06, dimethylsulfoxide).

| analysis | calculated | found |
|---|---|---|
| C | 59.47 | 60.04 |
| H | 4.76 | 4.95 |
| N | 7.70 | 7.58 |

EXAMPLE 148

Preparation of 2-[4-(6-chloro-3-indolyl)-1,2,3,6-tetrahydropyridin-1-yl]-1-(4-indolyloxy)ethane ethanedioate The title compound was prepared in a fashion similar to that described in Example 99 using 1-chloro-2-(1H-indole-4-oxy)ethane (0.359 g, 1.85 mmol) and 6-chloro-3-(1,2,3,6-tetrahydropyridin-4-yl)-1H-indole (0.500 g, 2.13 mmol) in the presence of 2.0 equivalents of potassium carbonate (0.51 g, 3.7 mmol) in dimethylformamide at 90° C. Yield 0.101 g (14%) of a tan foam. The oxalate salt was prepared by treating the free base with 1.0 equivalent of oxalic acid in diethyl ether and evaporating. mp 120°–124° C. (browns) FDMS m/e=391 (M+ of free base).

| analysis | calculated | found |
|---|---|---|
| C | 62.31 | 62.09 |
| H | 5.02 | 5.10 |
| N | 8.72 | 8.66 |

EXAMPLE 149

Preparation of 4-[4-(6-chloro-3-indolyl)-1,2,3,6-tetrahydropyridin-1-yl]-1-(4-indolyloxy)butane The title compound was prepared in a fashion similar to that described in Example 99 using 1-chloro-4-(1H-indole-4-oxy)butane (0.479 g, 2.15 mmol) and 6-chloro-3-(1,2,3,6-tetrahydropyridin-4-yl)-1H-indole (0.500 g, 2.13 mmol) in the presence of 2.5 equivalents of potassium carbonate (0.742 g, 5.38 mmol) in dimethylformamide at 90° C. Yield 0.220 g (24%) of a tan foam. FDMS m/e=420 (M+ of free base).

| analysis | calculated | found |
|---|---|---|
| C | 71.54 | 71.11 |
| H | 6.19 | 6.29 |
| N | 10.00 | 10.54 |

EXAMPLE 150

Preparation of 3-[4-(7-chloro-3-indolyl)-1,2,3,6-tetrahydropyridin-1-yl)-1-(4-indolyloxy)propane The title compound was prepared in a fashion similar to that described in Example 99 using 1-chloro-3-(1H-indole-4-oxy)propane (0.446 g, 2.15 mmol) and 7-chloro-3-(1,2,3,6-tetrahydropyridin-4-yl)-1H-indole (0.500 g, 2.13 mmol) in the presence of 2.0 equivalents of potassium carbonate (0.593 g, 4.3 mmol) in dimethylformamide at 90° C. Yield 0.190 g (22%) of a tan foam. mp 166°–169° C. FDMS m/e=405 (M+ of free base).

| analysis | calculated | found |
|---|---|---|
| C | 71.01 | 70.71 |
| H | 5.96 | 6.01 |
| N | 10.35 | 10.28 |

EXAMPLE 151

Preparation of 3-[4-(6-chloro-3-indolyl)piperidin-1-yl]-1-(4-indolyloxy)propane

The title compound was prepared in a fashion similar to that described in Example 99 using 1-chloro-3-(1H-indole-4-oxy)propane (0.446 g, 2.15 mmol) and 6-chloro-3-(piperidin-4-yl)-1H-indole (0.500 g, 2.13 mmol) in the presence of 2.0 equivalents of potassium carbonate (0.593 g, 4.3 mmol) in dimethylformamide at 90° C. Yield 0.330 g (37%) of a colorless foam. FDMS m/e=407 (M+ of free base).

| analysis | calculated | found |
|---|---|---|
| C | 70.66 | 70.36 |
| H | 6.42 | 6.47 |
| N | 10.30 | 10.15 |

EXAMPLE 152

Preparation of (2S)-(+)-3-[4-(5-chloro-2-benzo[b]thiophenyl)-1,2,3,6-tetrahydropyridin-1-yl]-1-(4-indolyloxy)-2-propanol The title compound was prepared in a fashion similar to that described in Example 1 using (S)-(+)-4-(oxiranylmethoxy)-1H-indole (0.075 g, 0.042 mmol), and 5-chloro-2-(1,2,3,6-tetrahydropyridin-4-yl)benzo[b]thiophene (0.100 g, 0.042 mmol) using ethanol as reaction solvent. Yield 0.103 g (58%) of an orange oil. FDMS m/e=438 (M⁺ of free base). α[D]$_{589}$=+7.3 (c=0.95, dimethylsulfoxide)

| analysis | calculated | found |
|---|---|---|
| C | 65.67 | 65.43 |
| H | 5.28 | 5.30 |
| N | 6.38 | 6.23 |

EXAMPLE 153

Preparation of (2S)-(+)-3-[4-(5-chloro-3-indolyl)piperidin-1-yl]-1-(4-indolyloxy)-2-propanol The title compound was prepared in a fashion similar to that described in Example 1 using (S)-(+)-4-(oxiranylmethoxy)-1H-indole and 5-chloro-3-(piperidin-4-yl)-1H-indole using ethanol as the reaction solvent. Yield 0.380 g (42%) as a yellowish foam. mp 109°–114° C. (dec) FDMS m/e=423 (M⁺ of free base). α[D]$_{589}$=+6.5 (c=1.04, dimethylsulfoxide).

| analysis | calculated | found |
|---|---|---|
| C | 67.99 | 67.34 |
| H | 6.13 | 6.12 |
| N | 9.90 | 9.57 |

EXAMPLE 154

Preparation of (2S)-(+)-3-[4-(7-chloro-3-indolyl)piperidin-1-yl]-1-(4-indolyloxy)-2-propanol The title compound was prepared in a fashion similar to that described in Example 1 using (S)-(+)-4-(oxiranylmethoxy)-1H-indole (0.406 g, 2.13 mmol) and 7-chloro-3-(piperidin-4-yl)-1H-indole (0.500 g, 2.13 mmol) using ethanol as reaction solvent. Yield 0.325 g (35%) as a colorless powder. mp 186°–189° C. FDMS m/e=423 (M$^+$ of free base). $\alpha[D]_{589}$=+8.44 (c=1.09, dimethylsulfoxide).

| analysis | calculated | found |
|---|---|---|
| C | 68.00 | 68.23 |
| H | 6.18 | 6.28 |
| N | 9.91 | 10.20 |

EXAMPLE 155

Preparation of (2S)-(+)-3-[4-(5-chloro-3-benzo[b]thiophenyl)-1,2,3,6-tetrahydropyridin-1-yl]-1-(4-indolyloxy)-2-propanol The title compound was prepared in a fashion similar to that described in Example 1 using (S)-(+)-4-(oxiranylmethoxy)-1H-indole (0.053 g, 0.028 mmol) and the hydrochloride salt of 5-chloro-3-(1,2,3,6-tetrahydropyridin-4-yl)benzo[b]thiophene (0.08 1 g, 0.028 mmol) using ethanol as reaction solvent and 1.1 equivalents of potassium carbonate (0.043 g, 0.031 mmol). Yield 0.103 g (83%) of a tan foam. mp 93°–97° C. FDMS m/e=438 (M$^+$ of free base). $\alpha[D]_{589}$=+7.5 (c=1.06, dimethylsufoxide)

| analysis | calculated | found |
|---|---|---|
| C | 65.67 | 65.75 |
| H | 5.28 | 5.33 |
| N | 6.38 | 6.15 |

EXAMPLE 156

Preparation of (2S)-(–)-3-[4-(4-chloro-2-benzo[b]thiophenyl)-1,2,3,6-tetrahydropyridin-1-yl]-1-(4-indolyloxy)-2-propanol ethanedioate The title compound was prepared in a fashion similar to that described in Example 1 using (S)-(+)-4-(oxiranylmethoxy)-1H-indole (0.129 g, 0.068 mmol) and 4-chloro-2-(1,2,3,6-tetrahydropyridin-4-yl) benzo[b]thiophene (0.170 g, 0.068 mmol) using ethanol as reaction solvent. Yield 0.105 g (34%) of a tan powder. FDMS m/e=438 (M$^+$ of free base). A sample was dissolved in ethyl acetate and treated with 1.0 equivalent of oxalic acid and evaporated to an orange powder. mp 138°–142° C. (dec) $\alpha[D]_{589}$=–5.3 (c=1.13, dimethylsufoxide).

| analysis | calculated | found |
|---|---|---|
| C | 59.03 | 59.32 |
| H | 4.76 | 4.66 |
| N | 5.29 | 5.27 |

EXAMPLE 157

Preparation of (2R)-(–)-3-[4-(6-chloro-3-indolyl)-1,2,3,6-tetrahydropyridin-1-yl]-1-(5-quinolinyloxy-2-propanol The title compound was prepared in a fashion similar to that described in Example 1 using (R)-5-(oxiranylmethoxy)quinoline (0.495 g, 2.46 mmol) and 6-chloro-2-(1,2,3,6-tetrahydropyridin-4-yl)-1H-indole (0.519 g, 2.33 mmol) using ethanol as reaction solvent. Yield 0.840 g (87%) of a tan powder. FDMS m/e=433 (M$^+$ of free base). mp 221°–223° C. $\alpha[D]_{589}$=–9.9 (c=1.00, dimethylsulfoxide).

| analysis | calculated | found |
|---|---|---|
| C | 69.20 | 69.00 |
| H | 5.58 | 5.32 |
| N | 9.68 | 9.78 |

EXAMPLE 158

Preparation of (2S)-(+)-3-(4-(6-methyl-3-indolyl)-1,2,3,6-tetrahydropyridin-1-yl)-1-(4-indolyloxy)-2-propanol The title compound was prepared in a fashion similar to that described in Example 1 using (S)-(+)-4-(oxiranylmethoxy)-1H-indole (0.389 g, 2.05 mmol) and 6-methyl-3-(1,2,3,6-tetrahydropyridin-4-yl)-1H-indole (0.400 g, 1.87 mmol) using ethanol as reaction solvent. Yield 0.260 g (35%) as an orange foam. mp 99°–103° C. (dec). FDMS m/e= 401 (M+ of free base). $\alpha[D]_{589}$=+5.1 (c=0.98, dimethylsulfoxide).

| analysis | calculated | found |
|---|---|---|
| C | 74.79 | 74.50 |
| H | 6.78 | 6.76 |
| N | 10.47 | 10.22 |

EXAMPLE 159

Preparation of (2S)-(+)-3-[4-(7-methyl-3-indolyl)-1,2,3,6-tetrahydropyridin-1-yl)-1-(4-indolyloxy)-2-propanol The title compound was prepared in a fashion similar to that described in Example 1 using (S)-(+)-4-(oxiranylmethoxy)-1H-indole (0.389 g, 2.05 mmol) and 7-methyl-3-(1,2,3,6-tetrahydropyridin-4-yl)-1H-indole (0.400 g, 1.87 mmol) using ethanol as reaction solvent. Yield 0.292 g (39%) as an orange foam. mp 155°–158° C. FDMS m/e=401 (M+ of free base). $\alpha[D]_{589}$=+5.9 (c=1.05, dimethylsulfoxide).

| analysis | calculated | found |
|---|---|---|
| C | 74.79 | 74.54 |
| H | 6.78 | 6.85 |
| N | 10.47 | 10.33 |

EXAMPLE 160

Preparation of (2S)-(+)-3-[4-(6-chloro-2-benzo[b]thiophenyl)-1,2,3,6-tetrahydropyridin-1-yl]-1-(4-indolyloxy)-2-propanol The title compound was prepared in a fashion similar to that described in Example 1 using (S)-(+)-4-(oxiranylmethoxy)-1H-indole (0.166 g, 0.088 mmol) and 6-chloro-2-(1,2,3,6-tetrahydropyridin-4-yl)benzo[b]thiophene (0.200 g, 0.080 mmol) using ethanol as reaction solvent. Yield 0.122 g (35%) of a tan powder. FDMS m/e=438 ($M^+$ of free base).

| analysis | calculated | found |
|---|---|---|
| C | 65.67 | 65.43 |
| H | 5.28 | 5.29 |
| N | 6.38 | 6.67 |

EXAMPLE 161

Preparation of 1-(4-indolyloxy)-3-[4-(4-cyclopropylmethoxy-1H-indol-3-yl)piperidin-1-yl]propane ethanedioate monohydrate The title compound was prepared according to Example 99 from 1-chloro-3-(1H-indole-4-oxy)propane and 4-(4-cyclopropylmethoxy-1H-indol-3-yl)piperidine (which was prepared by condensing 4-cyclopropylmethoxyindole with 4-piperidone monohydrate hydrochloride in refluxing methanol with potassium hydroxide, followed by reduction of the unsaturation with palladium on carbon in methanol). The resulting free base was dissolved in ethyl acetate, and precipitated with one equivalent of oxalic acid in ethyl acetate in 57% overall yield as a white foam. FDMS m/e=443 ($M^+$ of free base).

| analysis | calculated | found |
|---|---|---|
| C | 65.32 | 65.38 |
| H | 6.76 | 6.73 |
| N | 7.62 | 7.72 |

EXAMPLE 162

Preparation of 1-(4-indolyloxy)-3-[4-(4-cyclopropylmethoxy-1H-indol-3-yl)-1,2,3,6-tetrahydropyridin-1-yl]propane ethanedioate The title compound was prepared in similar fashion from 1-chloro-3-(1H-indole-4-oxy)propane and 4-(4-cyclopropylmethoxy-1H-indol-3-yl)-1,2,3,6-tetrahydropyridine (which was prepared by condensing 4-cyclopropylmethoxyindole with 4-piperidone monohydrate hydrochloride in refluxing methanol with potassium hydroxide). The resulting free base was dissolved in ethyl acetate, and precipitated with one equivalent of oxalic acid in ethyl acetate in 20% overall yield as a white foam FDMS m/e=441 ($M^+$ of free base).

| analysis | calculated | found |
|---|---|---|
| C | 67.78 | 68.07 |
| H | 6.26 | 6.41 |
| N | 7.90 | 7.91 |

EXAMPLE 163

Preparation of 1-(4-indolyloxy)-3-[4-hydroxy-4-(1H-indol-5-yl)piperidin-1-yl]propane ethanedioate The title compound was prepared in similar fashion from 1-chloro-3-(1H-indole-4-oxy)propane and 4-hydroxy-4-(1H-indol-5-yl)piperidine (which was prepared by treatment of the potassium salt of 5-bromoindole with tert-butyllithium in tetrahydrofuran at −78° C., followed by quenching with N-benzyl-4-piperidone in tetrahydrofuran, and hydrogenolysis of the resulting adduct with palladium on carbon in ethanol, to give the desired piperidine in 20% yield). The resulting free base was dissolved in ethyl acetate, and precipitated with one equivalent of oxalic acid in ethyl acetate in 68% overall yield as a foam. FDMS m/e=390 ($M^+$ of free base).

| analysis | calculated | found |
|---|---|---|
| C | 65.12 | 65.47 |
| H | 6.10 | 5.97 |
| N | 8.76 | 9.07 |

EXAMPLE 164

Preparation of 1-(4-indolyloxy)-3-[4-hydroxy-4-(2-naphthyl)piperidin-1-yl]propane ethanedioate The title compound was prepared in similar fashion from 1-chloro-3-(1H-indole-4-oxy)propane and 4-(2-naphthyl)piperdine. The resulting free base was dissolved in ethyl acetate, and precipitated with one equivalent of oxalic acid in ethyl acetate in 24% overall yield as a foam. FDMS m/e=400 ($M^+$ of free base).

| analysis | calculated | found |
|---|---|---|
| C | 68.56 | 68.84 |
| H | 6.16 | 6.09 |
| N | 5.71 | 5.55 |

EXAMPLE 165

Preparation of 1-(4-indolyloxy)-3-[4-(6-methoxynaphth-2-yl)piperidin-1-yl]propane ethanedioate The title compound was prepared in similar fashion from 1-chloro-3-(1H-indole-4-oxy)propane and 4-[2-(6-methoxynaphthyl)]piperidine. The resulting free base was dissolved in ethyl acetate, and precipitated with one equivalent of oxalic acid in ethyl acetate in 60% overall yield as a foam. FDMS m/e=414 ($M^+$ of free base).

| analysis | calculated | found |
|---|---|---|
| C | 69.03 | 68.79 |
| H | 6.39 | 6.09 |
| N | 5.55 | 5.30 |

EXAMPLE 166

Preparation of (2S)-(−)-1-(4-indolyloxy)-3-[4-(6-methoxynaphth-2-yl) piperidin-1-yl]-2-propanol ethanedioate The title compound was prepared according to Example 1 from (S)-(+)-4-(oxiranylmethoxy)-1H-indole and 4-[2-(6-methoxynaphthyl)]piperidine. The resulting free base was dissolved in ethyl acetate, and precipitated with one equivalent of oxalic acid in ethyl acetate in 66% overall yield as a foam. FDMS m/e=430 ($M^+$ of free base). $\alpha[D]_{589}$=−5.64 (c=0.53, methanol).

| analysis | calculated | found |
|---|---|---|
| C | 66.91 | 66.64 |
| H | 6.20 | 6.24 |
| N | 5.38 | 5.14 |

EXAMPLE 167

Preparation of (2S)-(−)-1-(4-indolyloxy)-3-(5-methoxyspiro[benzodihydrothiophene-1(3H),4'-piperidin]-1'-yl)-2-propanol ethanedioate The title compound was prepared according to Example 121 from (S)-(+)-4-(oxiranylmethoxy)-1H-indole and 5-methoxyspiro[benzodihydrothiophene-1(3H),4'-piperidine]. The resulting free base was dissolved in ethyl acetate, and precipitated with one equivalent of oxalic acid in ethyl acetate in 83% overall yield. mp. 123°–125° C. FDMS m/e=424 ($M^+$ of free base). $\alpha[D]_{589}$=−14.71 (c=0.48, methanol).

| analysis | calculated | found |
|---|---|---|
| C | 60.69 | 60.63 |
| H | 5.88 | 6.17 |
| N | 5.44 | 5.22 |

EXAMPLE 168

Preparation of 1-(4-indolyloxy)-3-(4-benzyloxyspiro[benzodihydrofuran-1(3H),4'-piperidin]-3-one-1'-yl)propane ethanedioate A solution of 1-chloro-3-(1H-indole-4-oxy)propane, 4-benzyloxyspiro[benzodihydrofuran-1(3H),4'-piperidin]-3-one and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 33% overall yield as a foam. FDMS m/e=482 ($M^+$ of free base).

| analysis | calculated | found |
|---|---|---|
| C | 67.12 | 66.82 |
| H | 5.63 | 5.49 |
| N | 4.89 | 5.05 |

EXAMPLE 169

Preparation of 1-(4-indolyloxy)-3-(5-methoxyspiro[benzodihydrothiophene-1(3H),4,-piperidin]-1'-yl)propane ethanedioate The title compound was prepared in similar fashion from 1-chloro-3-(1H-indole-4-oxy)propane and 5-methoxyspiro[benzodihydrothiophene-1(3H),4,-piperidine]. The resulting free base was dissolved in ethyl acetate, and precipitated with one equivalent of oxalic acid in ethyl acetate in 57% overall yield. mp. 125°–126° C. FDMS m/e=408 ($M^+$ of free base).

| analysis | calculated | found |
|---|---|---|
| C | 62.63 | 62.46 |
| H | 6.06 | 6.26 |
| N | 5.62 | 5.77 |

EXAMPLE 170

Preparation of (2S)-(−)-1-(4-indolyloxy)-3-(4-phenylspiro[benzodihydrofuran-1(3H),4'-piperidin]-3-one-1'-yl)-2-propanol ethanedioate The title compound was prepared in similar fashion from (S)-(+)-4-(oxiranylmethoxy)-1H-indole and 4-phenylspiro[benzodihydrofuran-1(3H),4'-piperidin]-3-one. The resulting free base was dissolved in ethyl acetate, and precipitated with one equivalent of oxalic acid in ethyl acetate in 73% overall yield. mp 215°–217° C. (decomp). FDMS m/e=468 ($M^+$ of free base). $\alpha[D]_{589}$=−65.93 (c=0.55, methanol).

| analysis | calculated | found |
|---|---|---|
| C | 66.66 | 66.46 |
| H | 5.41 | 5.44 |
| N | 5.02 | 4.98 |

EXAMPLE 171

Preparation of 1-(4-indolyloxy)-3-(4-phenylspiro[benzodihydrofuran-1(3H),4'-piperidin]-3-one -1'-yl)propane ethanedioate The title compound was prepared in similar fashion from 1-chloro-3-(1H-indole-4-oxy)propane and 4-phenylspiro[benzodihydrofuran-1(3H),4'-piperidin]-3-one. The resulting free base was dissolved in ethyl acetate, and precipitated with one equivalent of oxalic acid in ethyl acetate in 42% overall yield. mp 226°–228° C. (decomp). FDMS m/e=452 ($M^+$ of free base).

| analysis | calculated | found |
|---|---|---|
| C | 68.62 | 68.39 |
| H | 5.57 | 5.71 |
| N | 5.16 | 5.13 |

EXAMPLE 172

Preparation of 1-(4-indolyloxy)-3-(4-hydroxyspiro[benzodihydrofuran-1(3H),4'-piperidin]-3-one-1'-yl)propane ethanedioate A solution of 1-(4-indolyloxy)-3-(4-benzyloxyspiro[benzodihydrofuran-1(3H),4'-piperidin]-3-one-1'-yl)propane in methanol was treated with a catalytic amount of 5% palladium on carbon, and hydrogen (one atmosphere) overnight. The mixture was filtered through a pad of Celite and concentrated, to give the free base, which was dissolved in ethyl acetate and precipitated with one equivalent of oxalic acid to give the title compound in 85% overall yield as a foam. FDMS m/e=392 ($M^+$ of free base).

| analysis | calculated | found |
|---|---|---|
| C | 62.23 | 62.41 |
| H | 5.43 | 5.43 |
| N | 5.81 | 5.55 |

EXAMPLE 173

Preparation of 1-(4-indolyloxy)-3-(4-phenylspiro[benzodihydrofuran-1(3H),4'-piperidin]-1'-yl)propane ethanedioate A solution of 1-chloro-3-(1H-indole-4-oxy)propane, 4-phenylspiro[benzodihydrofuran-1(3H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 38% overall yield as a foam. FDMS m/e=438 ($M^+$ of free base).

| analysis | calculated | found |
|---|---|---|
| C | 70.44 | 70.29 |
| H | 6.10 | 6.10 |
| N | 5.30 | 5.19 |

EXAMPLE 174

Preparation of (2S)-(−)-1-(4-indolyloxy)-3-(6,7-ethylenedioxyspiro[benzodihydrofuran-1(3H),4'-piperidin]-3-one-1'-yl)-2-propanol ethanedioate The title compound was prepared in similar fashion from (S)-(+)-4-(oxiranylmethoxy)-1H-indole and 6,7-ethylenedioxyspiro[benzodihydrofuran-1(3H),4'-piperidin]-3-one. The resulting free base was dissolved in ethyl acetate, and precipitated with one equivalent of oxalic acid in ethyl acetate in 78% overall yield. FDMS m/e=450 ($M^+$ of free base). $\alpha[D]_{589}$=−9.26 (c=0.32, methanol).

| analysis | calculated | found |
|---|---|---|
| C | 60.00 | 59.71 |
| H | 5.22 | 5.43 |
| N | 5.18 | 5.08 |

EXAMPLE 175

Preparation of 1-(4-indolyloxy)-3-(6,7-ethylenedioxyspiro[benzodihydrofuran-1(3H),4'-piperidin]-3-one-1'-yl)propane ethanedioate A solution of 1-chloro-3-(1H-indole-4-oxy)propane, 6,7-ethylenedioxyspiro[benzodihydrofuran-1(3H),4'-piperidin]-3-one and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 45% overall yield as a foam. FDMS m/e=434 ($M^+$ of free base).

| analysis | calculated | found |
|---|---|---|
| C | 61.83 | 62.02 |
| H | 5.38 | 5.60 |
| N | 5.34 | 5.37 |

EXAMPLE 176

Preparation of 1-(4-indolyloxy)-3-(1,5-dihydrospiro[4H-2-benzopyran-4,4'-piperidin]-1'-yl)propane ethanedioate The title compound was prepared in similar fashion from 1-chloro-3-(1H-indole-4-oxy)propane and 1,5-dihydrospiro[4H-2-benzopyran-4,4'-piperidine]. The resulting free base was dissolved in ethyl acetate, and precipitated with one equivalent of oxalic acid in ethyl acetate in 69% overall yield as a foam. FDMS m/e=376 ($M^+$ of free base).

| analysis | calculated | found |
|---|---|---|
| C | 66.94 | 66.71 |
| H | 6.48 | 6.60 |
| N | 6.00 | 5.92 |

EXAMPLE 177

Preparation of 1-(4-indolyloxy)-3-(6,7-ethylenedioxyspiro[benzodihydrofuran-1(3H),4'-piperidin]-1'-yl)propane ethanedioate A solution of 1-chloro-3-(1H-indole-4-oxy)propane, 6,7-ethylenedioxyspiro[benzodihydrofuran-1(3H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 39% overall yield as a foam. FDMS m/e=420 ($M^+$ of free base).

| analysis | calculated | found |
|---|---|---|
| C | 63.52 | 63.57 |
| H | 5.92 | 5.88 |
| N | 5.49 | 5.22 |

EXAMPLE 178

Preparation of (2S)-(−)-1-(4-indolyloxy)-3-(6,7-ethylenedioxyspiro[benzodihydrofuran-1(3H),4'-piperidin]-1'-yl)-2-propanol ethanedioate The title compound was prepared in similar fashion from (S)-(+)-4-(oxiranylmethoxy)-1H-indole and 6,7-ethylenedioxyspiro[benzodihydrofuran-1(3H),4'-piperidine]. The resulting free base was dissolved in ethyl acetate, and precipitated with one equivalent of oxalic acid in ethyl acetate in 54% overall yield. FDMS m/e=436 (M$^+$ of free base). $\alpha[D]_{589}$=−12.70 (c=0.55, methanol).

| analysis | calculated | found |
|---|---|---|
| C | 61.59 | 61.89 |
| H | 5.74 | 5.95 |
| N | 5.32 | 5.52 |

EXAMPLE 179

Preparation of 1-(4-indolyloxy)-3-(6-benzyloxyspiro[benzodihydrofuran-1(3H),4'-piperidin]-3-one-1'-yl)propane ethanedioate A solution of 1-chloro-3-(1H-indole-4-oxy)propane, 6-benzyloxyspiro[benzodihydrofuran-1(3H),4'-piperidin]-3-one and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 62% overall yield as a foam. FDMS m/e=482 (M$^+$ of free base).

| analysis | calculated | found |
|---|---|---|
| C | 67.12 | 66.93 |
| H | 5.63 | 5.66 |
| N | 4.89 | 4.72 |

EXAMPLE 180

Preparation of (2S)-(−)-1-(4-indolyloxy)-3-(4-ethoxyspiro[benzodihydrofuran-1(3H),4'-piperidin]-1'-yl)-2-propanol ethanedioate The title compound was prepared in similar fashion from (S)-(+)-4-(oxiranylmethoxy)-1H-indole and 4-ethoxyspiro[benzodihyrofuran-1(3H),4'-piperidine]. The resulting free base was dissolved in ethyl acetate, and precipitated with one equivalent of oxalic acid in ethyl acetate in 70% overall yield as a foam. FDMS m/e=422 (M$^+$ of free base). $\alpha[D]_{589}$=−5.25 (c=0.57, methanol).

| analysis | calculated | found |
|---|---|---|
| C | 63.27 | 63.56 |
| H | 6.29 | 6.37 |
| N | 5.47 | 5.26 |

EXAMPLE 181

Preparation of 1-(4-indolyloxy)-3-(4-ethoxyspiro[benzodihydrofuran-1(3H),4'-piperidin]-1'-yl)propane ethanedioate A solution of 1-chloro-3-(1H-indole-4-oxy)propane, 4-ethoxyspiro[benzodihydrofuran-1(3H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 38% overall yield as a foam. FDMS m/e=406 (M$^+$ of free base).

| analysis | calculated | found |
|---|---|---|
| C | 65.31 | 65.12 |
| H | 6.50 | 6.40 |
| N | 5.64 | 5.45 |

EXAMPLE 182

Preparation of 1-(4-indolyloxy)-3-(4-benzyloxyspiro[benzodihydrofuran-1(3H),4'-piperidin]-1'-yl)propane ethanedioate A solution of 1-chloro-3-(1H-indole-4-oxy)propane, 4-benzyloxyspiro[benzodihydrofuran-1(3H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 70% overall yield as a foam. FDMS m/e=468 (M$^+$ of free base).

| analysis | calculated | found |
|---|---|---|
| C | 68.80 | 68.55 |
| H | 6.13 | 6.15 |
| N | 5.01 | 4.89 |

EXAMPLE 183

Preparation of (2S)-(−)-1-(4-indolyloxy)-3-(6-ethoxyspiro[benzodihydrofuran-1(3H),4'-piperidin]-3-one-1'-yl)-2-propanol ethanedioate The title compound was prepared in similar fashion from (S)-(+)-4-(oxiranylmethoxy)-1H-indole and 6-ethoxyspiro[benzodihydrofuran-1(3H),4'-piperidin]-3-one. The resulting free base was dissolved in ethyl acetate, and precipitated with one equivalent of oxalic acid in ethyl acetate in 91% overall yield as a foam. FDMS m/e=436 (M⁺ of free base). α[D]₅₈₉=−5.50 (c=0.55, methanol).

| analysis | calculated | found |
|---|---|---|
| C | 68.79 | 68.58 |
| H | 6.47 | 6.55 |
| N | 6.42 | 6.28 |

EXAMPLE 184

Preparation of 1-(4-indolyloxy)-3-(6-ethoxyspiro[benzodihydrofuran-1(3H),4'-piperidin]-3-one-1'-yl)propane ethanedioate A solution of 1-chloro-3-(1H-indole-4-oxy)propane, 6-ethoxyspiro[benzodihydrofuran-1(3H),4'-piperidin]-3-one and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 36% overall yield as a foam. FDMS m/e=420 (M⁺ of free base).

| analysis | calculated | found |
|---|---|---|
| C | 63.52 | 63.59 |
| H | 5.92 | 5.82 |
| N | 5.49 | 5.11 |

EXAMPLE 185

Preparation of (2S)-(−)-1-(4-indolyloxy)-3-(6-ethoxyspiro[benzodihydrofuran-1(3H),4'-piperidin]-1'-yl)-2-propanol ethanedioate The title compound was prepared in similar fashion from (S)-(+)-4-(oxiranylmethoxy)-1H-indole and 6-ethoxyspiro[benzodihydrofuran-1(3H),4'-piperidine]. The resulting free base was dissolved in ethyl acetate, and precipitated with one equivalent of oxalic acid in ethyl acetate in 59% overall yield as a foam. FDMS m/e=422 (M⁺ of free base). α[D]₅₈₉=−3.58 (c=0.56, methanol).

| analysis | calculated | found |
|---|---|---|
| C | 63.27 | 62.99 |
| H | 6.29 | 6.29 |
| N | 5.47 | 5.16 |

EXAMPLE 186

Preparation of 1-(4-indolyloxy)-3-(6-ethoxyspiro[benzodihydrofuran-1(3H),4'-piperidin]-1'-yl)propane ethanedioate A solution of 1-chloro-3-(1H-indole-4-oxy)propane, 6-ethoxyspiro[benzodihydrofuran-1(3H),4'-piperidine] and 3 equivalents of potassium carbonate in acetonitrile was heated at reflux for 12 h. The mixture was cooled, diluted with ethyl acetate, and the organic layer was separated and washed with brine. The crude residue was purified by silica gel chromatography (dichloromethane/5% methanol in dichloromethane gradient eluent). The resulting free base was dissolved in ethyl acetate and precipitated with one equivalent of oxalic acid in ethyl acetate, to give the title compound in 52% overall yield as a foam. FDMS m/e=406 (M⁺ of free base).

| analysis | calculated | found |
|---|---|---|
| C | 65.31 | 65.06 |
| H | 6.50 | 6.48 |
| N | 5.64 | 5.28 |

EXAMPLE 187

Preparation of 1-(4-indolyloxy)-3-[4-(3,4-ethylenedioxyphenyl)piperidin-1-yl]propane ethanedioate The title compound was prepared in similar fashion from 1-chloro-3-(1H-indole-4-oxy)propane and 4-(3,4-ethylenedioxyphenyl)piperidine. The resulting free base was dissolved in ethyl acetate, and precipitated with one equivalent of oxalic acid in ethyl acetate in 59% overall yield as a foam. FDMS m/e=392 (M⁺ of free base).

| analysis | calculated | found |
|---|---|---|
| C | 64.72 | 65.08 |
| H | 6.27 | 6.57 |
| N | 5.81 | 5.68 |

EXAMPLE 188

Preparation of 1-(4-indolyloxy)-3-[4-(2-naphthyl)piperidin-1-yl]propane ethanedioate The title compound was prepared in similar fashion from 1-chloro-3-(1H-indole-4-oxy)propane and 4-(2-naphthyl)piperidine. The resulting free base was dissolved in ethyl acetate, and precipitated with one equivalent of oxalic acid in ethyl acetate in 57% overall yield as a white solid. mp. 145°–146° C. FDMS m/e=384 (M⁺ of free base).

| analysis | calculated | found |
|---|---|---|
| C | 70.87 | 71.14 |
| H | 6.37 | 6.30 |
| N | 5.90 | 5.62 |

EXAMPLE 189

Preparation of (2S)-(−)-1-(4-indolyloxy)-3-(5-methylspiro[benzodihydrofuran-1(3H),4'-piperidin]-1'-yl)-2-propanol ethanedioate The title compound was prepared according to Example 1 from (S)-(+)-4-(oxiranylmethoxy)-1H-indole and 5-methylspiro[benzodihydrofuran-1(3H),4'-piperidine]. The resulting free base was dissolved in ethyl acetate, and precipitated with one equivalent of oxalic acid in ethyl acetate in 72% overall yield as a foam. FDMS m/e=392 (M⁺ of free base). α[D]₅₈₉=−16.89 (c=0.53, methanol).

| analysis | calculated | found |
|---|---|---|
| C | 64.72 | 65.00 |
| H | 6.27 | 6.30 |
| N | 5.81 | 5.80 |

EXAMPLE 190

Preparation of (2S)-(–)-1-(4-indolyloxy)-3-(4-benzyloxyspiro[benzodihydrofuran-1(3H),4'-piperidin]-1'-yl)-2-propanol ethanedioate The title compound was prepared in similar fashion from (S)-(+)-4-(oxiranylmethoxy)-1H-indole and 4-benzyloxyspiro[benzodihydrofuran-1(3H),4'-piperidine]. The resulting free base was dissolved in ethyl acetate, and precipitated with one equivalent of oxalic acid in ethyl acetate in 90% overall yield as a foam. FDMS m/e=484 ($M^+$ of free base). $\alpha[D]_{589}$=–15.32 (c=0.52, methanol).

| analysis | calculated | found |
|---|---|---|
| C | 66.89 | 67.13 |
| H | 5.96 | 6.23 |
| N | 4.88 | 4.96 |

EXAMPLE 191

Preparation of 1-(4-indolyloxy)-3-(benzo[c]spiro[benzodihydrofuran-1(3H),4'-piperidin]-1'-yl)propane ethanedioate The title compound was prepared according to Example 121 from 1-chloro-3-(1H-indole-4-oxy)propane and benzo[c]spiro[benzodihydrofuran-1(3H),4'-piperidine]. The resulting free base was dissolved in ethyl acetate, and precipitated with one equivalent of oxalic acid in ethyl acetate in 50% overall yield as a white solid. mp. 159°–160° C. FDMS m/e=412 ($M^+$ of free base).

| analysis | calculated | found |
|---|---|---|
| C | 69.31 | 69.55 |
| H | 6.02 | 6.28 |
| N | 5.57 | 5.64 |

PREPARATION 32

Preparation of 5-methoxy-3-(1,2,3,6-tetrahydropyridin-4-yl)-1H-indole

The title compound was prepared in a fashion similar to that described in Preparation 30 from 5-methoxyindole (5.0 g, 34 mmol) and 4-piperidone hydrochloride hydrate (10.0 g, 65 mmol). The product was isolated as a yellow solid. Yield 6.1 g (79%). mp 191°–195° C. FDMS m/e=228 ($M^+$ of free base).

| analysis | calculated | found |
|---|---|---|
| C | 73.66 | 73.38 |
| H | 7.06 | 7.08 |
| N | 12.27 | 12.36 |

Preparation 33

Preparation of 6-methoxy-3-(1,2,3,6-tetrahydropyridin-4-yl)-1H-indole

The title compound was prepared in a fashion similar to that described in Preparation 30 from 6-methoxyindole (2.0 g, 14 mmol) and 4-piperidone hydrochloride hydrate (4.2 g, 27 mmol). The product was isolated as a yellow solid. Yield 2.8 g (90%). mp 190°–193° C. FDMS m/e=228 ($M^+$ of free base).

| analysis | calculated | found |
|---|---|---|
| C | 73.66 | 73.44 |
| H | 7.06 | 7.16 |
| N | 12.27 | 12.37 |

Preparation 34

Preparation of 6-chloro-5-methoxy-3-(1,2,3,6-tetrahydropyridin-4-yl)-1H-indole

The title compound was prepared in a fashion similar to that described in Preparation 30 from 6-chloro-5-methoxyindole (2.0 g, 11 mmol) and 4-piperidone hydrochloride hydrate (3.4 g, 22 mmol). The product was isolated as a yellow solid. Yield 2.4 g (83%). mp 222°–224° C. FDMS m/e=264 ($M^+$ of free base).

| analysis | calculated | found |
|---|---|---|
| C | 64.00 | 64.12 |
| H | 5.75 | 5.86 |
| N | 10.66 | 10.57 |

Preparation 35

Preparation of 6-trifluoromethyl-3-(piperidin-4-yl)-1H-indole monohydrate

The title compound was prepared in a fashion similar to that described in Preparation 31 from 6-trifluoromethyl-3-(1,2,3,6-tetrahydropyridin-4-yl)-1H-indole (2.1 g, 7.9 mmol). The product was isolated as a yellow solid. Yield 1.2 g (57%). mp 210°–214° C. FDMS m/e=268 ($M^+$ of free base).

| analysis | calculated | found |
|---|---|---|
| C | 58.73 | 58.70 |
| H | 5.98 | 5.44 |
| N | 9.78 | 9.96 |

Preparation 36

Preparation of 6,7-dichloro-3-(piperidin-4-yl)-1H-indole

The title compound was prepared in a fashion similar to that described in Preparation 31 from 6,7-dichloro-3-(1,2,3,6-tetrahydropyridin-4-yl)-1H-indole (4.5 g, 16.8 mmol). The product was isolated as a white solid. Yield 4.1 g (91%). mp 254°–257° C. FDMS m/e=270 ($M^+$ of free base).

| analysis | calculated | found |
|---|---|---|
| C | 58.01 | 58.25 |
| H | 5.24 | 5.42 |
| N | 10.41 | 10.64 |

Preparation 37

Preparation of 6,7-dichloro-3-(1,2,3,6-tetrahydropyridin-4-yl)-1H-indole

The title compound was prepared in a fashion similar to that described in Preparation 30 from 6,7-dichloroindole (1.4 g, 7.5 mmol) and 4-piperidone hydrochloride hydrate (2.3 g, 15 mmol). The product was isolated as a white solid. Yield 1.8 g (89%). mp 252°–254° C. FDMS m/e=268 ($M^+$ of free base).

| analysis | calculated | found |
|---|---|---|
| C | 58.45 | 58.71 |
| H | 4.53 | 4.64 |
| N | 10.49 | 10.33 |

Preparation 38

Preparation of 7-chloro-3-(1,2,3,6-tetrahydropyridin-4-yl)-1H-indole

The title compound was prepared in a fashion similar to that described in Preparation 30 from 7-chloroindole (0.70 g, 4.6 mmol) and 4-piperidone hydrochloride hydrate (1.4 g, 9.2 mmol). The product was isolated as a yellow solid. Yield 0.80 g (75%). mp 205°–208° C. FDMS m/e=234 ($M^+$ of free base).

| analysis | calculated | found |
|---|---|---|
| C | 67.10 | 67.06 |
| H | 5.63 | 5.85 |
| N | 12.04 | 12.01 |

Preparation 39

Preparation of 6-nitro-3-(1,2,3,6-tetrahydropyridin-4-yl)-1H-indole

The title compound was prepared in a fashion similar to that described in Preparation 30 from 6-nitroindole (6.0 g, 37 mmol) and 4-piperidone hydrochloride hydrate (11.4 g, 74 mmol). The product was isolated as an orange solid. Yield 8.8 g (97%). mp 247°–250° C. (dec.) FDMS m/e=243 ($M^+$ of free base).

| analysis | calculated | found |
|---|---|---|
| C | 64.19 | 64.37 |
| H | 5.39 | 5.40 |
| N | 17.27 | 17.50 |

Preparation 40

Preparation of 5-chloro-3-(1,2,3,6-tetrahydropyridin-4-yl)-1H-indole

The title compound was prepared in a fashion similar to that described in Preparation 30 from 5-chloroindole (3.0 g, 20 mmol) and 4-piperidone hydrochloride hydrate (6.0 g, 40 mmol). The product was isolated as a yellow solid. Yield 1.45 g (31%). mp 185°–188° C. FDMS m/e=234 ($M^+$ of free base).

| analysis | calculated | found |
|---|---|---|
| C | 67.10 | 67.38 |
| H | 5.63 | 5.58 |
| N | 12.04 | 12.25 |

Preparation 41

Preparation of 6-trifluoromethyl-3-(1,2,3,6-tetrahydropyridin-4-yl)-1H-indole

The title compound was prepared in a fashion similar to that described in Preparation 30 from 6-trifluoromethylindole (4.0 g, 22 mmol) and 4-piperidone hydrochloride hydrate (6.6 g, 43 mmol). The product was isolated as a white solid. Yield 3.7 g (64%). mp °C. FDMS m/e=266 ($M^+$ of free base).

| analysis | calculated | found |
|---|---|---|
| C | 63.15 | 62.90 |
| H | 4.92 | 4.96 |
| N | 10.52 | 10.57 |

Preparation 42

Preparation of 6-fluoro-3-(piperidin-4-yl)-1H-indole

The title compound was prepared in a fashion similar to that described in Preparation 31 from 6-fluoro-3-(1,2,3,6-tetrahydropyridin-4-yl)-1H-indole (19.2 g, 89 mmol). The product was isolated as a white solid. Yield 18.5 g (96%). mp 234°–236° C. FDMS m/e=218 ($M^+$ of free base).

| analysis | calculated | found |
|---|---|---|
| C | 71.53 | 71.77 |
| H | 6.93 | 7.11 |
| N | 12.83 | 13.00 |

Preparation 43

Preparation of 6-chloro-3-(1,2,3,6-tetrahydropyridin-4-yl)-1H-indole

The title compound was prepared in a fashion similar to that described in Preparation 30 from 6-chloroindole (4.0 g, 26 mmol) and 4-piperidone hydrochloride hydrate (8.0 g, 52 mmol). The product was isolated as a yellow solid. Yield 3.7 g (61%). mp 181°–185° C. FDMS m/e=234 ($M^+$ of free base).

| analysis | calculated | found |
|---|---|---|
| C | 67.10 | 67.13 |
| H | 5.63 | 5.70 |
| N | 12.04 | 12.18 |

Preparation 44

Preparation of 6-chloro-3-(piperidin-4-yl)-1H-indole hydrochloride

The title compound was prepared in a fashion similar to that described in Preparation 31 from 6-chloro-3-(1,2,3,6-tetrahydropyridin-4-yl)-1H-indole (1.0 g, 4.3 mmol). The product was isolated as a white solid. Yield 0.65 g (56%). mp 290°–294° C. (dec.) FDMS m/e=234 ($M^+$ of free base).

| analysis | calculated | found |
|---|---|---|
| C | 57.58 | 57.30 |
| H | 5.95 | 6.15 |
| N | 10.33 | 10.57 |

Preparation 45

Preparation of 6-nitro-3-(piperidin-4-yl)-1H-indole trifluoroacetate 6-nitro-3-(1,2,3,6-tetrahydropyridin-4-yl)-1H-indole (2.4 g, 9.9 mmol) was stirred in trifluoroacetic acid (10 mL) at room temperature under an atmosphere of nitrogen. Triethylsilane (1.65 mL, 10.4 mmol) was slowly added. After an initial exotherm, the mixture was stirred at room temperature for 12 hours. The mixture was concentrated under reduced pressure to yield a dark residue. The crude product was crystallized from ethanol to yield the title compound as a yellow crystalline solid. Yield 2.4 g (67%). mp 215°–217° C. FDMS m/e=245 ($M^+$ of free base).

| analysis | calculated | found |
|---|---|---|
| C | 50.14 | 50.03 |
| H | 4.49 | 4.56 |
| N | 11.69 | 11.66 |

EXAMPLE 192

Preparation of 3-[4-(6-chloro-3-indolyl)-1,2,3,6-tetrahydropyridin-1-yl]-1-(4-indolyloxy)-2-propane ethanedioate To 5 mL of dry dimethylformamide were added 6-chloro-3-(1,2,3,6-tetrahydropyridin-4-yl)-1H-indole (0.50 g, 2.2 mmol), 1-chloro-3-(1H-indole-4-oxy)propane (0.45 g, 2.2 mmol), potassium iodide (0.36 g, 2.2 mmol) and sodium bicarbonate (0.54 g, 6.4 mmol). The mixture was stirred at 90°–100° C. under nitrogen for about 12 hours, and was then cooled and concentrated under reduced pressure. The residue was partitioned between water and chloroform, and the chloroform layer was dried (sodium sulfate) and concentrated under reduced pressure. The residue was purified by silica gel chromatography with 95/5 chloroform/methanol. The resulting free base was dissolved in 20 mL of a 1:1 methanol/ethyl acetate mixture and one equivalent of oxalic acid in methanol (5 mL) was added. The mixture was concentrated to yield a granular solid. Yield 137 mg (13%). mp 170°–174° C. FDMS m/e=405 ($M^+$ of free base).

| analysis | calculated | found |
|---|---|---|
| C | 62.97 | 63.09 |
| H | 5.28 | 5.37 |
| N | 8.47 | 8.39 |

EXAMPLE 193

Preparation of (2S)-(+)-3-[4-(6-chloro-3-indolyl)-1,2,3,6-tetrahydropyridin-1-yl]-1-(4-indolyloxy)-2-propanol To 5 mL of dry ethanol were added 6-chloro-3-(1,2,3,6-tetrahydropyridin-4-yl)-1H-indole (1.54 g, 6.61 mmol) and (S)-(+)-4-(oxiranylmethoxy)-1H-indole (1.25 g, 6.61 mmol). The mixture was heated at the reflux temperature for about 6 hours, and was then cooled and concentrated. The residue was purified by silica gel chromatography with 95/5 chloroform/methanol. The product was isolated as a yellow foam. Yield 1.52 g (55%). mp 200°–202° C. FDMS m/e=421 ($M^+$ of free base). $\alpha[D]_{589}$=+4.39 (c=1.00, dimethylsulfoxide)

| analysis | calculated | found |
|---|---|---|
| C | 68.32 | 68.04 |
| H | 5.73 | 5.72 |
| N | 9.96 | 9.85 |

EXAMPLE 194

Preparation of 3-[4-(5-chloro-3-indolyl)-1,2,3,6-tetrahydropyridin-1-yl]-1-(4-indolyloxy)propane The title compound was prepared in a fashion similar to that described in Example 192 from 5-chloro-3-(1,2,3,6-tetrahydropyridin-4-yl)-1H-indole (0.50 g, 2.2 mmol), 1-chloro-3-(1H-indole-4-oxy)propane (0.45 g, 2.2 mmol) and potassium carbonate (0.35 g, 2.5 mmol). The product was isolated as a white foam. Yield 220 mg (25%). mp 198°–202° C. FDMS m/e=406 ($M^+$ of free base).

| analysis | calculated | found |
|---|---|---|
| C | 71.01 | 71.24 |
| H | 5.96 | 6.09 |
| N | 10.35 | 10.20 |

EXAMPLE 195

Preparation of 3-[4-(6-trifluoromethyl-3-indolyl)-1,2,3,6-tetrahydropyridin-1-yl]-1-(4-indolyloxy)propane The title compound was prepared in a fashion similar to that described in Example 192 from 6-trifluoromethyl-3-(1,2,3,6-tetrahydropyridin-4-yl)-1H-indole (0.50 g, 1.9 mmol), 1-chloro-3-(1H-indole -4-oxy)propane (0.39 g, 1.9 mmol) and potassium carbonate (0.29 g, 2.1 mmol). The product was isolated as a white foam. Yield 0.53 g (64%). mp 190°–195° C. FDMS m/e=440 ($M^+$ of free base).

| analysis | calculated | found |
|---|---|---|
| C | 68.33 | 68.08 |
| H | 5.50 | 5.64 |
| N | 9.56 | 9.44 |

EXAMPLE 196

Preparation of 3-[4-(6-nitro-3-indolyl)-1,2,3,6-tetrahydropyridin-1-yl]-1-(4-indolyloxy)propane The title compound was prepared in a fashion similar to that described in Example 192 from 6-nitro-3-(1,2,3,6-tetrahydropyridin-4-yl)-1H-indole (0.50 g, 2.1 mmol), 1-chloro-3-(1H-indole-4-oxy)propane (0.43 g, 2.1 mmol) and potassium carbonate (0.32 g, 2.3 mmol). The product was isolated as an orange granular solid. Yield 0.49 g (56%). mp 215°–225° C. FDMS m/e=416 ($M^+$ of free base).

| analysis | calculated | found |
|---|---|---|
| C | 69.21 | 69.02 |
| H | 5.81 | 5.90 |
| N | 13.45 | 13.48 |

EXAMPLE 197

Preparation of (2S)-(+)-3-[4-(6-nitro-3-indolyl)-1,2,3,6-tetrahydropyridin-1-yl]-1-(4-indolyloxy)-2-propanol The title compound was prepared in a fashion similar to that described in Example 193 from 6-nitro-3-(1,2,3,6-tetrahydropyridin-4-yl)-1H-indole (1.00 g, 4.12 mmol) and (S)-(+)-4-(oxiranylmethoxy)-1H-indole (0.78 g, 4.12 mmol). The product was isolated as an orange granular solid. Yield 0.61 g (34%). mp 225°–230° C. FDMS m/e=432 ($M^+$ of free base). $\alpha[D]_{589}$=+1.98 (c=1.01, dimethylsulfoxide).

| analysis | calculated | found |
|---|---|---|
| C | 66.65 | 66.37 |
| H | 5.59 | 5.70 |
| N | 12.96 | 12.72 |

EXAMPLE 198

Preparation of (2S)-(+)-3-[4-(6,7-dichloro-3-indolyl)-1,2,3,6-tetrahydropyridin-1-yl]-1-(4-indolyloxy)-2-propanol The title compound was prepared in a fashion similar to that described in Example 193 from 6,7-dichloro-3-(1,2,3,6-tetrahydropyridin-4-yl)-1H-indole (1.00 g, 3.7 mmol) and (S)-(+)-4-(oxiranylmethoxy)-1H-indole (0.71 g, 3.7 mmol). The product was isolated as a white foam. Yield 1.17 g (69%). mp 140°–145° C. FDMS m/e=455 ($M^+$ of free base). $\alpha[D]_{589}$=+4.59 (c=1.00, dimethylsulfoxide).

| analysis | calculated | found |
|---|---|---|
| C | 63.17 | 63.36 |
| H | 5.08 | 5.30 |
| N | 9.21 | 9.47 |

EXAMPLE 199

Preparation of 3-[4-(7-chloro-3-indolyl)piperidin-1-yl]-1-(4-indolyloxy)propane

The title compound was prepared in a fashion similar to that described in Example 192 from 7-chloro-3-(piperidin-4-yl)-1H-indole (0.34 g, 1.25 mmol), 1-chloro-3-(1H-indole-4-oxy)propane (0.275 g, 1.32 mmol) and potassium carbonate (0.41 g, 3.0 mmol). The product was isolated as a white foam. Yield 240 mg (47%). mp 178°–182° C. FDMS m/e=407 ($M^+$ of free base). HRMS: calc., 408.184265; found, 408.184300

EXAMPLE 200

Preparation of (2S)-(+)-3-[4-(7-chloro-3-indolyl)-1,2,3,6-tetrahydropyridin-1-yl]-1-(4-indolyloxy)-2-propanol The title compound was prepared in a fashion similar to that described in Example 193 from 7-chloro-3-(1,2,3,6-tetrahydropyridin-4-yl)-1H-indole (0.50 g, 2.2 mmol) and (S)-(+)-4-(oxiranylmethoxy)-1H-indole (0.41 g, 2.2 mmol). The product was isolated as a white foam. Yield 370 mg (41%). mp 85°–90° C. FDMS m/e=421 (M+of free base). $\alpha[D]_{589}$=+3.62 (c=1.00, methanol/dimethylsulfoxide).

| analysis | calculated | found |
|---|---|---|
| C | 68.32 | 68.54 |
| H | 5.73 | 5.77 |
| N | 9.96 | 9.72 |

EXAMPLE 201

Preparation of (2S)-(+)-3-[4-(6-chloro-3-indolyl)piperidin-1-yl]-1-(4-indolyloxy)-2-propanol The title compound was prepared in a fashion similar to that described in Example 193 from 6-chloro-3-(piperidin-4-yl)-1H-indole (1.00 g, 4.3 mmol) and (S)-(+)-4-(oxiranylmethoxy)-1H-indole (0.81 g, 4.3 mmol). The product was isolated as a white foam. Yield 1.15 g (64%). mp 90°–95° C. FDMS m/e=423 ($M^+$ of free base). $\alpha[D]_{589}$=+8.81 (c=0.98, methanol/dimethylsulfoxide).

| analysis | calculated | found |
|---|---|---|
| C | 68.00 | 67.90 |
| H | 6.18 | 6.22 |
| N | 9.91 | 9.85 |

EXAMPLE 202

Preparation of 3-[4-(6,7-dichloro-3-indolyl)-1,2,3,6-tetrahydropyridin-1-yl]-1-(4-indolyloxy)propane The title compound was prepared in a fashion similar to that described in Example 192 from 6,7-dichloro-3-(1,2,3,6-tetrahydropyridin-4-yl)-1H-indole (0.70 g, 2.6 mmol), 1-chloro-3-(1H-indole-4-oxy)propane (0.60 g, 2.9 mmol) and potassium carbonate (0.48 g, 3.5 mmol). The product was isolated as a white granular solid. Yield 220 mg (19%). mp 224°–227° C. FDMS m/e=439 ($M^+$ of free base).

| analysis | calculated | found |
|---|---|---|
| C | 65.46 | 65.19 |
| H | 5.26 | 5.27 |
| N | 9.54 | 9.35 |

EXAMPLE 203

Preparation of 3-[4-(6,7-dichloro-3-indolyl)piperidin-1-yl]-1-(4-indolyloxy)propane The title compound was prepared in a fashion similar to that described in Example 192 from 6,7-dichloro-3-(piperidin-4-yl)-1H-indole (0.80 g, 3.0 mmol), 1-chloro-3-(1H-indole-4-oxy)propane (0.64 g, 3.1 mmol) and potassium carbonate (0.83 g, 6.0 mmol). The product was isolated as a tan foam. Yield 278 mg, 21%. mp 160°–165° C. FDMS m/e=441 ($M^+$ of free base).

| analysis | calculated | found |
|---|---|---|
| C | 65.16 | 65.43 |
| H | 5.70 | 5.60 |
| N | 9.50 | 9.66 |

EXAMPLE 204

Preparation of (2S)-(+)-3-[4-(6,7-dichloro-3-indolyl)piperidin-1-yl]-1-(4-indolyloxy)-2-propanol The title compound was prepared in a fashion similar to that described in Example 193 from 6,7-dichloro-3-(piperidin-4-yl)-1H-indole (0.80 g, 3.0 mmol) and (S)-(+)-4-(oxiranylmethoxy)-1H-indole (0.58 g, 3.1 mmol). The product was isolated as a white solid. Yield 0.64 g (47%). mp 192°–197° C. FDMS m/e=457 ($M^+$ of free base). $\alpha[D]_{589}$=+6.46 (c=0.99, methanol/dimethylsulfoxide).

| analysis | calculated | found |
|---|---|---|
| C | 62.89 | 63.09 |
| H | 5.50 | 5.61 |
| N | 9.17 | 9.22 |

EXAMPLE 205

Preparation of (2S)-(+)-3-[4-(6-trifluoromethyl-3-indolyl)piperidin-1-yl]-1-(4-indolyloxy)-2-propanol The title compound was prepared in a fashion similar to that described in Example 193 from 6-trifluoromethyl-3-(piperidin-4-yl)-1H-indole (0.50 g, 1.9 mmol) and (S)-(+)-4-(oxiranylmethoxy)-1H-indole (0.35 g, 1.9 mmol). The product was isolated as a white foam. Yield 250 mg (29%). mp 100°–105° C. FDMS m/e=457 ($M^+$ of free base). $\alpha[D]_{589}$=+8.13 (c=1.01, methanol/dimethylsulfoxide).

| analysis | calculated | found |
|---|---|---|
| C | 65.64 | 65.36 |
| H | 5.73 | 5.73 |
| N | 9.19 | 9.28 |

EXAMPLE 206

Preparation of 3-[4-(6-trifluoromethyl-3-indolyl)piperidin-1-yl]-1-(4-indolyloxy)propane The title compound was prepared in a fashion similar to that described in Example 192 from 6-trifluoromethyl-3-(piperidin-4-yl)-1H-indole (0.60 g, 2.2 mmol), 1-chloro-3-(1H-indole-4-oxy)propane (0.65 g, 2.2 mmol) and potassium carbonate (0.46 g, 3.4 mmol). The product was isolated as a white foam. Yield 165 mg (17%). mp 92°–97° C. FDMS m/e=442 ($M^+$ of free base).

| analysis | calculated | found |
|---|---|---|
| C | 68.01 | 68.02 |
| H | 5.94 | 5.98 |
| N | 9.52 | 9.70 |

EXAMPLE 207

Preparation of (2S)-(+)-3-[4-(5-methoxy-3-indolyl)-1,2,3,6-tetrahydropyridin-1-yl]-1-(4-indolyloxy)-2-propanol The title compound was prepared in a fashion similar to that described in Example 193 from 5-methoxy-3-(1,2,3,6-tetrahydropyridin-4-yl)-1H-indole (0.70 g, 3.1 mmol) and (S)-(+)-4-(oxiranylmethoxy)-1H-indole (0.58 g, 3.1 mmol). The product was isolated as a yellow foam. Yield 245 mg (19%). mp 105°–110° C. FDMS m/e=417 ($M^+$ of free base). $\alpha[D]_{589}$=+7.52 (c=1.01, methanol/dimethylsulfoxide).

| analysis | calculated | found |
|---|---|---|
| C | 71.92 | 71.70 |
| H | 6.52 | 6.62 |
| N | 10.06 | 9.85 |

EXAMPLE 208

Preparation of (2S)-(+)-3-[4-(6-chloro-5-methoxy-3-indolyl)-1,2,3,6-tetrahydropyridin-1-yl]-1-(4-indolyloxy)-2-propanol The title compound was prepared in a fashion similar to that described in Example 193 from 6-chloro-5-methoxy-3-(1,2,3,6-tetrahydropyridin-4-yl)-1H-indole (0.80 g, 3.0 mmol) and (S)-(+)-4-(oxiranylmethoxy)-1H-indole (0.60 g, 3.2 mmol). The product was isolated as a yellow foam. Yield 260 mg (19%). mp 115°–120° C. FDMS m/e=452 ($M^+$ of free base). $\alpha[D]_{589}$=+6.62 (c=1.03, dimethylsulfoxide).

| analysis | calculated | found |
|---|---|---|
| C | 66.44 | 66.55 |
| H | 5.80 | 5.94 |
| N | 9.30 | 9.24 |

EXAMPLE 209

Preparation of (2S)-(+)-3-[4-(6-methoxy-3-indolyl)-1,2,3,6-tetrahydropyridin-1-yl]-1-(4-indolyloxy)-2-propanol The title compound was prepared in a fashion similar to that described in Example 193 from 6-methoxy-3-(1,2,3,6-tetrahydropyridin-4-yl)-1H-indole (0.80 g, 3.5 mmol) and (S)-(+)-4-(oxiranylmethoxy)-1H-indole (0.66 g, 3.5 mmol). The resulting free base was recrystallized from methanol to yield a white crystalline solid. Yield 0.63 g (43%). mp 155°–160° C. FDMS m/e=417 (M⁺ of free base). α[D]₅₈₉= +4.30 (c=0.98, methanol/dimethylsulfoxide).

| analysis | calculated | found |
|---|---|---|
| C | 71.92 | 71.88 |
| H | 6.52 | 6.61 |
| N | 10.06 | 10.11 |

EXAMPLE 210

Preparation of (2S)-(+)-3-[4-(5-fluoro-3-indolyl)piperidin-1-yl]-1-(4-indolyloxy)-2-propanol The title compound was prepared in a fashion similar to that described in Example 193 from 5-fluoro-3-(piperidin-4-yl)-1H-indole (0.87 g, 4.0 mmol) and (S)-(+)-4-(oxiranylmethoxy)-1H-indole (0.76 g, 4.0 mmol). The product was isolated as a white foam. Yield 1.14 g (70%). mp 94°–97° C. FDMS m/e=407 (M⁺ of free base). α[D]₅₈₉=+8.36 (c=1.00, methanol/dimethylsulfoxide).

| analysis | calculated | found |
|---|---|---|
| C | 70.74 | 70.58 |
| H | 6.43 | 6.68 |
| N | 10.31 | 10.23 |

EXAMPLE 211

Preparation of (2S)-(+)-3-[4-(6-fluoro-3-indolyl)piperidin-1-yl]-1-(4-indolyloxy)-2-propanol The title compound was prepared in a fashion similar to that described in Example 193 from 6-fluoro-3-(piperidin-4-yl)-1H-indole (1.00 g, 4.6 mmol) and (S)-(+)-4-(oxiranylmethoxy)-1H-indole (0.91 g, 4.8 mmol). The product was isolated as a white foam. Yield 0.75 g (40%). mp 94°–97° C. FDMS m/e=407 (M⁺ of free base). α[D]₅₈₉=+7.97 (c=1.00, methanol/dimethylsulfoxide).

| analysis | calculated | found |
|---|---|---|
| C | 70.74 | 70.49 |
| H | 6.43 | 6.36 |
| N | 10.31 | 10.53 |

EXAMPLE 212

Preparation of (2S)-(+)-3-[4-(6-fluoro-3-indolyl)-1,2,3,6-tetrahydropyridin-1-yl]-1-(4-indolyloxy)-2-propanol The title compound was prepared in a fashion similar to that described in Example 193 from 6-fluoro-3-(1,2,3,6-tetrahydropyridin-4-yl)-1H-indole (1.00 g, 4.63 mmol) and (S)-(+)-4-(oxiranylmethoxy)-1H-indole (0.88 g, 4.6 mmol). The resulting free base was obtained as a yellow foam. Yield 1.2 g (64%). mp 95°–100° C. FDMS m/e=405 (M⁺ of free base). α[D]₅₈₉=5.15 (c=1.01, dimethylsulfoxide).

| analysis | calculated | found |
|---|---|---|
| C | 71.09 | 70.81 |
| H | 5.97 | 6.00 |
| N | 10.36 | 10.13 |

EXAMPLE 213

Preparation of (2S)-(+)-3-[4-(5-fluoro-3-indolyl)-1,2,3,6-tetrahydropyridin-1-yl]-1-(4-indolyloxy)-2-propanol The title compound was prepared in a fashion similar to that described in Example 193 from 5-fluoro-3-(1,2,3,6-tetrahydropyridin-4-yl)-1H-indole (1.00 g, 4.63 mmol) and (S)-(+)-4-(oxiranylmethoxy)-1H-indole (0.90 g, 4.8 mmol). The resulting free base was isolated as a white foam. Yield 1.04 g (55%). mp 95°–100° C. FDMS m/e=405 (M⁺ of free base). α[D]₅₈₉=5.91 (c=1.01, dimethylsulfoxide).

| analysis | calculated | found |
|---|---|---|
| C | 71.09 | 70.86 |
| H | 5.97 | 6.06 |
| N | 10.36 | 10.19 |

EXAMPLE 214

Preparation of (2S)-(+)-3-[4-(4-fluoro-3-indolyl)-1,2,3,6-tetrahydropyridin-1-yl]-1-(4-indolyloxy)-2-propanol The title compound was prepared in a fashion similar to that described in Example 193 from 4-fluoro-3-(1,2,3,6-tetrahydropyridin-4-yl)-1H-indole (0.50 g, 2.3 mmol) and (S)-(+)-4-(oxiranylmethoxy)-1H-indole (0.44 g, 2.3 mmol). The resulting free base was obtained as a yellow foam. Yield 0.14 g (15%). mp 90°–95° C. FDMS m/e=405 (M⁺ of free base).

| analysis | calculated | found |
|---|---|---|
| C | 71.09 | 71.22 |
| H | 5.97 | 5.98 |
| N | 10.36 | 10.62 |

EXAMPLE 215

Preparation of (2S)-(+)-3-[4-(6-nitro-3-indolyl)piperidin-1-yl]-1-(4-indolyloxy)-2-propanol The title compound was prepared in a fashion similar to that described in Example 193 from 6-nitro-3-(piperidin-4-yl)-1H-indole (0.49 g, 2.0 mmol) and (S)-(+)-4-(oxiranylmethoxy)-1H-indole (0.40 g, 2.1 mmol). The product was isolated as a yellow crystalline solid. Yield 0.34 g (37%). mp 212°–214° C. FDMS m/e=434 (M⁺ of free base).

| analysis | calculated | found |
|---|---|---|
| C | 66.35 | 66.34 |
| H | 6.03 | 6.11 |
| N | 12.90 | 12.68 |

EXAMPLE 216

Preparation of (2S)-(+)-3-[4-(7-methyl-3-indolyl)piperidin-1-yl]-1-(4-indolyloxy)-2-propanol The title compound was prepared in a fashion similar to that described in Example 1 using (S)-(+)-4-(oxiranylmethoxy)-1H-indole (0.280 g, 1.48 mmol) and 7-methyl-3-(piperidin-4-yl)-1H-indole (0.290 g, 1.39 mmol) using ethanol as reaction solvent. Yield 0.320 g (57%) as a tan foam. FDMS m/e=404 (M+ of free base). $\alpha[D]_{589}$=11.6 (c=0.98, dimethylsulfoxide).

| analysis | calculated | found |
|---|---|---|
| C | 74.41 | 73.89 |
| H | 7.24 | 7.39 |
| N | 10.41 | 10.15 |

EXAMPLE 217

Preparation of (2S)-(+)-3-[4-(6-methyl-3-indolyl)-piperidin-1-yl]-1-(4-indolyloxy)-2-propanol The title compound was prepared in a fashion similar to that described in Example 1 using (S)-(+)-4-(oxiranylmethoxy)-1H-indole (0.145 g, 0.767 mmol) and 6-methyl-3-(piperidin-4-yl)-1H-indole (0.150 g, 0.697 mmol) using ethanol as reaction solvent. Yield 0.140 g (49%) as a tan foam. FDMS m/e=403 (M+ of free base). $\alpha[D]_{589}$=+3.8 (c=0.98, dimethylsulfoxide).

| analysis | calculated | found |
|---|---|---|
| C | 74.41 | 73.57 |
| H | 7.24 | 7.08 |
| N | 10.41 | 10.42 |

EXAMPLE 218

Preparation of 3-[4-(7-methyl-3-indolyl)-1,2,3,6-tetrahydropyridin-1-yl]-1-(4-indolyloxy)propane The title compound was prepared in a fashion similar to that described in Example 99 using 1-chloro-3-(1H-indole-4-oxy)propane (0.499 g, 2.4 mmol) and 7-methyl-3-(1,2,3,6-tetrahydropyridin-4-yl)-1H-indole (0.509 g, 2.4 mmol) in the presence of 2.0 equivalents of $K_2CO_3$ (0.593, 4.3 mmol) in dimethylformamide at 90° C. Yield 0.383 g (41%) of a tan powder. mp 166–169 C. FDMS m/e=405 (M+ of free base).

| analysis | calculated | found |
|---|---|---|
| C | 77.89 | 77.83 |
| H | 7.06 | 6.89 |
| N | 10.90 | 10.67 |

EXAMPLE 219

Preparation of 3-[4-(6-methyl-3-indolyl)-1,2,3,6-tetrahydropyridin-1-yl]-1-(4-indolyloxy)propane The title compound was prepared in a fashion similar to that described in Example 99 using 1-chloro-3-(1H-indole-4-oxy)propane (0.273 g, 2.4 mmol) and 6-methyl-3-(1,2,3,6-tetrahydropyridin-4-yl)-1H-indole (0.279 g, 2.4 mmol) in the presence of 2.0 equivalents of $K_2CO_3$ (0.593, 4.3 mmol) in dimethylformamide at 90° C. Yield 0.167 g (50%) of a tan powder. mp C. FDMS m/e=405 (M+ of free base).

| analysis | calculated | found |
|---|---|---|
| C | 77.89 | 76.91 |
| H | 7.06 | 6.82 |
| N | 10.90 | 10.48 |

The following synthesis illustrates a particularly useful and preferred synthesis of the compound of Example 34 above, which is a particularly interesting compound.

Example A

Preparation of (2S)-(−)-1-(4-indolyloxy)-3-[4-hydroxy-4-(3-methoxyphenyl)piperidin-1-yl]-2-propanol succinate Preparation a. Preparation of 4-hydroxy-4-(3-methoxyphenyl)-1-benzylpiperidine hydrochloride To a 3 L, 3-necked round-bottomed flask equipped with a magnetic stirring bar, condenser, thermocouple and addition funnel were added 13.4 g of magnesium turnings. A liter of tetrahydrofuran and 0.07 g of iodine were added, and the contents was stirred under nitrogen at ambient temperature. Approximately 2 mL of 3-bromoanisole was added to the flask. To the stirring mixture was then added slowly a solution of 92.4 g of 3-bromoanisole in 750 mL of tetrahydrofuran, adding the solution slowly while maintaining the temperature below 66° C. When the addition was complete, the green-black reaction mixture was stirred at 59°–62° C. for an additional hour, and then cooled.

To the mixture was then slowly added 94.6 g of 1-benzyl-4-piperidone, while cooling the flask to keep the temperature below 35° C. The addition funnel was rinsed with 30 mL of tetrahydrofuran. Then the mixture was cooled to approximately 0° C., and 500 mL of 1N hydrochloric acid was added slowly, holding the temperature below 10° C. The mixture was then extracted with 1 L of toluene, and the yellow organic layer was removed and dried over anhydrous magnesium sulfate. The resulting dry organic solution was cooled and 1 molar equivalent of hydrogen chloride, dissolved in methanol, was added slowly, maintaining the temperature below 10° C. The slurry was stirred for an hour in the cold and filtered, and the solids were washed with additional toluene. The wet cake was dried at 40° C. for at least 15 hours to obtain the desired compound in potency of 75–90% in different preparations.

Preparation b. Preparation of (S)-(+)-4-(oxiranylmethoxy)-1H-indole

A 3.2 g portion of 4-hydroxy-1H-indole was dissolved in 31 mL of dimethylformamide in a 50 mL flask equipped with a magnetic stirrer, nitrogen bubbler and thermometer. To it was added 1.27 g of sodium methoxide and the mixture was stirred until a blue-black solution resulted. The warm mixture was placed under vacuum for 5 minutes to remove most of the resulting methanol. To the mixture was added 6 g of oxiranylmethoxysulfonyl-3-nitrobenzene, resulting in an exotherm to about 37° C. The mixture was stirred at ambient temperature for 1 hour, and was then poured into a separatory funnel containing 55 mL of methyl t-butyl ether and 80 mL of water. The mixture was shaken well, and the layers were separated. The organic layer was removed and the aqueous layer was extracted with 2×55 mL of methyl t-butyl ether. The organic layers were combined and back-extracted with 50 mL of 5% aqueous lithium chloride. The layers were separated again, and the organic layer was dried with magnesium sulfate and filtered. The organic filtrate was concentrated under vacuum to about 15 mL of volume, and was seeded with pure desired product and stirred. The product was crystallized to a thick slurry to which 20 mL of heptane was slowly added. The mixture was stirred for one hour more and filtered, and the filter cake was rinsed with 3:1 heptane:methyl t-butyl ether, and then with heptane. The product was dried in a vacuum oven at 40° C. to obtain about 3.5 g of product.

Preparation c. Preparation of (2S)-(−)-1-(4-indolyloxy)-3-[4-hydroxy-4-(3-methoxyphenyl)piperidin-1-yl]-2-propanol succinate Three g of 5% palladium/carbon was slurried in 15 mL of water in a 500 mL Parr bottle at ambient temperature. To the mixture was added 30 g of the product of Preparation a, followed by 70 mL of methanol, and the bottle was placed into the shaker apparatus under 50 psi of hydrogen. The mixture was heated at 50° C. and shaken for 2.5 hours, and then cooled. The mixture was filtered into a 500 mL 3-neck flask equipped with a condenser, magnetic stirrer, thermometer and temperature control, and the filter cake was rinsed lightly with 5 mL each of methanol and water. To the filtrate was added 18 mL of 5N aqueous sodium hydroxide, and the cloudy mixture was stirred for 15 minutes. To it was added 16.6 g of the product of Preparation b, and the mixture was heated to 60° C. and stirred for 1.5 hours. To the reaction mixture were added 100 mL of water and 160 mL of ethyl acetate, and the 2-phase mixture was stirred vigorously. A pH of about 10 was observed. The layers were separated, and the organic layer was warmed to about 60° C. with stirring and 10.2 g of succinic acid was added and rinsed in with 20 mL of methanol. The mixture was stirred slowly for about 6 hours with seeding. The slurry was then cooled in an ice bath, and stirred at a low temperature for 2 hours. The solids were removed by filtration and rinsed with 100 mL of 3:1 ethyl acetate:methanol and then with 50 mL of ethyl acetate. The dry cake was dried at 50° C. overnight. The yield was 35.5 g, at a potency of 99.1%. The enantiomeric purity was 100%, and the corrected yield was 79.3% of theory.

A small second crop of product, amounting to about 3.5 g at a potency of 95%, was obtained by concentrating the filtrate to an oil, redissolving it in a minimum volume of 5:1 ethyl acetate:methanol, and repeated cooling and filtration.

Serotonin $1_A$ receptor activity

The compounds of the present invention are active at the serotonin $1_A$ receptor, particularly as antagonists and as partial agonists at that receptor, and are distinguished by their selectivity. Previously known compounds with that activity typically have the disadvantage of possessing other non-serotonin related central nervous system activities as well. It is now well understood by pharmacologists and physicians that pharmaceuticals which have a single physiological activity, or which are much more active in the desired activity than in their other activities, are much more desirable for therapy than are compounds which have multiple activities at about the same dose.

Many other serotonin $1_A$ receptor antagonists typically have α-adrenergic or β-adrenergic activity as well, and are therefore nonselective for 5HT-$1_A$ activity.

The 5HT-$1_A$ receptor binding potency of the present compounds has been measured by a modification of the binding assay described by Taylor, et al. (*J. Pharmacol. Exp. Ther.* 236, 118–125, 1986); and Wong, et al., *Pharm. Biochem. Behav.* 46, 173–77 (1993). Membranes for the binding assay were prepared from male Sprague-Dawley rats (150–250 g). The animals were killed by decapitation, and the brains were rapidly chilled and dissected to obtain the hippocampi. Membranes from the hippocampi were either prepared that day, or the hippocampi were stored frozen (−70°) until the day of preparation. The membranes were prepared by homogenizing the tissue in 40 volumes of ice-cold Tris-HCl buffer (50 mM, pH 7.4 at 22°) using a homogenizer for 15 sec., and the homogenate was centrifuged at 39800×g for 10 min. The resulting pellet was then resuspended in the same buffer, and the centrifugation and resuspension process was repeated three additional times to wash the membranes. Between the second and third washes the resuspended membranes were incubated for 10 min. at 37° to facilitate the removal of endogenous ligands. The final pellet was resuspended in 67 mM Tris-HCl, pH 7.4, to a concentration of 2 mg of tissue original wet weight/200 μl. This homogenate was stored frozen (−70°) until the day of the binding assay. Each tube for the binding assay had a final volume of 800 μl and contained the following: Tris-HCl (50 mM), pargyline (10 μM), CaCl$_2$ (3 mM), [$^3$H]8-OH-DPAT (1.0 nM), appropriate dilutions of the drugs of interest, and membrane resuspension equivalent to 2 mg of original tissue wet weight, for a final pH of 7.4. The assay tubes were incubated for either 10 min. or 15 min. at 37°, and the contents were then rapidly filtered through GF/B filters (pretreated with 0.5% polyethylenimine), followed by four one-ml washes with ice-cold buffer. The radioactivity trapped by the filters was quantitated by liquid scintillation spectrometry, and specific [$^3$H]8-OH-DPAT binding to the 5-HT$1_A$ sites was defined as the difference between [$^3$H]8-OH-DPAT bound in the presence and absence of 10 μM 5-HT.

IC$_{50}$ values, i.e., the concentration required to inhibit 50% of the binding, were determined from 12-point competition curves using nonlinear regression (SYSTAT, SYSTAT, Inc., Evanston, Ill.).

Additional binding assays of some of the present compounds have been carried out by an assay method which uses a cloned cell line which expresses the serotonin $1_A$ receptor, rather than the hippocampal membranes. Such cloned cell lines have been described by Fargin, et al., *J. Bio. Chem.*, 264, 14848–14852 (1989), Aune, et al., *J. Immunology*, 151, 1175–1183 (1993), and Raymond, et al., *Naunyn-Schmiedeberg's Arch. Pharmacol.*, 346, 127–137 (1992). Results from the cell line assay are substantially in agreement with results from the hippocampal membrane assay.

The efficacy of the compounds of Formulae XI and XIII to inhibit the reuptake of serotonin has been determined by a paroxetine binding essay, the usefulness of which is set out by Wong, et al., *Neuropsychopharmacology*, 8, 23–33 (1993). Synaptosomal preparations from rat cerebral cortex were made from the brains of 100–150 g Sprague-Dawley rats which were killed by decapitation. The cerebral cortex was homogenized in 9 volumes of a medium containing 0.32M sucrose and 20 μM glucose. The preparations were resuspended after centrifugation by homogenizing in 50 volumes of cold reaction medium (50 μM sodium chloride, 50 μM potassium chloride, pH 7.4) and centrifuging at 50,000 g for 10 minutes. The process was repeated two times with a 10-minute incubation at 37° C. between the second and third washes. The resulting pellet was stored at −70° C.

until use. Binding of $^3$H-paroxetine to 5-HT uptake sites was carried out in 2 ml reaction medium containing the appropriate drug concentration, 0.1 nM $^3$H-paroxetine, and the cerebral cortical membrane (50 μg protein/tube). Samples were incubated at 37° C. for 30 minutes; those containing 1 μM fluoxetine were used to determine nonspecific binding of $^3$H-paroxetine. After incubation, the tubes were filtered through Whatman GF/B filters, which were soaked in 0.05% polyethylenimine for 1 hour before use, using a cell harvester by adding about 4 ml cold Tris buffer (pH 7.4), aspirating, and rinsing the tubes three additional times. Filters were then placed in scintillation vials containing 10 ml scintillation fluid, and the radioactivity was measured by liquid scintillation spectrophotometry.

Results of testing representative compounds of Formulae XI and XIII by the above method showed potent reuptake activity, in many cases activity in the low nM range.

The pharmacological activities which have been described immediately above provide the mechanistic basis for the pharmaceutical utility of the compounds described in this document. A number of pharmaceutical utilities will be described below.

Throughout this document, the person or animal to be treated will be described as the "subject", and it will be understood that the most preferred subject is a human. However, it must be noted that the study of adverse conditions of the central nervous system in non-human animals is only now beginning, and that some instances of such treatments are coming into use. For example, fluoxetine, and perhaps other serotonin reuptake inhibitors, are being used in companion animals such as dogs for the treatment of behavioral problems and the like. Accordingly, use of the present compounds in non-human animals is contemplated. It will be understood that the dosage ranges for other animals will necessarily be quite different from the doses administered to humans, and accordingly that the dosage ranges described below in the section on tobacco withdrawal must be recalculated. For example, a small dog may be only 1/10th of a typical human's size, and it will therefore be necessary for a much smaller dose to be used. The determination of an effective amount for a certain non-human animal is carried out in the same manner described below in the case of humans, and veterinarians are well accustomed to such determinations.

The activity of the compounds at the serotonin $1_A$ receptor provides a method of affecting the serotonin $1_A$ receptor which comprises administering to a subject in need of such treatment an effective amount of a compound of Formula XII. Reasons for the necessity of affecting the $1_A$ receptor will be described in detail below, but in all cases the effect on the serotonin $1_A$ receptor is brought about through the compounds' potency as antagonists or partial agonists at that receptor. A subject in need of a modification of the effects of the 5HT-$1_A$ receptor is one having one or more of the specific conditions and problems to be further described, or a condition or problem not yet recognized as created by an imbalance or malfunction of the 5HT-$1_A$ receptor, since research on the central nervous system is presently ongoing in many fields and newly discovered relationships between receptors and therapeutic needs are continually being discovered. In all cases, however, it is the compounds' ability to affect the serotonin $1_A$ receptor which creates their physiological or therapeutic effects.

An effective amount of a compound for affecting the serotonin $1_A$ receptor is the amount, or dose, of the compound which provides the desired effect in the subject under diagnosis or treatment. The amount is an individualized determination, and physicians are well accustomed to adjusting effective amounts of pharmaceuticals based on observations of the subject. The effective amount of the present compounds is discussed in some detail below, in the discussion about the treatment of tobacco withdrawal symptoms, and that discussion is applicable to the determination of the effective amount in all treatment methods.

Further, the activity of compounds of Formula XIII in the inhibition of the reuptake of serotonin provides a method of inhibiting the reuptake of serotonin comprising administering to a subject in need of such treatment an effective amount of a compound of that formula. It is now known that numerous physiological and therapeutic benefits are obtained through the administration of drugs which inhibit the reuptake of serotonin. The treatment of depression with drugs of the class of which fluoxetine is the leader has become perhaps the greatest medical breakthrough of the past decade. Numerous other treatment methods carried out by the administration of the compounds of Formula XIII will be set out in detail below. Again, the effective amount of a compound for the inhibition of serotonin reuptake, or for a specific therapeutic method which depends on the inhibition of reuptake, is determined in the manner described below under the heading of smoking withdrawal.

The unique combination of 5HT-$1_A$ receptor activity and serotonin reuptake inhibition possessed by the compounds of Formula XIII afford a method of providing to a subject both physiological activities with a single administration of a compound of that formula. As discussed in the Background section of this document, the value of combining the two effects has been discussed in the literature, and it is believed that the present compounds are the first to provide both physiological effects in a single drug. It is presently believed that the result of administration of a compound of Formula XII is to provide physiological and therapeutic treatment methods which are typical of those provided by presently known serotonin reuptake inhibitors, but with enhanced efficacy and quicker onset of action. In addition, of course, all of the physiological and therapeutic methods provided by compounds which affect the serotonin $1_A$ receptor are provided by the compounds of Formula XIII as well. It will be noted that Formula XIII is included in the scope of the 5HT-$1_A$ receptor-active compounds of Formula XII.

The activities of Formula XIII compounds at the 5HT-$1_A$ receptor and in reuptake inhibition are of comparable potencies, so a single effective amount is effective for both purposes.

Further discussion of specific therapeutic methods provided by the dual activity compounds of Formula XIII, and the diseases and conditions advantageously treated therewith, will be provided below.

Tobacco or nicotine withdrawal

It is well known that the chronic administration of nicotine results in tolerance and, eventually, dependence. The use of tobacco has become extremely widespread in all countries, despite the well known adverse effects of the use of tobacco in all its forms. Thus, it is clear that tobacco use is extremely habit-forming, if not addictive, and that its use provides sensations to the user which are pleasant and welcome, even though the user may be fully aware of the drastic long term ill effects of its use.

Rather recently, vigorous campaigns against the use of tobacco have taken place, and it is now common knowledge that the cessation of smoking brings with it numerous unpleasant withdrawal symptoms, which include irritability, anxiety, restlessness, lack of concentration, lightheadedness, insomnia, tremor, increased hunger and weight gain, and, of course, a craving for tobacco.

At the present time, probably the most widely used therapy to assist the cessation of tobacco use is nicotine replacement, by the use of nicotine chewing gum or nicotine-providing transdermal patches. It is widely known, however, that nicotine replacement is less effective without habit-modifying psychological treatment and training.

Thus, the present method of preventing or alleviating the symptoms caused by withdrawal or partial withdrawal from the use of tobacco or of nicotine comprises the previously discussed method of affecting the serotonin $1_A$ receptor, in that the treatment method comprises the administration of an effective amount of one of the serotonin $1_A$ receptor-active compounds of Formula XII to the subject. The method of the present invention is broadly useful in assisting persons who want to cease or reduce their use of tobacco or nicotine. Most commonly, the form of tobacco use is smoking, most commonly the smoking of cigarettes. The present invention is also helpful, however, in assisting in breaking the habit of all types of tobacco smoking, as well as the use of snuff, chewing tobacco, etc. The present method is also helpful to those who have replaced, or partially replaced, their use of tobacco with the use of nicotine replacement therapy. Thus, such subjects can be assisted to reduce and even eliminate entirely their dependence on nicotine in all forms.

A particular benefit of therapy with the present compounds is the elimination or reduction of the weight gain which very often results from reducing or withdrawing from use of tobacco or nicotine.

It will be understood that the present invention is useful for preventing or alleviating the withdrawal symptoms which afflict subjects who are trying to eliminate or reduce their use of tobacco or nicotine. The common withdrawal symptoms of such people include, at least, irritability, anxiety, restlessness, lack of concentration, insomnia, nervous tremor, increased hunger and weight gain, light-headedness, and the craving for tobacco or nicotine. The prevention or alleviation of such symptoms, when they are caused by or occur in conjunction with ceasing or reducing the subject's use of tobacco or nicotine is a desired result of the present invention and an important aspect of it.

The invention is carried out by administering an effective amount of a compound of Formula XII to a subject who is in need of or carrying out a reduction or cessation of tobacco or nicotine use.

The effective amount of compound to be administered, in general, is from about 1 to about 100 mg/day; as usual, the daily dose may be administered in a single bolus, or in divided doses, depending on the judgment of the physician in charge of the case. A more preferred range of doses is from about 5 to about 100 mg/day; other dosage ranges which may be preferred in certain circumstances are from about 10 to about 50 mg/day; from about 5 to about 50 mg/day; from about 10 to about 25 mg/day; and a particularly preferred range is from about 20 to about 25 mg/day. It will be understood that the effective amount for a given subject is always to be set by the judgment of the attending physician, and that the dose is subject to modification based on the size of the subject, the lean or fat nature of the subject, the characteristics of the particular compound chosen, the intensity of the subject's tobacco habit, the intensity of the subject's withdrawal symptoms, and psychological factors which may affect the subject's physiological responses. Thus, the effective amount is the amount required to prevent or alleviate the symptoms of withdrawal or partial withdrawal in the subject under treatment.

The effect of the compounds in alleviating the symptoms of nicotine withdrawal was evaluated in rats by an auditory startle test, which was carried out as follows.

Procedures for Nicotine Withdrawal Studies

Animals: Male Long Evans rats were individually housed in a controlled environment on a 12 hour light-dark cycle and were given free access to food (Purina Rodent Chow) and water. All treatment groups contained 8–10 rats.

Chronic Nicotine Treatment: Rats were anesthetized with halothane and Alzet osmotic minipumps (Alza Corporation, Palo Alto, Calif., Model 2ML2) were implanted subcutaneously. Nicotine ditartrate was dissolved in physiological saline. Pumps were filled with either nicotine ditartrate (6 mg/kg base/day) or physiological saline. Twelve days following implantation of pumps, rats were anesthetized with halothane and the pumps were removed.

Auditory Startle Response: The sensory motor reactions [auditory startle response (peak amplitude Vmax)] of individual rats was recorded using San Diego Instruments startle chambers (San Diego, Calif.). Startle sessions consisted of a 5-minute adaptation period at a background noise level of 70±3 dBA immediately followed by 25 presentations of auditory stimuli (120±2 dBA noise, 50 ms duration) presented at 8-second intervals. Peak startle amplitudes were then averaged for all 25 presentations of stimuli for each session. Auditory startle responding was evaluated daily at 24 hour intervals on days 1–4 following nicotine withdrawal. Representative compounds were found to attenuate the startle response during nicotine withdrawal at very low effective doses.

Combination with reuptake inhibitors

A further application of the compounds of Formula XII is their use in combination with a serotonin reuptake inhibitor to potentiate the action of those drugs by increasing the availability of serotonin, as well as norepinephrine and dopamine, in the brain of subjects to whom the drug combination is administered. Typical and appropriate reuptake inhibitors (SRI) are fluoxetine, duloxetine, venlafaxine, sertraline, milnacipran, citalopram, fluvoxamine and paroxetine. Accordingly, the present invention provides a method for potentiating the action of a serotonin reuptake inhibitor, particularly one of the group consisting of fluoxetine, duloxetine, venlafaxine, milnacipran, sertraline, citalopram, fluvoxamine and paroxetine, in increasing the availability of serotonin, norepinephrine and dopamine in the brain, comprising administering said serotonin reuptake inhibitor in combination with the present method of affecting the serotonin $1_A$ receptor. The invention also provides pharmaceutical compositions which comprise a serotonin reuptake inhibitor in combination with a compound of Formula I, and a method of treating a pathological condition which is created by or is dependent upon decreased availability of serotonin, dopamine or norepinephrine, which method comprises administering the same adjunctive therapy to a subject in need of such treatment.

It will be understood that it is preferred to carry out the present combination aspect of the invention with compounds of Formula XII which are outside the scope of Formula XIII, since the Formula XIII compounds clearly provide, individually, the benefit of the presently described combination. However, it is entirely possible to administer a compound of Formula XIII, as a special case of the present combination, in combination with a conventional serotonin reuptake inhibitor in order to obtain still further enhanced results in potentiating the serotonin reuptake inhibition.

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson, et al., *J. Med. Chem.* 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers.

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule.

Venlafaxine is known in the literature, and its method of synthesis and its activity as an inhibitor of serotonin and norepinephrine uptake are taught by U.S. Pat. No. 4,761,501. Venlafaxine is identified as compound A in that patent.

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret, et al., *Neuropharmacology* 24, 1211–19 (1985), describe its pharmacological activities.

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen, et al., *Eur. J. Pharmacol.* 41, 153 (1977), and reports of its clinical effectiveness in depression may be found in Dufour, et al., *Int. Clin. Psychopharmacol.* 2, 225 (1987), and Timmerman, et al., ibid., 239.

Fluvoxamine, 5-methoxy-1-[4-(trifluoromethyl)phenyl]-1-pentanone 0-(2-aminoethyl)oxime, is taught by U.S. Pat. No. 4,085,225. Scientific articles about the drug have been published by Claassen, et al., *Brit. J. Pharmacol*, 60, 505 (1977); and De Wilde, et al., *J. Affective Disord.* 4, 249 (1982); and Benfield, et al., *Drugs* 32, 313 (1986).

Sertraline, 1-(3,4-dichlorophenyl)-4-methylaminotetralin, is disclosed in U.S. Pat. No. 4,536,518.

Paroxetine, trans-(−)-3-[(1,3-benzodioxol-5-yloxy)methyl]-4-(4-fluorophenyl)piperidine, may be found in U.S. Pat. Nos. 3,912,743 and 4,007,196. Reports of the drug's activity are in Lassen, *Eur. J. Pharmacol.* 47, 351 (1978); Hassan, et al., *Brit. J. Clin. Pharmacol.* 19, 705 (1985); Laursen, et al., *Acta Psychiat. Scand.* 71, 249 (1985); and Battegay, et al., *Neuropsychobiology* 13, 31 (1985).

All of the U.S. patents which have been mentioned above in connection with compounds used in the present invention are incorporated herein by reference.

In general, combinations and methods of treatment using fluoxetine or duloxetine as the SRI are preferred.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

The dosages of the drugs used in the present combination must, in the final analysis, be set by the physician in charge of the case, using knowledge of the drugs, the properties of the drugs in combination as determined in clinical trials, and the characteristics of the subject, including diseases other than that for which the physician is treating the subject. General outlines of the dosages, and some preferred human dosages, can and will be provided here. Dosage guidelines for some of the drugs will first be given separately; in order to create a guideline for any desired combination, one would choose the guidelines for each of the component drugs.

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day;

Milnacipran: from about 10 to about 100 mg once-twice/day; preferred, from about 25 to about 50 mg twice/day;

Citalopram: from about 5 to about 50 mg once/day; preferred, from about 10 to about 30 mg once/day;

Fluvoxamine: from about 20 to about 500 mg once/day; preferred, from about 50 to about 300 mg once/day;

Paroxetine: from about 5 to about 100 mg once/day; preferred, from about 50 to about 300 mg once/day.

In more general terms, one would create a combination of the present invention by choosing a dosage of SRI according to the spirit of the above guideline, and choosing a dosage of the compound of Formula XII in the ranges taught above.

The adjunctive therapy of the present invention is carried out by administering a SRI together with a compound of Formula XII in any manner which provides effective levels of the two compounds in the body at the same time. All of the compounds concerned are orally available and are normally administered orally, and so oral administration of the adjunctive combination is preferred. They may be administered together, in a single dosage form, or may be administered separately.

However, oral administration is not the only route or even the only preferred route. For example, transdermal administration may be very desirable for subjects who are forgetful or petulant about taking oral medicine. One of the drugs may be administered by one route, such as oral, and the other may be administered by the trans-dermal, percutaneous, intravenous, intramuscular, intranasal or intrarectal route, in particular circumstances. The route of administration may be varied in any way, limited by the physical properties of the drugs and the convenience of the subject and the caregiver.

It is particularly preferred, however, for the adjunctive combination to be administered as a single pharmaceutical composition, and so pharmaceutical compositions incorporating both a SRI and a compound of Formula XII are important embodiments of the present invention. Such compositions may take any physical form which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of both compounds, or may contain a fraction of the daily doses, such as one-third of the doses. Alternatively, each dosage unit may contain the entire dose of one of the compounds, and a fraction of the dose of the other compound. In such case, the subject would daily take one of the combination dosage units, and one or more units containing only the other compound. The amounts of each drug to be contained in each dosage unit depends on the identity of the drugs chosen for the therapy, and other factors such as the indication for which the adjunctive therapy is being given.

As stated above, the benefit of the adjunctive therapy is its ability to augment the increase in availability of serotonin, norepinephrine and dopamine caused by the SRI compounds, resulting in improved activity in treating the various conditions described below in detail. The increase in availability of serotonin is particularly important and is a preferred aspect of the invention. Further, the invention provides a more rapid onset of action than is usually provided by treatment with the SRI alone.

The therapeutic applications of the treatment method, described at length above, comprising the combined administration of a serotonin reuptake inhibitor and a compound of Formula XII, and the method comprising the administration of a compound of Formula XIII, are substantially the same, since the effect of both methods of treatment is to potentiate the action of serotonin reuptake inhibition. Accordingly, specific methods of treatment, and the conditions and diseases to be treated therewith, of both methods will be discussed as one, in the following section.

Preferred pathological conditions to be treated by the present treatment methods include depression, bulimia, obsessive-compulsive disease and obesity. Another preferred condition more specific to combinations including preferably duloxetine but also venlafaxine and milnacipran is urinary incontinence.

Depression in its many variations has recently become much more visible to the general public than it has previously been. It is now recognized as an extremely damaging disorder, and one that afflicts a surprisingly large fraction of the human population. Suicide is the most extreme symptom of depression, but millions of people, not quite so drastically afflicted, live in misery and partial or complete uselessness, and afflict their families as well by their affliction. The introduction of fluoxetine was a breakthrough in the treatment of depression, and depressives are now much more likely to be diagnosed and treated than they were only a decade ago. Duloxetine is in clinical trials for the treatment of depression and is likely to become a marketed drug for the purpose.

Depression is often associated with other diseases and conditions, or caused by such other conditions. For example, it is associated with Parkinson's disease; with HIV; with Alzheimer's disease; and with abuse of anabolic steroids. Depression may also be associated with abuse of any substance, or may be associated with behavioral problems resulting from or occurring in combination with head injuries, mental retardation or stroke. Depression in all its variations is a preferred target of treatment with the present adjunctive therapy method and compositions.

Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted subject may be unable to do anything but carry out the rituals required by the disease. Fluoxetine is approved in the United States and other countries for the treatment of obsessive-compulsive disease and has been found to be effective.

Obesity is a frequent condition in the American population. It has been found that fluoxetine will enable an obese subject to lose weight, with the resulting benefit to the circulation and heart condition, as well as general well being and energy.

Urinary incontinence is classified generally as stress or urge incontinence, depending on whether its root cause is the inability of the sphincter muscles to keep control, or the overactivity of the bladder muscles. Duloxetine controls both types of incontinence, or both types at once, and so is important to the many who suffer from this embarrassing and disabling disorder.

The present treatment methods are useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

depression, ICD 296.2 & 296.3, DSM 296, 294.80, 293.81, 293.82, 293.83, 310.10, 318.00, 317.00 migraine pain, particularly neuropathic pain bulimia, ICD 307.51, DSM 307.51 premenstrual syndrome or late luteal phase syndrome, DSM 307.90 alcoholism, ICD 305.0, DSM 305.00 & 303.90 tobacco abuse, ICD 305.1, DSM 305.10 & 292.00 panic disorder, ICD 300.01, DSM 300.01 & 300.21 anxiety, ICD 300.02, DSM 300.00 post-traumatic syndrome, DSM 309.89 memory loss, DSM 294.00 dementia of aging, ICD 290 social phobia, ICD 300.23, DSM 300.23 attention deficit hyperactivity disorder, ICD 314.0 disruptive behavior disorders, ICD 312 impulse control disorders, ICD 312, DSM 312.39 & 312.34 borderline personality disorder, ICD 301.83, DSM 301.83 chronic fatigue syndrome premature ejaculation, DSM 302.75 erectile difficulty, DSM 302.72 anorexia nervosa, ICD 307.1, DSM 307.10 disorders of sleep, ICD 307.4 autism mutism trichotillomania

Further, the compounds of Formula XII are particularly useful for alleviating the symptoms of smoking cessation or nicotine withdrawal when administered in combination with a serotonin reuptake inhibitor. The SRI's to be used in this treatment method, and the administration methods and formulations, are as described above. The use of the present compounds with SRI's in subjects striving to stop use of tobacco or nicotine provides surprisingly complete alleviation of the usual painful and damaging symptoms of such subjects, including nervousness, irritability, craving, excessive appetite, anxiety, depression in many forms, inability to concentrate, and the like. Thus, the control or elimination of weight gain in the subject undergoing withdrawal from or reduction of tobacco or nicotine use is a particularly valuable and preferred benefit of the use of a present compound in combination with an SRI.

Therapeutic applications

The compounds of Formula XII are useful for other important therapeutic purposes, as well as in combination with SRIs and in nicotine withdrawal or smoking cessation cases. In particular, the compounds are valuable for binding, blocking or modulating the serotonin $1_A$ receptor, and for the treatment or prophylaxis of conditions caused by or influenced by defective function of that receptor. In particular, the compounds are useful for antagonism at the serotonin $1_A$ receptor and accordingly are used for the treatment or prevention of conditions caused by or affected by excessive activity of that receptor.

More particularly, the compounds are useful in the treatment of anxiety, depression, hypertension, cognitive disorders, psychosis, sleep disorders, gastric motility disorders, sexual dysfunction, brain trauma, memory loss, appetite disorders and obesity, substance abuse, obsessive-compulsive disease, panic disorder and migraine.

Anxiety and its frequent concomitant, panic disorder, may be particularly mentioned in connection with the present compounds. The subject is carefully explained by the Diagnostic and Statistical Manual of Mental Disorders, published by the American Psychiatric Association, which classifies anxiety under its category 300.02. A further particularly noted disorder is depression and the group of depression-related disorders, which are discussed above in the discussion of adjunctive therapy with SRIs.

The unique combination of pharmacological properties possessed by the compounds of Formula XIII permit those compounds to be used in a method of simultaneously treating anxiety and depression. The anxiety portion of the combined syndrome is believed to be attacked by the 5HT-$1_A$ receptor-affecting property of the compounds, and the depression portion of the condition is believed to be addressed by the reuptake inhibition property. Thus, administration of an effective amount, as discussed above, of a compound of Formula XIII will provide treatment for the combined condition.

Pharmaceutical compositions

It is customary to formulate pharmaceuticals for administration, to provide control of the dosage and stability of the product in shipment and storage, and the usual methods of formulation are entirely applicable to the compounds of Formula I. Such compositions, comprising at least one pharmaceutically acceptable carrier, are valuable and novel because of the presence of the compounds of Formula I therein. Although pharmaceutical chemists are well aware of many effective ways to formulate pharmaceuticals, which technology is applicable to the present compounds, some discussion of the subject will be given here for the convenience of the reader.

The usual methods of formulation used in pharmaceutical science and the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compound in total, depending on the desired dose and the type of composition to be used. The amount of the compound, however, is best defined as the effective amount, that is, the amount of each compound which provides the desired dose to the subject in need of such treatment. The activity of the compounds do not depend on the nature of the composition, so the compositions are chosen and formulated solely for convenience and economy. Any compound may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the subject consumes the dosage form, and to avoid the difficulty in swallowing solid objects that bothers some subjects.

When it is desired to administer the combination as a suppository, the usual bases may be used. Cocoa butter is a traditional suppository base, which may be modified by addition of waxes to raise its melting point slightly. water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with pores through which the drugs are pumped by osmotic action.

The following typical formulae are provided for the interest and information of the pharmaceutical scientist.

Formulation 1

Hard gelatin capsules are prepared using the following ingredients:

|  | Quantity (mg/capsule) |
| --- | --- |
| Example 63 | 20 mg |
| Starch, dried | 200 mg |
| Magnesium stearate | 10 mg |
| Total | 230 mg |

Formulation 2

A tablet is prepared using the ingredients below:

|  | Quantity (mg/capsule) |
| --- | --- |
| Example 89 | 10 mg |
| Cellulose, microcrystalline | 400 mg |
| Silicon dioxide, fumed | 10 mg |
| Stearic acid | 5 mg |
| Total | 425 mg |

The components are blended and compressed to form tablets each weighing 425 mg.

Formulation 3

Tablets, each containing 10 mg of active ingredient, are made as follows:

|  |  |
| --- | --- |
| Example 78 | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

Formulation 4

Capsules, each containing 30 mg of active ingredient, are made as follows:

|  |  |
| --- | --- |
| Example 196 | 30 mg |
| Starch | 59 mg |
| Microcrystalline cellulose | 59 mg |
| Magnesium stearate | 2 mg |
| Total | 150 mg |

The active ingredient, cellulose, starch, and magnesium stearate are blended, passed through a No. 45 mesh U.S. sieve, and filled into hard gelatin capsules in 150 mg quantities.

Formulation 5

Suppositories, each containing 5 mg of active ingredient, are made as follows:

|  |  |
| --- | --- |
| Example 126 | 5 mg |
| Saturated fatty acid glycerides | 2,000 mg |
| Total | 2,005 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions, each containing 10 mg of active ingredient per 5 ml dose, are made as follows:

|  |  |
| --- | --- |
| Example 154 | 10 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 7

An intravenous formulation may be prepared as follows:

|  |  |
| --- | --- |
| Example 189 | 10 mg |
| Isotonic saline | 1,000 ml |

We claim:

1. A compound of the formula

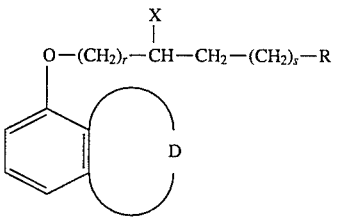

wherein
  r is 0–4;
  s is 0–1;
  D is a residue which combines with the carbon atoms to which it is attached to complete a pyrrolyl group;
  wherein X is hydrogen, phenyl, hydroxy or methoxy;
  provided that X is hydrogen or phenyl when r is 0;

R is

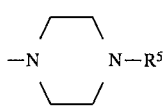

$R^5$ is $C_1$–$C_6$ alkyl or $C_1$–$C_4$ acyl;

or $R^5$ is $C_1$–$C_3$ alkyl substituted with benzodioxinyl or benzodioxolyl,
   substituted on the phenyl ring with 0–2 $C_1$–$C_3$ alkyl, $C_1$–$C_3$ alkoxy or halo groups;

or $R^5$ is pyridinyl, pyrimidinyl, indolyl, benzofuryl, benzothienyl, pyrazinyl, quinolinyl, isoquinolinyl, pyridazinyl or quinazolinyl,
   substituted with 0–2 $C_1$–$C_3$ alkyl, trifluoromethyl, $C_1$–$C_3$ alkoxy or halo groups;

or $R^5$ is

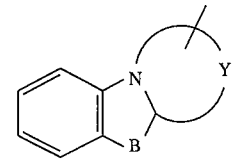

B is oxygen or sulfur;

Y is a residue which combines with the atoms to which it is attached to complete a triazolyl, imidazolyl, thiazolyl or pyrrolyl ring;

or a pharmaceutically acceptable salt thereof.

2. A pharmaceutical composition comprising a pharmaceutically acceptable carrier or excipient and a compound of claim 1.

3. A method of affecting the serotonin 1A receptor which comprises administering to a subject in need of such treatment an effective amount of a compound of the formula

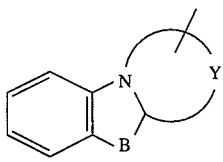

wherein r is 0–4;

s is 0–1;

D is a residue which combines with the carbon atoms to which it is attached to complete a pyrrolyl group;

wherein X is hydrogen, phenyl, hydroxy or methoxy;

provided that X is hydrogen or phenyl when r is 0;

R is

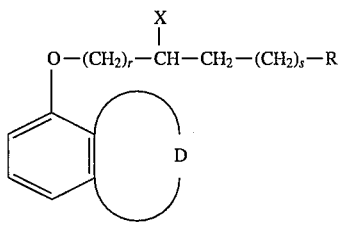

$R^5$ is $C_1$–$C_6$ alkyl or $C_1$–$C_4$ acyl;

or $R^5$ is $C_1$–$C_3$ alkyl substituted with phenyl, benzodioxinyl or benzodioxolyl,
   substituted on the phenyl ring with 0–2 $C_1$–$C_3$ alkyl, $C_1$–$C_3$ alkoxy or halo groups;

or $R^5$ is pyridinyl, phenyl, naphthyl, tetralinyl, pyrimidinyl, indolyl, benzofuryl, benzothienyl, pyrazinyl, quinolinyl, isoquinolinyl, pyridazinyl or quinazolinyl, substituted with 0–2 $C_1$–$C_3$ alkyl, trifluoromethyl, $C_1$–$C_3$ alkoxy or halo groups;

or $R^5$ is

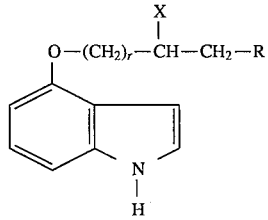

B is oxygen or sulfur;

Y is a residue which combines with the atoms to which it is attached to complete a triazolyl, imidazolyl, thiazolyl or pyrrolyl ring;

or a pharmaceutically acceptable salt thereof.

4. A method of inhibiting the reuptake of serotonin which comprises administering to a subject in need of such treatment an effective amount of a compound of formula

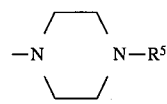

wherein r is 0–3;

X is hydrogen or hydroxy;

R is

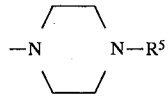

$R^5$ is phenyl, phenyl-$C_1$–$C_3$ alkyl, or diphenyl-$C_1$–$C_3$ alkyl, substituted with 1–2 halo, $C_1$–$C_3$ alkoxy or trifluoromethyl groups;

or a pharmaceutically acceptable salt thereof.

5. A method of claim 4 wherein the serotonin 1A receptor of the subject is also affected by the compound.

6. A method of preventing or alleviating the symptoms caused by withdrawal or partial withdrawal from the use of tobacco or of nicotine which comprises the method of claim 3.

7. A method of treating depression which comprises the method of claim 4.

8. A method of treating anxiety which comprises the method of claim 3.

9. A method of treating both anxiety and depression which comprises the method of claim 4.

10. A method of treating a condition chosen from the group consisting of hypertension, cognitive disorders, psychosis, sleep disorders, gastric motility disorders, sexual dysfunction, brain trauma, memory loss, eating disorders and obesity, substance abuse, obsessive-compulsive disease, panic disorder and migraine, comprising the method of claim 3.

11. A method of treating a condition chosen from the group consisting of obsessive-compulsive disease, obesity, migraine, pain, particularly neuropathic pain, bulimia, premenstrual syndrome or late luteal syndrome, alcoholism, tobacco abuse, panic disorder, anxiety, post-traumatic syndrome, memory loss, dementia of aging, social phobia, attention-deficit hyperactivity disorder, disruptive behavior disorders, impulsive control disorders, borderline personality disorder, chronic fatigue syndrome, premature ejaculation, erectile difficulty, anorexia nervosa, disorders of sleep, autism, mutism and trichotilomania, comprising the method of claim 4.

12. A method of potentiating the action of a serotonin reuptake inhibitor in increasing the availability of serotonin, norepinephrine and dopamine in the brain, comprising administering to a subject in need of such treatment a serotonin reuptake inhibitor in combination with the method of claim 3.

13. A method of claim 6 wherein a serotonin reuptake inhibitor is also administered to the subject.

14. A compound of claim 1 wherein X is hydrogen or hydroxy; s is 0; and r is 0–3.

15. A method of claim 3 wherein the compound is a compound wherein X is hydrogen or hydroxy; s is 0; and r is 0–3.

16. A method of treating anxiety which comprises the method of claim 15.

17. A method of treating a condition chosen from the group consisting of hypertension, cognitive disorders, psychosis, sleep disorders, gastric motility disorders, sexual dysfunction, brain trauma, memory loss, eating disorders and obesity, substance abuse, obsessive-compulsive disease, panic disorder and migraine, comprising the method of claim 15.

18. A method of preventing or alleviating the symptoms caused by withdrawal or partial withdrawal from the use of tobacco or of nicotine which comprises the method of claim 15.

19. A method of potentiating the action of a serotonin reuptake inhibitor in increasing the availability of serotonin, norepinephrine and dopamine in the brain, comprising administering to a subject in need of such treatment a serotonin reuptake inhibitor in combination with the method of claim 15.

* * * * *